(12) United States Patent
Yin et al.

(10) Patent No.: US 12,142,104 B2
(45) Date of Patent: Nov. 12, 2024

(54) METHODS AND COMPOSITIONS FOR MOLECULAR AUTHENTICATION

(71) Applicant: President and Fellows of Harvard College, Cambridge, MA (US)

(72) Inventors: Peng Yin, Cambridge, MA (US); Jocelyn Yoshiko Kishi, Cambridge, MA (US); Thomas E. Schaus, Cambridge, MA (US); Youngeun Kim, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1088 days.

(21) Appl. No.: 17/040,041

(22) PCT Filed: Mar. 21, 2019

(86) PCT No.: PCT/US2019/023371
§ 371 (c)(1),
(2) Date: Sep. 21, 2020

(87) PCT Pub. No.: WO2019/183359
PCT Pub. Date: Sep. 26, 2019

(65) Prior Publication Data
US 2021/0019973 A1 Jan. 21, 2021

Related U.S. Application Data

(60) Provisional application No. 62/646,728, filed on Mar. 22, 2018, provisional application No. 62/649,431, filed on Mar. 28, 2018, provisional application No. 62/650,096, filed on Mar. 29, 2018, provisional application No. 62/650,119, filed on Mar. 29, 2018,
(Continued)

(51) Int. Cl.
*G07D 7/14* (2006.01)
*C12Q 1/6813* (2018.01)

(52) U.S. Cl.
CPC ............. *G07D 7/14* (2013.01); *C12Q 1/6813* (2013.01); *C12Q 2563/185* (2013.01)

(58) Field of Classification Search
CPC .. G07D 7/14; C12Q 1/6813; C12Q 2563/185; C12Q 1/6818; C12Q 2565/101
USPC .............. 283/67, 70, 72, 74, 95, 96, 98, 901
See application file for complete search history.

(56) References Cited

U.S. PATENT DOCUMENTS

| | | |
|---|---|---|
| 5,543,507 A | 8/1996 | Cook et al. |
| 6,143,495 A | 11/2000 | Lizardi et al. |
| 8,772,011 B2 | 7/2014 | De Maria et al. |

(Continued)

FOREIGN PATENT DOCUMENTS

| | | |
|---|---|---|
| CN | 1836050 A | 9/2006 |
| CN | 101541975 A | 9/2009 |

(Continued)

OTHER PUBLICATIONS

Partial European Search Report mailed Jun. 25, 2018 for Application No. EP 16744150.0.

(Continued)

*Primary Examiner* — Justin V Lewis
(74) *Attorney, Agent, or Firm* — Wolf, Greenfield & Sacks, P.C.

(57) ABSTRACT

Provided herein, in some embodiments, are molecular authentication methods, systems, and compositions.

19 Claims, 46 Drawing Sheets

Related U.S. Application Data provisional application No. 62/739,756, filed on Oct. 1, 2018.

(56) References Cited

U.S. PATENT DOCUMENTS

| | | | |
|---|---|---|---|
| 9,273,349 | B2 | 3/2016 | Nguyen et al. |
| 9,284,602 | B2 | 3/2016 | Zhang et al. |
| 9,879,313 | B2 | 1/2018 | Chee et al. |
| 10,024,796 | B2 | 7/2018 | Lin et al. |
| 10,036,059 | B2 | 7/2018 | Zhang et al. |
| 11,098,355 | B2 | 8/2021 | Heron et al. |
| 11,286,517 | B2 | 3/2022 | Kishi et al. |
| 11,359,229 | B2 | 6/2022 | Kim et al. |
| 11,639,522 | B2 | 5/2023 | Schaus et al. |
| 2002/0065609 | A1 | 5/2002 | Ashby |
| 2004/0166520 | A1 | 8/2004 | Connolly |
| 2005/0045063 | A1 | 3/2005 | Niggemann et al. |
| 2005/0112610 | A1 | 5/2005 | Lee et al. |
| 2006/0063196 | A1 | 3/2006 | Akeson et al. |
| 2006/0286569 | A1 | 12/2006 | Bar-Or et al. |
| 2006/0286570 | A1 | 12/2006 | Rowlen et al. |
| 2007/0031829 | A1 | 2/2007 | Yasuno et al. |
| 2007/0042419 | A1 | 2/2007 | Barany et al. |
| 2007/0048761 | A1* | 3/2007 | Reep ................ C12Q 1/6816 435/6.11 |
| 2008/0299559 | A1 | 12/2008 | Kwok et al. |
| 2009/0042191 | A1 | 2/2009 | Hayward et al. |
| 2011/0129834 | A1 | 6/2011 | Chen et al. |
| 2011/0300640 | A1 | 12/2011 | Josten et al. |
| 2012/0014977 | A1 | 1/2012 | Furihata et al. |
| 2012/0021410 | A1 | 1/2012 | Yin et al. |
| 2012/0165219 | A1 | 6/2012 | van der Zaag et al. |
| 2012/0231972 | A1 | 9/2012 | Golyshin et al. |
| 2012/0253689 | A1 | 10/2012 | Rogan |
| 2013/0072390 | A1 | 3/2013 | Wang et al. |
| 2013/0225623 | A1 | 8/2013 | Buxbaum et al. |
| 2013/0244894 | A1 | 9/2013 | Mercolino |
| 2013/0261019 | A1 | 10/2013 | Lin et al. |
| 2014/0081665 | A1 | 3/2014 | Holmes et al. |
| 2014/0087377 | A1 | 3/2014 | Park et al. |
| 2014/0141984 | A1 | 5/2014 | Swartz et al. |
| 2014/0255921 | A1 | 9/2014 | Moysey et al. |
| 2014/0349288 | A1 | 11/2014 | Church et al. |
| 2015/0004615 | A1 | 1/2015 | Pierce et al. |
| 2015/0107475 | A1 | 4/2015 | Jung et al. |
| 2015/0111780 | A1 | 4/2015 | Mercolino |
| 2016/0024558 | A1 | 1/2016 | Hardenbol et al. |
| 2017/0327888 | A1 | 11/2017 | Ong et al. |
| 2018/0010174 | A1 | 1/2018 | Schaus et al. |
| 2019/0106733 | A1 | 4/2019 | Kishi et al. |
| 2019/0285644 | A1 | 9/2019 | Regev et al. |
| 2021/0277452 | A1 | 9/2021 | Kim et al. |
| 2022/0348990 | A1 | 11/2022 | Kishi et al. |
| 2023/0366011 | A1 | 11/2023 | Schaus et al. |

FOREIGN PATENT DOCUMENTS

| | | |
|---|---|---|
| CN | 104662165 A | 5/2015 |
| CN | 105121664 A | 12/2015 |
| CN | 106164298 A | 11/2016 |
| JP | 2008-017853 A | 1/2008 |
| JP | 2013-540451 A | 11/2013 |
| JP | 2014-504153 A | 2/2014 |
| JP | 2015-523864 A | 8/2015 |
| WO | WO 01/94625 A2 | 12/2001 |
| WO | WO 2004/046321 A2 | 6/2004 |
| WO | WO 2007/002016 A2 | 1/2007 |
| WO | WO 2007/117256 A1 | 10/2007 |
| WO | WO 2010/107416 A1 | 9/2010 |
| WO | WO 2011/156434 A2 | 12/2011 |
| WO | WO 2012/058488 A1 | 5/2012 |
| WO | WO 2012/058638 A2 | 5/2012 |
| WO | WO 2012/071428 A2 | 5/2012 |
| WO | WO 2012/078312 A2 | 6/2012 |
| WO | WO 2012/112804 A1 | 8/2012 |
| WO | WO 2013/012434 A1 | 1/2013 |
| WO | WO 2013/022694 A1 | 2/2013 |
| WO | WO 2013/140107 A1 | 9/2013 |
| WO | WO 2013/188912 A1 | 12/2013 |
| WO | WO 2014/018675 A1 | 1/2014 |
| WO | WO 2014/071361 A1 | 5/2014 |
| WO | WO 2014/074597 A1 | 5/2014 |
| WO | WO 2014/074648 A2 | 5/2014 |
| WO | WO 2014/130388 A1 | 8/2014 |
| WO | WO 2014/135838 A1 | 9/2014 |
| WO | WO 2014/144371 A1 | 9/2014 |
| WO | WO 2014/164958 A1 | 10/2014 |
| WO | WO 2015/095633 A1 | 6/2015 |
| WO | WO 2015/114469 A2 | 8/2015 |
| WO | WO 2016/011089 A1 | 1/2016 |
| WO | WO 2016/032562 A1 | 3/2016 |
| WO | WO 2016/123419 A1 | 8/2016 |
| WO | WO 2016/144755 A1 | 9/2016 |
| WO | WO 2017/143006 A1 | 8/2017 |
| WO | WO 2018/057502 A1 | 3/2018 |

OTHER PUBLICATIONS

Extended European Search Report mailed Sep. 25, 2018 for Application No. EP 16744150.0.
Invitation to Pay Additional Fees for PCT/US2016/015503 mailed Apr. 13, 2016.
International Search Report and Written Opinion for PCT/US2016/15503 mailed Jun. 27, 2016.
International Preliminary Report on Patentability for PCT/US2016/15503 mailed Aug. 10, 2017.
Extended European Search Report mailed Sep. 25, 2019 for Application No. 17753794.1.
Invitation to Pay Additional Fees for PCT/US2017/018086 mailed Apr. 17, 2017.
International Search Report and Written Opinion for PCT/US2017/018086 mailed Jun. 15, 2017.
International Preliminary Report on Patentability mailed Aug. 30, 2018 for PCT/US2017/018086.
Extended European Search Report mailed May 27, 2020, for Application No. 17853744.5.
Invitation to Pay Additional Fees mailed Dec. 6, 2017 for PCT/US2017/052234.
International Search Report and Written Opinion mailed Feb. 2, 2018 for PCT/US2017/052234.
International Preliminary Report on Patentability mailed May 16, 2019 for PCT/US2017/052234.
Invitation to Pay Additional Fees mailed May 29, 2019 for PCT/US2019/023371.
International Search Report and Written Opinion mailed Jul. 22, 2019 for Application No. PCT/US2019/023371.
International Preliminary Report on Patentability mailed Oct. 1, 2020, for Applicaton No. PCT/US2019/023371.
[No Author Listed], New COVID-19 Variants. Centers for Disease Control and Prevention. Updated Jan. 15, 2021. 3 pages.
Baccouche et al., Dynamic DNA-toolbox reaction circuits: a walkthrough. Methods. May 15, 2014;67(2):234-49. doi: 10.1016/j.ymeth.2014.01.015. Epub Feb. 2, 2014.
Beliveau et al., Versatile design and synthesis platform for visualizing genomes with Oligopaint FISH probes. Proc Natl Acad Sci U S A. Dec. 26, 2012;109(52):21301-6. doi:10.1073/pnas.1213818110. Epub Dec. 11, 2012.
Chen et al., Conditionally fluorescent molecular probes for detecting single base changes in double-stranded DNA. Nat Chem. 2013;5(9):782-9. Author Manuscript, 16 pages.
Dreyfus et al., A Supply chain management perspective on mitigating the risks of counterfeit products. Michigan State University. Oct. 2013. https://globaledge.msu.edu/Content/Uploads/Supply-Chain-Bgrounder_V8_FINAL_.pdf.
Forster et al., A human gut bacterial genome and culture collection for improved metagenomic analyses. Nat Biotechnol. 2019;37(2):186-192. doi:10.1038/s41587-018-0009-7.

(56) References Cited

OTHER PUBLICATIONS

Fredriksson et al., Protein detection using proximity-dependent DNA ligation assays. Nat Biotechnol. May 2002;20(5):473-7.
Green et al., Toehold switches: de-novo-designed regulators of gene expression. Cell. Nov. 6, 2014;159(4):925-39. doi: 10.1016/j.cell.2014.10.002. Epub Oct. 23, 2014. Author Manuscript, 28 pages.
Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.
Jungmann et al., Nanoscale imaging in DNA nanotechnology. Wiley Interdiscip Rev Nanomed Nanobiotechnol. Jan.-Feb. 2012;4(1):66-81. doi:10.1002/wnan.173. Epub Nov. 23, 2011.
Jungmann et al., Single-molecule kinetics and super-resolution microscopy by fluorescence imaging of transient binding on DNA origami. Nano Lett. Nov. 10, 2010;10(11):4756-61.
Li et al., Multiplexed detection of pathogen DNA with DNA-based fluorescence nanobarcodes. Nat Biotechnol. Jul. 2005;23(7):885-9. Epub Jun. 12, 2005.
Montagne et al., Programming an in vitro DNA oscillator using a molecular networking strategy. Mol Syst Biol. Feb. 1, 2011;7:466. doi: 10.1038/msb.2010.120. Erratum in: Mol Syst Biol. Mar. 8, 2011;7:476. Mol Syst Biol. 2011;7. doi:10.1038/msb.2011.12.
Pardee et al., Paper-based synthetic gene networks. Cell. Nov. 6, 2014;159(4):940-54. doi: 10.1016/j.cell.2014.10.004. Epub Oct. 23, 2014.
Sah et al., Complete Genome Sequence of a 2019 Novel Coronavirus (SARS-CoV-2) Strain Isolated in Nepal. Microbiol Resour Announc. Mar. 12, 2020;9(11):e00169-20. doi: 10.1128/MRA.00169-20.
Schaus et al, A DNA nanoscope via auto-cycling proximity recording. Nat Commun. Sep. 25, 2017;8(1):696(1-9).
Tribioli et al., Long-term room temperature storage of high-quality embryonic stem cell genomic DNA extracted with a simple and rapid procedure. J Biomol Tech. Sep. 2006;17(4):249-51.
Yan et al., Isothermal amplified detection of DNA and RNA. Mol Biosyst. May 2014;10(5):970-1003. doi: 10.1039/c3mb70304e.
Yin et al., Programming biomolecular self-assembly pathways. Nature. Jan. 17, 2008;451(7176):318-22. doi:10.1038/nature06451.
Zerberg et al., The major genetic risk factor for severe COVID-19 is inherited from Neanderthals. Nature. Nov. 2020;587(7835):610-612. doi: 10.1038/s41586-020-2818-3. Epub Sep. 30, 2020.
Zhang et al., Control of DNA strand displacement kinetics using toehold exchange. J Am Chem Soc. Dec. 2, 2009;131(47):17303-14. doi: 10.1021/ja906987s.
Zhang et al., Dynamic DNA nanotechnology using strand-displacement reactions. Nat Chem. 2011;3(2):103-13.
Zhang et al., Optimizing the specificity of nucleic acid hybridization. Nat Chem. Epub Jan. 22, 2012, 7 pages.
Zhu et al., Toehold-mediated strand displacement reaction triggered isothermal DNA amplification for highly sensitive and selective fluorescent detection of single-base mutation. Biosens Bioelectron. Sep. 15, 2014;59:276-81. doi: 10.1016/j.bios.2014.03.051. Epub Apr. 1, 2014.
U.S. Appl. No. 15/542,953, filed Dec. 4, 2017, Published, 2018-0010174.
U.S. Appl. No. 15/999,245, filed Aug. 17, 2018, Published, 2019-0106733.
U.S. Appl. No. 16/334,643, filed Mar. 19, 2019, Pending.
EP 16744150.0, Jun. 25, 2018, Partial European Search Report.
EP 16744150.0, Sep. 25, 2018, Extended European Search Report.
PCT/US2016/015503, Apr. 13, 2016, Invitation to Pay Additional Fees.
PCT/US2016/015503, Jun. 27, 2016, International Search Report and Written Opinion.
PCT/US2016/015503, Aug. 10, 2017, International Preliminary Report on Patentability.
EP 17753794.1, Sep. 25, 2019, Extended European Search Report.
PCT/US2017/018086, Apr. 17, 2017, Invitation to Pay Additional Fees.
PCT/US2017/018086, Jun. 15, 2017, International Search Report and Written Opinion.
PCT/US2017/018086, Aug. 30, 2018, International Preliminary Report on Patentability.
EP 17853744.5, May 27, 2020, Extended European Search Report.
PCT/US2017/052234, Dec. 6, 2017, Invitation to Pay Additional Fees.
PCT/US2017/052234, Feb. 2, 2018, International Search Report and Written Opinion.
PCT/US2017/052234, May 16, 2019, International Preliminary Report on Patentability.
PCT/US2019/023371, May 29, 2019, Invitation to Pay Additional Fees.
PCT/US2019/023371, Jul. 22, 2019, International Search Report and Written Opinion.
PCT/US2019/023371, Oct. 1, 2020, International Preliminary Report on Patentability.
U.S. Appl. No. 15/999,245, filed Aug. 17, 2018, Allowed, 2019-0106733.
U.S. Appl. No. 16/334,643, filed Mar. 19, 2019, Published, 2021-0277452.
EP 19771822.4, Nov. 18, 2021, Extended European Search Report. Extended European Search Report dated Nov. 18, 2021 for Application No. EP 19771822.4.
Fujimo et al., Quick, selective and reversible photocrosslinking reaction between 5-methylcytosine and 3-cyanovinylcarbazole in DNA double strand. Int J Mol Sci. Mar. 12, 2013;14(3):5765-74.
Kishi et al., Programmable autonomous synthesis of single-stranded DNA. Nat Chem. Feb. 2018;10(2):155-64. Epub Nov. 6, 2017.
U.S. Appl. No. 15/542,953, filed Dec. 4, 2017, Granted, U.S. Pat. No. 11,639,522.
U.S. Appl. No. 18/191,818, filed Mar. 28, 2023, Published, 2023-0366011.
U.S. Appl. No. 15/999,245, filed Aug. 17, 2018, Granted, U.S. Pat. No. 11,286,517.
U.S. Appl. No. 17/592,435, filed Feb. 3, 2022, Published, 2022-0348990.
U.S. Appl. No. 16/334,643, filed Mar. 19, 2019, Granted, U.S. Pat. No. 11,359,229.
U.S. Appl. No. 17/731,034, filed Apr. 27, 2022, Abandoned.

* cited by examiner previously used identical series of tests

Label w/ multiple scratches

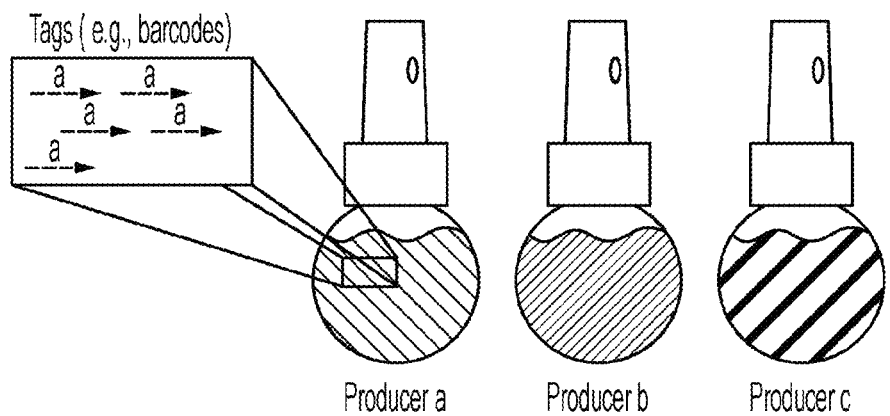
FIG. 10A
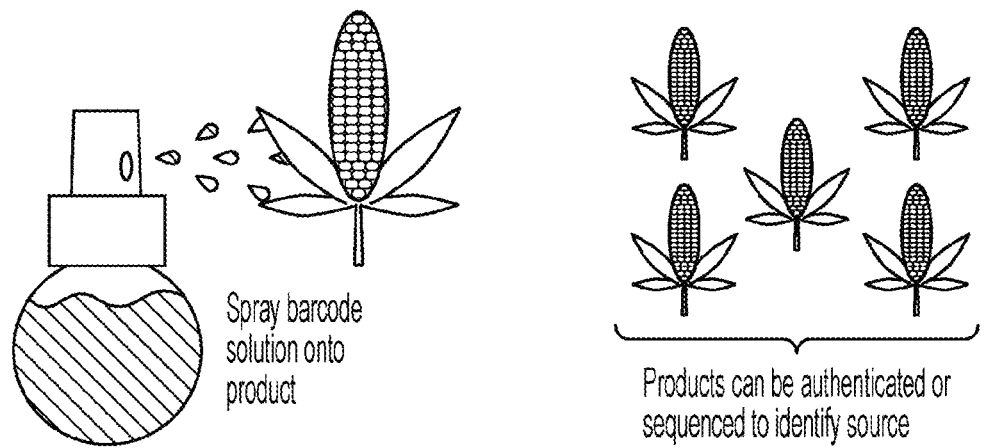
FIG. 10B
FIG. 10C

Unique barcode sequences

Unique barcodes with shared flanking sequences

Shared barcodes with unique flanking sequences

Unique barcodes with unique flanking sequences

Logic constraints
(e.g. X AND Y AND NOT Z)

Relative or absolute concentration/ratio-based constraints (e.g. twice as much X as Y, or 50nM of X and 25nM Y)

Structural constraints
(e.g. X bound to Y and Z unbound)

Topological constraints
(e.g. X and Y looped together)

Nanostructures (e.g. origami or brick structures verifiable by AFM/TEM device)

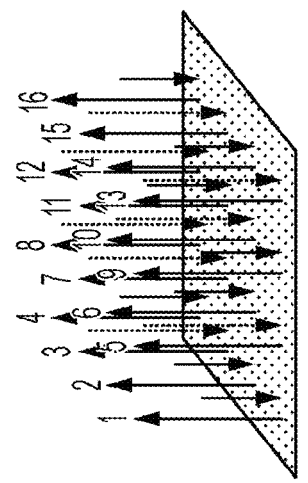
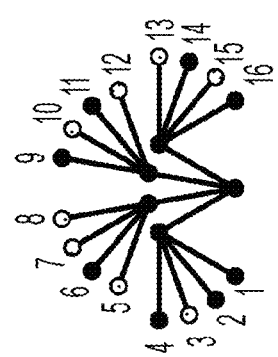
FIG. 16C
FIG. 16D

METHODS AND COMPOSITIONS FOR MOLECULAR AUTHENTICATION

RELATED APPLICATIONS

This application is a national stage filing under 35 U.S.C. § 371 of international application number PCT/US2019/023371, filed Mar. 21, 2019, which claims the benefit under 35 U.S.C. § 119(e) of U.S. provisional application No. 62/646,728, filed Mar. 22, 2018, U.S. provisional application No. 62/649,431, filed Mar. 28, 2018, U.S. provisional application No. 62/650,119, filed Mar. 29, 2018, U.S. provisional application No. 62/650,096, filed Mar. 29, 2018, and U.S. provisional application No. 62/739,756, filed Oct. 1, 2018, each of which is incorporated by reference herein in its entirety.

FEDERALLY SPONSORED RESEARCH

This invention was made with government support under 1317291 awarded by the National Science Foundation and under N00014-16-1-2410 awarded by Department of Defense Office of Naval Research. The government has certain rights in this invention.

BACKGROUND

Many products are exposed to potential fraudulent behavior throughout the supply chain. As supply chains for products become increasingly global, there is an increasing need for authentication, with track-and-trace technologies for raw materials and final products, for safety, security, and brand protection purposes.

SUMMARY

Provided herein, in some aspects, are molecular tag authentication systems, which physically couple the molecular tag to a product (e.g., textiles, apparel, art, electronics, jewelry, musical instruments, and/or pharmaceuticals). These authentication systems are robust (e.g., can withstand exposure to harsh environmental conditions), highly secure, and versatile (e.g., accommodates field testing). Synthetic oligonucleotides (oligos) are used to uniquely tag individual products or product batches (see, e.g., FIG. 1). A single unique oligo sequence may be used as a tag to identify a specific item (see, e.g., FIG. 1A), or a set of several oligos (e.g., 5-100, or 5, 10, 25, 50, 100, or more), optionally included at different relative concentrations, may be used to uniquely identify a product. A single unique oligo sequence may also be used to identify a batch of products (see, e.g., FIG. 1B). These synthetic oligos, referred to herein as "tags," may be single-stranded, double-stranded, partially single-stranded and partially double-stranded, linear, or hairpin molecules. It should be understood that the term "oligonucleotide" may be synonymous with the terms "polynucleotide" and "nucleic acid." It should also be understood that the term "tag" may be singular (tag) or plural (tags), unless specified otherwise. The tag may be included in/on a label. The label may be attached to or coupled to an entity.

It should be understood that the term "tag," may be used interchangeably with the terms "barcode key tag," "barcode sequences," "barcode" and "key." It should also be understood that the term "authenticating identifier" may be used interchangeably with the terms "lock" and "molecular lock."

The tags, in some embodiments, are short (e.g., 10-25 bp) nucleic acid (e.g., DNA) polynucleotides with known or partially-known sequences that can be added to a product (e.g., added to the surface of a product) and then later recovered for sequencing or other molecular authentication procedures to verify authenticity of the product. Short tags provide several advantages. For example, they are inexpensive to synthesize and are difficult to sequence (decode) without prior knowledge about the nucleotide sequence used to synthesize the tag. These advantages provide a stringent security barrier, making it difficult to easily decode and copy a tag.

In some embodiments, the tags are composed of (comprise) several distinct domains (specific sequences of nucleotides) used to molecularly verify the composition of the tag and to differentiate it from other, potentially counterfeit, tags. FIGS. 2A and 2B show an example of a tag that comprises a 5' domain X and a 3' domain. One of several mechanisms may be used to verify the tag. FIGS. 2A and 2B, for example, depict an authenticating identifier composition that may be used to verify the tag. This particular authenticating identifier composition includes three nucleic acid strands (simplified as "strands"): the first strand comprises, optionally in the 5' to 3' direction, domain a*, domain X, domain b*, and a quencher molecule; the second strand comprises, optionally in the 5' to 3' direction, a fluorophore molecule, domain b, and domain*; and the third strand comprises, optionally in the 5' to 3' direction, domain b and domain X*, wherein domain a binds to (e.g., is complementary to) domain a*, domain b binds to domain b*, and domain X binds to domain X*. Through a toehold exchange mechanism (see, e.g., WO 2012/058488, published May 3, 2012; Zhang S. et al., JACS, 2009, 131(47): 17303-17314; and Yang X. et al. JACS, 2016; 138(42); 14076-14082, each of which is entirely incorporated herein by reference), the correct tag may bind to the first quencher-labeled strand of the authenticating identifier composition to displace the second fluorophore-labeled strand, thereby activating fluorescence of the fluorophore molecule. The third strand of the authenticating identifier composition, because it is present at a high concentration (relative to the first and second oligo complex, e.g., at least 2-fold), may compete with the second fluorophore-labeled strand for binding to the first quencher-labeled strand. In this way, the second fluorophore-labeled strand remains dissociated from the first quencher-labeled strand so that that fluorescent signal can be detected, indicative of the presence of the correct tag. It should be understood that this system may also work if the fluorophore molecule is linked to the first strand and the quencher molecule is linked to the second strand. Thus, the first strand may be described as comprising one molecule of a quencher-fluorophore pair, and the second strand may be described as comprising the other molecule of a quencher-fluorophore pair.

Thus, provided herein, in some aspects, are molecular authentication methods that comprise distributing to a first entity of a supply chain a tag comprising a first strand that uniquely identifies a product of interest, optionally wherein the first strand has a length of shorter than 50 nucleotides (e.g., 45, 40, 35, 30, 25, 20, 15, or 10 nucleotides), and distributing to at least one (e.g., two, three, four, or more) additional entity an authenticating identifier composition comprising a second strand that binds to the first strand (e.g., the second strand contains a domain complementary to a domain of the first strand), wherein binding of the second strand to the first strand produces a detectable signal.

In some embodiments, the first entity is a manufacturer of the product of interest, and the second entity is a customer. In other embodiments, the first entity of the supply chain is selected from a supplier, a producer, a distributor, and a retailer, and wherein the second entity of the supply chain is selected from a producer, a distributor, a retailer, and a customer.

Other aspects of the present disclosure also provide molecular authentication methods that comprise contacting a product of interest at one step of a supply chain with a tag, wherein the tag comprises a first strand that uniquely identifies the product of interest, optionally wherein the first strand has a length of shorter than fifty (50) nucleotides, and combining the first strand of the tag with an authenticating identifier composition that comprises a second strand, wherein the second strand comprises a domain that binds to the first strand, and wherein binding of the second strand to the first strand produces a detectable signal.

Further aspects of the present disclosure provide molecular authentication methods, comprising (a) distributing to a first entity of a first supply chain a tag comprising a set of tag strands formed in a first pattern that uniquely identifies a first product of interest, optionally wherein the tag strands each have a length of shorter than fifty (50) nucleotides, (b) distributing to a second entity of a second supply chain a tag comprising the set of tag strands formed in a second pattern that uniquely identifies a second product of interest, and (c) distributing to at least one additional entity of the first supply chain and at least one additional entity of the second supply chain an authenticating identifier composition comprising at least one authenticating identifier strand that binds to the tag strands of (a) and (b), wherein binding of the at least one authenticating identifier strand to the tag strands produces a detectable signal in the shape of the first pattern and a detectable signal in the shape of the second pattern. In some embodiments, the first pattern is a logo of a first company, and the second pattern is a logo of a second company.

Some aspects of the present disclosure provides methods for producing a product that is authenticable by a user. The method includes admixing an article with a tag having at least one nucleic acid molecule, where interaction between the tag and an authenticating identifier exhibiting binding specificity for the tag yields a detectable signal that is indicative of authenticity of the product, thereby producing the product that is authenticable by the user.

In some embodiments, interaction between the tag and the authenticating identifier aids in yielding a distinct visual pattern that is indicative of authenticity of the product. In some embodiments, the visual pattern is a logo, an optical barcode or a geometric pattern. In some embodiments, the tag or the authenticating identifier comprises a nucleic acid molecule having a structure such that the nucleic acid molecule cannot be identified by sequencing. In some embodiments, the nucleic acid molecule comprises (i) a nucleic acid enantiomer; (ii) a backbone modification, (iii) a covalent modification to a base of the nucleic acid molecule, which covalent modification modulates hybridization of the base to another base; or (iv) at least one unnatural base pair. In some embodiments, the method further comprises admixing the article with a nucleic acid molecule that does not exhibit binding specificity for the authenticating identifier.

In some embodiments, the admixing attaches the tag to the article. In some embodiments, the admixing embeds the tag into the article. In some embodiments, the admixing embeds the tag into a layer attached to the article. In some embodiments, the admixing yields a mixture or solution comprising the tag and the article. In some embodiments, the tag is a hairpin molecule. In some embodiments, the tag is a single-stranded nucleic acid molecule. In some embodiments, the authenticating identifier comprises at least one nucleic acid molecule exhibiting sequence complementary to the tag.

In some embodiments, the interaction displaces a nucleic acid molecule hybridized to the authenticating identifier. In some embodiments, the interaction is hybridization. In some embodiments, the signal is an optical signal or an electronic signal. In some embodiments, the product takes a form selected from the group consisting of solid, semi-solid, vapor, or liquid. In some embodiments, the product is ingestible by a user. In some embodiments, the product is wearable. In some embodiments, the product is an electronic device. In some embodiments, the product is a consumer product. In some embodiments, the consumer product is selected from the group consisting of perfume, wine, a therapeutic, jewelry, a handbag, an automobile, clothing, a writing medium and furniture. In some embodiments, the product is a document, currency, or an original piece of art. In some embodiments, the product is a luxury product priced at $500 or more. In some embodiments, the product is not a nucleic acid research or diagnostic array. In some embodiments, the tag comprises a plurality of nucleic acid molecules.

Other aspects of the present disclosure provide products that are authenticable by a user, comprising an article admixed with a tag having at least one nucleic acid molecule, where interaction between the tag and an authenticating identifier exhibiting binding specificity for the tag yields a detectable signal that is indicative of authenticity of the product.

In some embodiments, interaction between the tag and the authenticating identifier aids in yielding a distinct visual pattern that is indicative of authenticity of the product. In some embodiments, the visual pattern is a logo, an optical barcode or a geometric pattern. In some embodiments, the tag or the authenticating identifier comprises a nucleic acid molecule having a structure such that the nucleic acid molecule cannot be identified by sequencing. In some embodiments, the nucleic acid molecule comprises (i) a nucleic acid enantiomer; (ii) a backbone modification, (iii) a covalent modification to a base of the nucleic acid molecule, which covalent modification modulates hybridization of the base to another base; or (iv) at least one unnatural base pair. In some embodiments, the tag is a single-stranded nucleic acid molecule.

In some embodiments, the tag is attached to the article. In some embodiments, the tag is embedded into the article. In some embodiments, the tag is embedded in a layer attached to the article. In some embodiments, the product comprises a mixture or solution of the tag and the article. In some embodiments, the tag is a hairpin molecule. In some embodiments, the authenticating identifier comprises a nucleic acid molecule exhibiting sequence complementarity to the tag. In some embodiments, the interaction displaces a nucleic acid molecule hybridized to the authenticating identifier. In some embodiments, the interaction is hybridization.

In some embodiments, the product is ingestible by a user. In some embodiments, the product is wearable. In some embodiments, the product is an electronic device. In some embodiments, the product is a consumer product. In some embodiments, the consumer product is selected from the group consisting of perfume, wine, a therapeutic, jewelry, a handbag, an automobile, clothing, a writing medium and furniture. In some embodiments, the product is a document, currency, or an original piece of art. In some embodiments, the product is not a nucleic acid research or diagnostic array.

In some embodiments, the tag comprises a plurality (more than one) of nucleic acid molecules. In some embodiments, the product further comprises one or more (at least one) additional tags admixed with the article and the tag, where the authenticating identifier does not exhibiting binding specificity for the one or more additional tags. In some embodiments, the product further comprises a transmission unit configured to transmit an electronic signal indicative of the presence or absence of the detectable signal to a designated party. In some embodiments, the designated party is (i) the producer of the product, (ii) a regulatory agency or personnel, (iii) a distributor in a supply chain, (iv) a party authorized to receive confirmation of authenticity or a lack thereof.

Other aspects of the present disclosure provide a method for testing authenticity of a product by a user, comprising: (i) applying a solution comprising an authenticating identifier to the product containing or suspected of containing a tag, where the authenticating identifier exhibits binding specificity for the tag such that interaction between the authenticating identifier and the tag yields a detectable signal that is indicative of authenticity of the product, and (ii) identifying a presence or absence of the detectable signal, thereby testing the authenticity of the product.

In some embodiments, interaction between the tag and the authenticating identifier aids in yielding a distinct visual pattern that is indicative of authenticity of the product. In some embodiments, the visual pattern is a logo, an optical barcode or a geometric pattern. In some embodiments, the tag or the authenticating identifier comprises a nucleic acid molecule having a structure such that the nucleic acid molecule cannot be identified by sequencing. In some embodiments, the nucleic acid molecule comprises (i) a nucleic acid enantiomer; (ii) a backbone modification, (iii) a covalent modification to a base of the nucleic acid molecule, which covalent modification modulates hybridization of the base to another base; or (iv) at least one unnatural base pair.

In some embodiments, the method further comprises alerting or notifying a party in a supply chain of the product as to the authenticity of the product. In some embodiments, the method further comprises requesting a remedial measure from a party in a supply chain of the article. In some embodiments, the remedial measure is a refund or a replacement. In some embodiments, the detectable signal is part of a pattern of optical signals. In some embodiments, the presence of the detectable signal indicates that the product is authentic.

In some embodiments, the product is ingestible by a user. In some embodiments, the product is wearable. In some embodiments, the product is an electronic device. In some embodiments, the product is a consumer product. In some embodiments, the consumer product is selected from the group consisting of perfume, wine, a therapeutic, jewelry, a handbag, an automobile, clothing, a writing medium and furniture. In some embodiments, the product is a document, currency, or an original piece of art. In some embodiments, the product is not a nucleic acid research or diagnostic array. In some embodiments, the tag comprises a plurality of nucleic acid molecules. In some embodiments, the product comprises one or more additional tags, where the authenticating identifier does not exhibit binding specificity for the one or more additional tags.

Other aspects of the present disclosure provide a method for product authentication. The method comprises: (a) generating an authenticating pair comprising a tag and an authenticating identifier usable for authenticating a product from a first party by a second party, where the tag comprises at least one nucleic acid molecule and the authenticating identifier exhibits binding specificity for the tag, and where the product comprises the tag; (b) providing the tag or information concerning the tag to the first party to effect the first party to produce the product comprising the tag; and (c) providing the authenticating identifier or information concerning the authenticating identifier to a second party, where interaction between the tag and the authenticating identifier exhibiting binding specificity for the tag yields a detectable signal that is indicative of authenticity of the product.

In some embodiments, interaction between the tag and the authenticating identifier aids in yielding a distinct visual pattern that is indicative of authenticity of the product. In some embodiments, the visual pattern is a logo, an optical barcode or a geometric pattern. In some embodiments, the tag or the authenticating identifier comprises a nucleic acid molecule having a structure such that the nucleic acid molecule cannot be identified by sequencing. In some embodiments, the nucleic acid molecule comprises (i) a nucleic acid enantiomer; (ii) a backbone modification, (iii) a covalent modification to a base of the nucleic acid molecule, which covalent modification modulates hybridization of the base to another base; or (iv) at least one unnatural base pair. In some embodiments, the product comprises one or more additional tags that do not exhibit binding specificity for the authenticating identifier.

In some embodiments, the first party and the second party are members of a supply chain. In some embodiments, the generating an authenticating pair comprises selecting a tag from a plurality of tags and selecting an authenticating identifier from a plurality of authenticating identifiers, where the authenticating identifier exhibits binding specificity for the tag. In some embodiments, the authenticating identifier does not exhibit binding specificity for other tags from the plurality of tags. In some embodiments, the tag is provided to the first party in solution form. In some embodiments, information of the tag and/or information of the authenticating identifier is provided to the first party in electronic format. In some embodiments, the authenticating identifier is provided to the second party in solution form.

Other aspects of the present disclosure provide a computer system for generating an authenticating pair comprising a tag and an authenticating identifier usable for authenticating a product from a first party by a second party along a supply chain. The computer system comprises: one or more databases comprising (i) a first set of data corresponding to a plurality tags, which plurality of tags comprises at least one nucleic acid molecules, and (ii) a second set of data corresponding to a plurality of authenticating identifiers, which plurality of authenticating identifiers comprises the authenticating identifier, where the authenticating identifier exhibits binding specificity for the tag; and one or more computer processors operatively coupled to the one or more databases, where the computer processor is programmed to (i) generate the authenticating pair comprising the tag and the authenticating identifier, and (ii) store the authenticating pair in memory, where the authenticating pair is usable by the second party along the supply chain to authenticate the product from the first party, using a detectable signal generated upon interaction between the tag and the authenticating identifier.

In some embodiments, the computer processor is programmed to transmit the tag to the first party. In some embodiments, the computer processor is programmed to transmit the authenticating identifier to the second party.

Other aspects of the present disclosure provide a computer system for detecting authentication of a product from a first party by a second party along a supply chain. The computer system comprises one or more databases comprising (i) a first set of data corresponding to a plurality tags, an individual tag of the plurality is admixed with a product by the first party, which plurality of tags having at least one nucleic acid molecules, and (ii) a second set of data corresponding to a plurality of authenticating identifiers, which plurality of authenticating identifiers comprises the authenticating identifier, where the authenticating identifier exhibits binding specificity for the tag, and where interaction between the authenticating identifier and the tag yields a detectable signal that is indicative of authenticity of the product; and one or more computer processors operatively coupled to the one or more databases, and programmed to receive an electronic signal indicating a presence or absence of the detectable signal.

In some embodiments, the one or more computer processors are programmed to receive the electronic signal concurrent or subsequent to the interaction between the tag and the authenticating identifier. In some embodiments, the electronic signal is transmitted from the product or the second party when the second party triggers the interaction between the tag and the authenticating identifier. In some embodiments, the one or more computer processors are programmed to transmit to a designated party a confirmation of authentication or a lack thereof to a party upon receipt of the electronic signal. In some embodiments, the designated party is (i) the producer of the product; (ii) a regulatory agency or personnel; (iii) a distributor of the supply chain; or (iv) a party authorized to receive such confirmation or the lack thereof. In some embodiments, the computer system is configured to monitor status of authentication in real-time.

In some embodiments, the product comprises a transmission unit configured to transmit data concerning the detectable signal. In some embodiments, the one or more processors are configured to receive information from and transmit information to the product, first party, and/or the second party, where the information comprises data relating to status of authentication of the product. In some embodiments, the one or more processors are configured to correlate data relating to status of authentication of a given product to geographic information of: (i) the product, and/or (ii) a party in or outside of the supply chain possessing the product.

Other aspects of the present disclosure provide a molecular complex comprising a first nucleic acid molecule coupled to a second nucleic acid molecule through a third nucleic acid molecule having sequence complementarity with the first nucleic acid molecule and the second nucleic acid molecule, which second nucleic acid molecule is conjugated to an enzyme.

In some embodiments, the enzyme catalyzes a reaction yielding a detectable signal. In some embodiments, the enzyme catalyzes a reaction yielding a signal that is detectable by a naked eye without aid of a detector. In some embodiments, the first nucleic acid molecule is coupled to an article. In some embodiments, the first nucleic acid molecule is coupled to the article at a first region, and where the article comprises a second region comprising the third nucleic acid molecule having sequencing complementarity with the second nucleic acid molecule, where interaction between the second nucleic acid molecule and the third nucleic acid molecule yields a detectable signal.

Other aspects of the present disclosure provide a product comprising an article admixed with a molecular complex, which molecule complex comprises a first nucleic acid molecule coupled to a second nucleic acid molecule through a third nucleic acid molecule having sequence complementarity with the first nucleic acid molecule and the second nucleic acid molecule, where the second nucleic acid molecule is conjugated to an enzyme.

In some embodiments, the first nucleic acid molecule is coupled to the article. In some embodiments, the first nucleic acid molecule is coupled to the article at a first region, and where the article comprises a second region comprising the third nucleic acid molecule having sequencing complementarity with the second nucleic acid molecule, where interaction between the second nucleic acid molecule and the third nucleic acid molecule yields a detectable signal. In some embodiments, the product is wearable. In some embodiments, the product is an electronic device. In some embodiments, the product is a consumer product. In some embodiments, the consumer product is selected from the group consisting of perfume, wine, a therapeutic, jewelry, a handbag, an automobile, clothing, a writing medium and furniture. In some embodiments, the product is a document, currency or an original piece of art. In some embodiments, the product is not a nucleic acid research or diagnostic array.

Other aspects of the present disclosure provide an authenticable writing medium, comprising a tag having at least one nucleic acid molecule, where application of the authenticable writing medium by a user to an article yields a marking on the article comprising the tag, where the tag is detectable upon interacting with an authenticating identifier exhibiting binding specificity for the tag, where the interaction yields a detectable signal that is indicative of authenticity of the marking made by the user or a party designated by the user, and where the tag or the authenticating identifier comprises a nucleic acid molecule having a structure such that the nucleic acid molecule cannot be identified by sequencing.

In some embodiments, the authenticable writing medium takes a form selected from the group consisting of a solid, a semi-solid, a vapor, or a liquid. In some embodiments, the authenticable writing medium is formulated as an ink. In some embodiments, the writing medium is formulated in the form of a powder.

Other aspects of the present disclosure provide a method of identifying a subject comprising: (a) providing an article suspected or expected to be produced by the subject, the article comprising a tag unique to the subject and having at least one nucleic acid molecule, where interaction of the tag with an authenticating identifier exhibiting binding specificity for the tag yields a detectable signal that is indicative of identity of the subject; (b) applying the authenticating identifier to the article; and (c) identifying the subject when the detectable signal is detected.

In some embodiments, the article is made of a material amenable for admixing the tag. In some embodiments, the article is a personal article selected from the group consisting of a document written by the subject, clothing worn by the subject, an ingestible product ingested by the subject, a tool utilized by the subject and a drug utilized by the subject. In some embodiments, the article is the subject's Will. In some embodiments, the article is a check issued by the subject. In some embodiments, the subject is an animal. In some embodiments, the subject is human.

Other aspects of the present disclosure provide a method of identifying an entity, comprising: (a) providing an article suspected or expected to be produced by the entity, the article comprising a tag unique to the entity and optionally sharing commonality with a reference tag, the tag having at least one nucleic acid molecule, where interaction of the tag with an authenticating identifier exhibiting binding specificity for the tag yields a detectable signal that is indicative of identity of the entity; (b) applying the authenticating identifier to the article; and (c) identifying the entity when the detectable signal is detected.

In some embodiments, the entity is a corporation, organization, or a group of affiliated units. In some embodiments, the article is made of a material amendable for admixing the tag. In some embodiments, the article is a product marketed by the entity. In some embodiments, the reference tag interacts specifically with a reference authenticating identifier to yield an additional detectable signal indicative of an entity of higher organizational hierarchy to which the entity belongs.

Other aspects of the present disclosure provide a device for generating an authenticable ink on an article comprising a housing comprising: a first container comprising a first solution comprising an ink, where application of the first solution to the article yields at least one ink layer comprising the ink; and a second container comprising a second solution comprising a tag, where application of the second solution to the at least one layer yields the authenticable ink comprising the tag, where interaction between the tag and an authenticating identifier exhibiting binding specificity for the tag yields a detectable signal that is indicative of authenticity of (i) the ink, (ii) a user-generated pattern of the ink layer, or (iii) the article.

In some embodiments, the first container is separate from the second container. In some embodiments, the device further comprises a first applicator in fluid communication with the first container, where the first applicator is configured to direct flow of the first solution to the article. In some embodiments, the device further comprises a second applicator in fluid communication with the second container, where the second applicator is configured to direct flow of the second solution to the at least one ink layer. In some embodiments, the first applicator and the second applicator are the same.

Other aspects of the present disclosure provide a non-transitory computer readable medium comprising machine executable code that, upon execution by one or more computer processors, implements any of the methods above or elsewhere herein.

Other aspects of the present disclosure provide a system comprising one or more computer processors and computer memory coupled thereto. The computer memory comprises machine executable code that, upon execution by the one or more computer processors, implements any of the methods above or elsewhere herein.

The authentication systems, methods and compositions of the present disclosure generally include tag and authenticating identifier component(s). It should be understood that in any of the embodiments herein, the tag component(s) may be applied to or associated with a product or article, while the authenticating identifier component(s) may be contacted with or added to the product. Likewise, in any of the embodiments herein, the authenticating identifier component(s) may be applied to or associated with a product or article, while the tag component(s) may be contacted with or added to the product or article.

Other aspects of the present disclosure provide a molecular authentication method comprising (a) distributing to a first entity of a supply chain a tag comprising a nucleic acid nanostructure that uniquely identifies a product of interest, wherein the nanostructure is linked to a docking strand; and (b) distributing to an additional entity an authenticating identifier composition comprising a signal generating imager strand that binds to the docking strand, wherein binding of the imager strand to the docking strand produces a detectable signal.

Other aspects of the present disclosure provide a molecular authentication method, comprising (a) providing a product of interest at one step of a supply chain, wherein the product of interest comprises a tag that comprises a nucleic acid nanostructure that uniquely identifies the product of interest, wherein the nucleic acid nanostructure is linked to a docking strand; and (b) combining the tag with an authenticating identifier composition that comprises a signal generating imager strand that binds to the docking strand, wherein binding of the imager strand to the docking strand produces a detectable signal.

Other aspects of the present disclosure provide a method of identifying a subject, comprising (a) providing a product suspected or expected to be produced by a subject, wherein the article comprises a tag comprising a nucleic acid nanostructure unique to said subject, wherein the nucleic acid nanostructure comprises a docking strand, and wherein interaction of the tag with an authenticating identifier composition comprising a signal generating imager strand exhibiting binding specificity for the docking strand yields a detectable signal that is indicative of identity of the subject; (b) applying the authenticating identifier composition to the article; and (c) identifying the subject when the detectable signal is detected.

Other aspects of the present disclosure provide a molecular authentication method, comprising (a) distributing to a first entity of a supply chain a tag comprising a scaffold strand or a plurality of single-stranded tiles (SSTs) that uniquely identifies a product of interest and requires a plurality of additional strands or SSTs to assemble into a nanostructure; and (b) distributing to an additional entity an authenticating identifier composition comprising a plurality of staple strands or a plurality of additional SSTs that bind to the scaffold strand or the plurality of SSTs to assemble the nanostructure, optionally wherein the additional staple strands or SSTs comprise a detectable moiety.

Other aspects of the present disclosure provide a molecular authentication method, comprising (a) providing a product of interest at one step of a supply chain, wherein the product of interest comprises a tag that comprises a scaffold strand or a plurality of single-stranded tiles (SSTs) that uniquely identifies a product of interest and requires a plurality of additional strands or SSTs to assemble into a nanostructure; and (b) combining the tag with an authenticating identifier composition comprising a plurality of staple strands or a plurality of additional SSTs that bind to the scaffold strand or the plurality of SSTs to assemble the nanostructure, optionally wherein the additional staple strands or SSTs comprise a detectable moiety.

Other aspects of the present disclosure provide a method of identifying a subject, comprising (a) providing a product suspected or expected to be produced by a subject, wherein the article comprises a tag comprising a scaffold strand or a plurality of single-stranded tiles (SSTs) that uniquely identifies a product of interest and requires a plurality of additional strands or SSTs to assemble into a nanostructure, and wherein interaction of the tag with an authenticating identifier composition comprising a plurality of staple strands or a plurality of additional SSTs that bind to the scaffold strand or the plurality of SSTs to assemble the nanostructure yields a nucleic acid nanostructure that is indicative of identity of the subject; (b) applying the authenticating identifier composition to the article; and (c) identifying the subject when the nucleic acid nanostructure is assembled.

Other aspects of the present disclosure provide a molecular authentication method, comprising (a) distributing to a first entity of a supply chain a tag comprising a nucleic acid array that uniquely identifies a product of interest, wherein the array comprises a plurality of docking strands positioned into a first pattern or shape; and (b) distributing to an additional entity an authenticating identifier composition comprising imager strands that bind to the docking strands, optionally wherein the imager strands comprise a detectable moiety, wherein binding of the imager strands to the docking strands generates a second pattern or shape.

Other aspects of the present disclosure provide a molecular authentication method, comprising (a) providing a product of interest at one step of a supply chain, wherein the product of interest comprises a tag that comprises a nucleic acid array that uniquely identifies a product of interest, wherein the array comprises a plurality of docking strands positioned into a first pattern or shape; and (b) combining the tag with an authenticating identifier composition comprising imager strands that bind to the docking strands, optionally wherein the imager strands comprise a detectable moiety, wherein binding of the imager strands to the docking strands generates a second pattern or shape.

Other aspects of the present disclosure provide a method of identifying a subject, comprising (a) providing a product suspected or expected to be produced by a subject, wherein the article comprises a tag comprising a nucleic acid array that uniquely identifies a product of interest, wherein the array comprises a plurality of docking strands positioned into a first pattern or shape, and wherein interaction of the tag with an authenticating identifier composition comprising imager strands that bind to the docking strands, optionally wherein the imager strands comprise a detectable moiety, wherein binding of the imager strands to the docking strands yields a second pattern or shape that is indicative of identity of the subject; (b) applying the authenticating identifier composition to the article; and (c) identifying the subject when the nucleic acid nanostructure is assembled.

In some embodiments, a nucleic acid nanostructure is a DNA origami structure or a DNA brick structure.

In some embodiments, an imager strand binds to a docking strand through direct hybridization, toehold exchange reaction, primer exchange reaction, ligation reaction, or hybridization chain reaction. In some embodiments, an imager strand is linked to a fluorophore.

In some embodiments, an interaction between a tag and an authenticating identifier, or between an imager strand and a docking strand, is detected using optical detectors, electronic detectors, atomic force microscopy, transmission electron microscopy, or super-resolution imaging techniques (e.g. DNA-PAINT).

In some embodiments, an array comprises $2^n$ strands, wherein n is the number of uniquely addressable locations within a pattern or shape. In some embodiments, an array comprises $m^n$ strands, wherein m is the number of possible configurations of the at least one array and n is the number of uniquely addressable locations within a pattern or shape. In some embodiments, a pattern or shape can be detected with the naked eye. In some embodiments, an array comprises a plurality of strands that have been ink jet or contact printed onto a surface. In some embodiments, an array comprises a plurality of strands that are positioned apart from one another at a distance of 20 nanometers up to 5 microns. In some embodiments, a tag or signal may be may be amplified prior to, during, or after binding of the second strand with the first strand. In some embodiments, a tag or signal may be may be amplified prior to, during, or after binding or interaction of the authenticating identifier strand with the tag strand(s).

In some embodiments, a tag or signal may be amplified using at least one enzymatic method. In some embodiments, an enzymatic method is a Polymerase Chain Reaction (PCR), Loop-Mediated Isothermal Amplification (LAMP), Rolling Circle Amplification (RCA), Recombinase Polymerase Amplification (RPA), nick and extend-type scheme and/or signal amplification by exchange reaction (SABER).

In some embodiments, a tag or signal may be amplified using at least one non-enzymatic method. In some embodiments, a non-enzymatic method involve the use of dynamic nucleic acid circuits, which can rapidly change state in the presence of a nucleic acid trigger. In some embodiments, a non-enzymatic method involves direct conversion of a non-nucleic acid signal in the presence of nanoparticle or enzyme. In some embodiments, a nanoparticle is a gold nanoparticle.

In some embodiments, a tag or signal may be amplified at a constant temperature.

Another example of a molecular barcode authentication system is provided in FIG. 27A. The tags are applied to a product of interest, and at some point in the supply chain (e.g., when the end customer received the product), the tags are applied to a test substrate to produce a detectable signal that authenticates the product from which the tags were obtained. Alternatively, a test substrate may accompany the product of interest, while the tags are distributed to another step of the supply chain. FIG. 27A depicts a test substrate comprising a series of regions designed to collectively determine whether a specific tag is present in a liquid sample. In this particular example, the test substrate comprises, in the following order (ordered position on the test substrate), (i) a source region comprising enzyme-linked strands, (ii) a test region comprising immobilized test strands and an embedded enzyme substrate, and (iii) a control region comprising an embedded enzyme substrate and immobilized control strands that bind to the enzyme-linked strands. A liquid sample (suspected of containing the tags) is first applied to one end of the test substrate. Capillary action transports any tags in the liquid sample through each region of the test substrate. As the liquid sample passes through the source region, it collects the enzyme-linked strands and proceeds to the test region. In the test region, the tags if present in the sample bind to and bridges together the immobilized test strands and the enzyme-linked strands (see, e.g., test region of FIG. 27A, bottom panel), forming a complex that produces a colorimetric signal—the now-immobilized enzymes react with the enzyme substrate in the test region). The sample continues to the positive control region, wherein the immobilized control strands bind to the enzyme-linked strands, forming yet another complex that produces a colorimetric signal, indicating completion of the test.

Another example of a molecular barcode authentication system is provided in FIG. 27B. In this example, the test substrate is configured to include (i) a source region comprising enzyme-linked strands, immobilized source strands, and bridge strands, wherein the bridge strands bind both the enzyme-linked strands and the source strands, and (ii) a test region comprising an embedded enzyme substrate. The liquid sample (suspected of containing the tags) is first applied to one end of the test substrate. Capillary action transports any tags in the liquid sample through each region of the test substrate, as described above. As the liquid sample passes through the source region, the tags if present in the sample bind to the bridge strands through a toehold-mediate mechanism, thereby displacing the bridge strand and freeing the enzyme-linked strands. The liquid sample continues through the test substrate carrying the enzyme-linked strands to the test region, where the enzyme linked strands react with the embedded substrate to produce a colorimetric signal (see, e.g., test region of FIG. 27B, bottom panel). Positive and negative controls may be provided separately, as depicted in FIG. 27C.

While the examples described above utilize an enzyme/substrate-based reaction to produce a colorimetric signal, the present disclosure also encompasses the use of pigments (e.g., biological pigments) instead of enzymes (i.e., pigment-linked strands). The use of pigments, in some embodiments, negates a need for the use of an embedded substrate. See, e.g., FIGS. 27C and 27D.

The verification/authentication systems of the present disclosure generally include tag(s) and a (at least one) test substrate (e.g., that includes authentication strand(s), such as enzyme-linked strands, source strands, test strands, and/or control strands). It should be understood that in any of the embodiments herein, the tag(s) may be applied to or associated with a product, while the test substrate is distributed to an entity in a supply chain (e.g., end customer). Likewise, in any of the embodiments herein, the test substrate may be applied to or associated with a product, while the tag(s) are distributed to an entity in a supply chain.

Some aspects of the present disclosure provide molecular authentication methods, comprising: (a) providing a test substrate that comprises, in the following order, (i) a source region comprising enzyme-linked strands, (ii) a test region comprising immobilized test strands and an embedded enzyme substrate, and (iii) a control region comprising immobilized control strands that bind to the enzyme-linked strands and an embedded enzyme substrate; (b) applying to the test substrate a sample that optionally comprises tags that bind to the enzyme-linked strands and to the immobilized test strands; and (c) detecting a colorimetric signal in the test region and/or detecting a colorimetric signal in the control region (see, e.g., FIG. 27A).

In some embodiments, the colorimetric signal in the test region is produced by binding of the tags to the immobilized test strands. In some embodiments, the colorimetric signal in the control region is produced by binding of the enzyme-linked strands to the immobilized control stands.

In some embodiments, the tags are 10-30 nucleotides in length.

Other aspects of the present disclosure provide methods comprising (a) providing a test substrate that comprises, in the following order, (i) a source region comprising enzyme-linked strands, immobilized source strands, and bridge strands, wherein the bridge strands bind both the enzyme-linked strands and the source strands, and (ii) a test region comprising an embedded enzyme substrate, (b) applying to the test substrate a sample that optionally comprises tags that bind to the bridge strands, and (c) detecting a colorimetric signal in the test region or detecting a colorimetric signal in the source region (see, e.g., FIG. 27B).

In some embodiments, the methods further comprise (a) providing a positive control substrate that comprises, in the following order, (i) a source region comprising enzyme-linked strands, and (ii) a positive control region comprising an embedded enzyme substrate, (b) applying the sample to the positive control substrate, and (c) detecting a colorimetric signal in the positive control region (see, e.g., FIG. 27C, top panel).

In some embodiments, the methods further comprise (a) providing a negative control substrate that comprises, in the following order, (i) a source region comprising enzyme-linked strands, immobilized source strands, and negative control bridge strands, wherein the negative control bridge strands bind both the enzyme-linked strands and the immobilized source strands but do not bind the tags, and (ii) a negative control region comprising an embedded enzyme substrate, (b) applying the sample to the negative control substrate, and (c) detecting a colorimetric signal in the source region (see, e.g., FIG. 27C, bottom panel).

Yet other aspects of the present disclosure provide methods comprising (a) providing a test substrate that comprises, in the following order, (i) a source region comprising pigment-linked strands, immobilized source strands, and bridge strands, wherein the bridge strands bind both the pigment-linked strands and the source strands, and (ii) a test region, (b) applying to the test substrate a sample that optionally comprises tags that bind to the bridge strands, and (c) detecting pigment in the source region or the test region (see, e.g., FIG. 27D).

In some embodiments, the methods further comprise (a) providing a positive control substrate that comprises, in the following order, (i) a source region comprising pigment-linked strands, and (ii) a positive control region, (b) applying the sample to the positive control substrate, and (c) detecting a colorimetric signal in the positive control region (see, e.g., FIG. 27E, top panel).

In some embodiments, the methods further comprise (a) providing a negative control substrate that comprises, in the following order, (i) a source region comprising pigment-linked strands, immobilized source strands, and negative control bridge strands, wherein the negative control bridge strands bind both the pigment-linked strands and the immobilized source strands but do not bind the tags, and (ii) a negative control region, (b) applying the sample to the negative control substrate, and (c) detecting a colorimetric signal in the source region (see, e.g., FIG. 27E, bottom panel).

Some aspects of the present disclosure provide nanoparticle-based authentication methods, comprising: distributing to a first entity of a supply chain a tag (e.g., a unique nucleic acid strand); and distributing to a second entity of the supply chain an authenticating identifier that comprises a first nanoparticle linked to a first authentication strand, a second nanoparticle linked to a second authentication strand, and optionally a third authentication strand, wherein in solution the tag binds to the first authentication strand, the second authentication strand, and/or the third authentication strand and triggers aggregation or disaggregation of the first nanoparticle and the second nanoparticle to produce a color change in the solution. In some embodiments, the authentications strands are nucleic acid strands, such as single-stranded nucleic acid molecules.

In some embodiments, the authentication methods comprise: contacting a product of interest with a tag at a first stage of a supply chain; removing the tag from the product of interest at a second stage of the supply chain; and combining the removed tag with a solution comprising a first nanoparticle linked to a first authentication strand, a second nanoparticle linked to a second authentication strand, and optionally a third authentication strand, wherein in solution the tag binds to the first authentication strand, the second authentication strand, and/or the third authentication strand and triggers aggregation or disaggregation of the first nanoparticle and the second nanoparticle to produce a color change in the solution.

In other embodiments, the authentication methods comprise: combining, in a solution, a first nanoparticle linked to a first authentication strand, a second nanoparticle linked to a second authentication strand, optionally a third authentication strand, and a tag that binds to the first authentication strand, the second authentication strand, and/or the third authentication strand; and triggering aggregation or disaggregation of the first nanoparticle and the second nanoparticle to produce a color change in the solution.

In some embodiments, the authentication methods comprise: distributing to a first entity of a supply chain a tag; and distributing to a second entity of the supply chain a primer that binds to the tag, strand displacing polymerase, dNTPs, and a plurality of nanoparticles, wherein each nanoparticle of the plurality is linked to a authentication strand, wherein in solution the primer, strand displacing polymerase, dNTPs, and the tag react to form a concatemer that binds to authentication strands of the nanoparticles and forms a nanoparticle aggregate to produce a color change in the solution.

In some embodiments, the authentication methods comprise: contacting a product of interest with a tag at a first stage of a supply chain; optionally removing the tag from the product of interest at a second stage of the supply chain; and combining the tag with a primer that binds to the tag, strand displacing polymerase, dNTPs, and a plurality of nanoparticles, wherein each nanoparticle of the plurality is linked to a authentication strand, wherein in solution the primer, strand displacing polymerase, dNTPs, and the tag react to form a concatemer that binds to authentication strands of the nanoparticles and forms a nanoparticle aggregate to produce a color change in the solution.

In other embodiments, the authentication methods comprise: combining, in a solution, a tag, a primer that binds to the tag, strand displacing polymerase, dNTPs, and a plurality of nanoparticles, wherein each nanoparticle of the plurality is linked to a authentication strand; producing a concatemer that binds to authentication strands of the nanoparticles; and forming a nanoparticle aggregate to produce a color change in the solution.

In some embodiments, the authentication methods comprise: distributing to a first entity of a supply chain a tag; and distributing to a second entity of the supply chain a strand displacing polymerase, dNTPs, a first nanoparticle linked to a first authentication strand, and a second nanoparticle linked to a second authentication strand, wherein the tag binds to the first authentication strand, wherein in solution the tag, strand displacing polymerase, dNTPs, first authentication strand, and second authentication strand react to form a double stranded molecule comprising the first and second nanoparticle to produce a color change in the solution.

In some embodiments, the authentication methods comprise: contacting a product of interest with a tag at a first stage of a supply chain; optionally removing the tag from the product of interest at a second stage of the supply chain; and combining the tag with a solution comprising a strand displacing polymerase, dNTPs, a first nanoparticle linked to a first authentication strand, and a second nanoparticle linked to a second authentication strand, wherein the tag binds to the first authentication strand, and wherein in solution the tag, strand displacing polymerase, dNTPs, first authentication strand, and second authentication strand react to form a double stranded molecule comprising the first and second nanoparticle to produce a color change in the solution.

In other embodiments, the authentication methods comprise: combining, in a solution, a tag, a strand displacing polymerase, dNTPs, a first nanoparticle linked to a first authentication strand, and a second nanoparticle linked to a second authentication strand; and producing form a double stranded molecule comprising the first and second nanoparticle to produce a color change in the solution.

Other aspects of the present disclosure comprise compositions and/or kits comprising the tag and authentication strands described herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIG. 1A shows tag sequences that are specific to different items and are incorporated directly into products for future identification. FIG. 1B shows tags that are specific to groups of items, such as specific batches or items from the same time period that are labeled with the same tag sequences.

FIG. 2A shows a method of using toehold exchange to create one or more reversible strand displacement cascades. FIG. 2B shows an example of biasing a reversible strand displacement cascade towards a specific equilibrium state by using a concentration of the displacement strand that is higher than a concentration of the fluorophore (F)/quencher (Q) complex and the tag strand which may enable the tag to act catalytically to permit the system to reach the equilibrium. FIG. 2C shows an alternative example of biasing a reversible strand displacement cascade with the fluorophore (F) and quencher (Q) positions swapped on the strands, which may enable the tag to act catalytically to promote an ON state equilibrium.

FIG. 3A shows the use of labels comprising DNA tags embedded in the surface to secure products by allowing authentication of products and packaging. FIG. 3B shows an example method for using one-time use labels that includes application of an authenticator solution and a visually detectable authentication signal (e.g., an increase in fluorescence or a color change for the correct tag/authenticating identifier pair) before the label is discarded. FIG. 3C shows an example method for using a re-usable label that may be authenticated multiple times and includes a wash step to wash away additional oligos and buffers that may have attached to the surface as a result of the authentication chemistry.

FIG. 4A shows an example label comprising tags that are embedded into the label by directly drying, or freeze-drying, the oligos onto the surface. FIG. 4B shows an example label comprising tags (e.g., oligo strands) that are attached to nanoparticles or other moieties that are unlikely to move once associated with a surface. FIG. 4C shows an example label comprising tags (e.g., oligo strands) that are attached to a surface by other chemistries, such as through the use of biotinylated oligos that bind strongly to streptavidin on the surface. FIG. 4D shows an example label comprising tags (e.g., oligos strands) that are protected by a protective coating applied to the label. FIG. 4E shows an example label comprising tags (e.g., oligo strands) that are embedded in a gel matrix rather than bound to the surface of a label.

FIG. 5A shows a supply chain authentication workflow comprising tags, in the form of a label or other formulation, that are provided to a manufacturer and applied to the product or packaging of the product to be secured and authenticating identifiers, such as in solution form, that are provided to customers, who can then authenticate the labels upon receiving the product. FIG. 5B shows a supply chain using one or multiple tags that are applied to a part, product, or packaging by a supplier and subsequently authenticated at each step in the supply chain. FIG. 5C shows a supply chain using tags that are applied at different stages of the supply chain and are authenticated at the end of the chain by the customer. FIG. 5D shows a supply chain that, at each step, previously applied tags may be authenticated in addition to appending new tags to products in another variants of the workflow.

FIG. 6A shows a label comprising a tag substance and structure that is repeated on one or more larger labels. FIG. 6B shows a label that permits multiple readouts and washes. FIG. 6C shows a label comprising DNA tags embedded in a soluble wax or other soluble solid that enables a sample to be taken from the label by scratching the label.

FIG. 7A shows the introduction of hairpins to each step of a supply chain pathway. FIG. 7B shows the combining of hairpins with a primer, strand displacing polymerase, and dNTPs in a canonical Primer Exchange Reaction (PER). FIG. 7C shows a PER pathway that uses the three hairpins A, B, and C to produce a four-domain sequence that may be authenticated using any of the previously described chemistries.

FIG. 8A shows the introduction of tags (e.g., oligos) to the steps along a supply chain pathway. FIG. 8B shows an authenticator complex with a quenched fluorophore (OFF) can be used to validate that tags have been added to each step. FIG. 8C shows the use of toehold exchange to generate a cascade to verify the presence of each tag through generation of a fluorescent signal.

FIG. 9A shows specific tag that are introduced to a product at different points along a supply chain. FIG. 9B shows that, at the end of the supply chain, products can be verified to have passed through each of the supply chain steps by using a ligation procedure.

FIGS. 10A-10C illustrate methods for plant product authentication. FIG. 10A shows containers comprising unique tags that may be provided to different producers, distributors, or other actors. FIG. 10B shows application of the tags by spraying the tags onto the product (e.g., produce). FIG. 10C shows multiple products that may be re-packaged such that the tag sequences may remain with the plant products and can be recovered using any of the authentication procedures described herein.

FIG. 11A shows items that are labeled with three unique tags, denoted as a, b, and c. FIG. 11B shows unique tag sequences that share one or more common sequence components, such as flanking sequences on either or both sides of unique tag sequences that may serve as primer binding sites for amplification. FIG. 11C shows that items may contain identical (or no) tag sequences between unique pairs of flanking sequences that may enable a unique pair of amplification primers to amplify a select sequence. FIG. 11D shows that different items may contain unique flanking sequences on either or both sides of unique tag sequences.

FIG. 12A shows primers that are combined with tag sequences to permit amplification (e.g., using polymerase chain reaction (PCR) and thermal cycling) of the tags. FIG. 12B shows amplification of double-stranded tags. FIG. 12C shows ligation of tags without flanking sequences. FIG. 12D shows ligation of tags with flanking sequences.

FIG. 13A shows the use of unsequenceable oligos (e.g., tags and/or authenticating identifiers) for anti-counterfeiting measures. FIG. 13B shows the use of excess oligos for anti-counterfeiting measures. FIG. 13C shows the use of dynamic and environmental tag modifications for anti-counterfeiting measures. FIG. 13D shows the use of various constraints for anti-counterfeiting measures.

FIG. 15A shows example methods for applying identity ink. FIG. 15B shows distribution of unique and group identity ink materials. FIG. 15C shows an example hierarchical organization structure for identity ink distribution.

FIGS. 16A-16D illustrate examples of universal authentication methods for the detection of multiple unique tags. FIG. 16A shows an example of sixteen unique tag sequences. FIG. 16B shows example universal authenticators that may be used to verify each unique tag. FIG. 6C shows example detection methods for the sixteen unique tags. FIG. 16D shows example binary strings that may be generated from the presence or absence of each tag of the sixteen unique tags.

FIG. 24A shows an authorization method that generates a diffuse visible pigment that expands radially across a label upon authentication of a product. FIG. 24B shows an authorization method that generates a diffuse visible pigment that expands linearly across a label upon authentication of a product.

FIG. 27A shows a detection scheme uses hybridization of an enzyme bound oligo.
FIG. 27B shows a detection scheme that uses displacement of an enzyme bound oligo.
FIG. 27C shows a detection scheme that uses a positive and negative control.
FIG. 27D shows a pigment based authentication method.
FIG. 27E shows a pigment based authentication method that uses a positive and negative control.

FIG. 28A shows nanoparticle aggregation due to hybridization of the authenticating identifier with the tag.

FIG. 28B shows nanoparticle aggregation due to catalytic contributions from the authenticating identifier. FIG. 28C shows nanoparticle separation due to hybridization of the authenticating identifier with the tag. FIG. 28D shows nanoparticle separation due to displacement caused by the authenticating identifier. FIG. 28E shows nanoparticle separation due to displacement caused by an additional tag.

FIG. 29A shows a schematic of nanoparticle separation due to hybridization of the authenticating identifier. FIG. 29B shows an experimental color change due to authentication.

FIG. 30A shows polymerization-based concatemerization. FIG. 30B shows using polymerization-based concatemerization for nanoparticle aggregation. FIG. 30C shows hybridization-based concatemerization. FIG. 30D shows using hybridization-based concatemerization for nanoparticle aggregation.

FIG. 32A shows an authenticating identifier that enables displacement of a hybridized tag. FIG. 32B shows an authenticating identifier that enables displacement of hybridized tag through a branch migration reaction.

FIG. 33A shows a split-protein colorimetric system. FIG. 33B shows a protein-substrate colorimetric system.

DETAILED DESCRIPTION

Figure 1A:
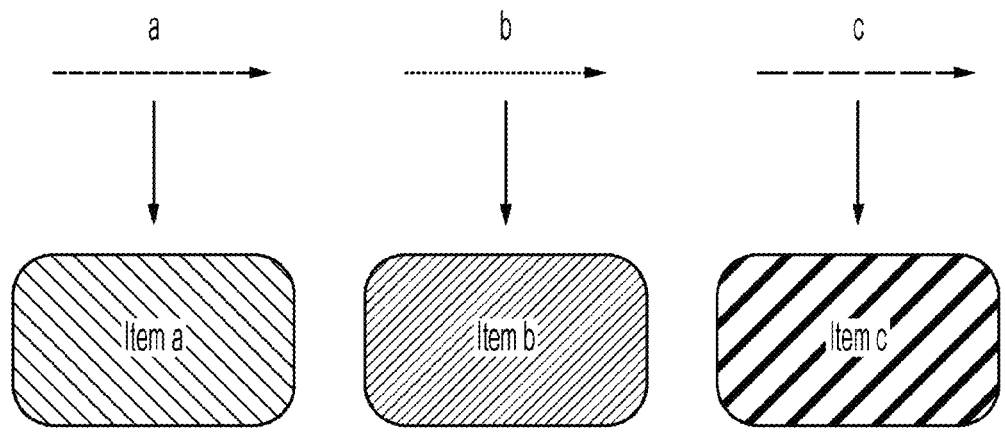
FIGS. 1A and 1B illustrate example tagging strategies.

As used herein, the term "authentic" generally describes an item that is of undisputed origin or, in other words, genuine. In the context of articles and products described herein, an authentic article or product can be of undisputed origin with respect to the producer, supplier or retailer of the article or product. Producers can be any relevant individual, subject, entity, manufacturing location, or party including examples types of subjects, entities or parties described herein. For example, an "authentic" Tiffany & Co. necklace can refer to a necklace for which it is undisputed that Tiffany & Co. is the actual producer (either directly, or indirectly via a contract manufacturing organization, subsidiary, etc.) of the necklace. In another example, an "authentic" will from a testator can refer to an original or copy of a will actually generated or signed by the testator.

As used herein, the term "authenticity" generally refers to a measure of whether or not an item is "authentic". An item having authenticity is indeed authentic, whereas an item lacking authenticity is not authentic and may be counterfeit, illegally produced or produced from a source other than presented. Moreover, an "authenticable" object generally refers to an object for which its authenticity can be determined.

As used herein, the term "tag" generally refers to a species that comprises an identifier that can be associated with a particular object and that identifies a property of that object. For example, a tag may comprise one or more nucleic acid molecules that comprises a unique nucleotide sequence. This tag can be applied to an object (e.g., a product or article) so that the unique sequence is associated with a property of the object. In some embodiments, the unique sequence is associated with the origin of the object. In general, the identifier, such as a unique nucleotide sequence, can be detected either directly or indirectly by observing a signal associated with a reaction or other interaction involving the tag.

As used herein, the term "authenticating identifier" generally refers to a species or a test substrate that includes a species (e.g., nucleic acid strands) that can interact (e.g., react with, bind with, displace, compete with, substitute with, etc.) with a tag to generate a detectable signal. The detectable signal can be detected and used to confirm presence of the tag. In some embodiments, an authenticating identifier comprises one or more nucleic acid molecules that can interact with a tag. Where the tag itself comprises a nucleic acid molecule, the authenticating identifier can hybridize or bind in any other way to the tag such that a detectable signal is generated. As used herein, the term "test substrate" generally refers to a wicking material that includes components that can interact (e.g., react with, bind with, displace, compete with, substitute with, etc.) with a tag to generate a detectable signal.

As used herein, the term "binding specificity" generally refers to a species that uniquely binds to a particular species such as, for example, in sequence specific fashion. For example, a tag may comprise a nucleic acid sequence and an authenticating identifier may comprise a complementary sequence to the nucleic acid sequence of the tag. As the authenticating identifier has a sequence that binds in sequence specific fashion to the tag, it can be considered to have binding specificity for the tag. Moreover, a species that does not have binding specificity generally refers to a species that does not readily and uniquely bind to another species, such as, for example, in sequence specific fashion because, for example, the species lacks a sequence corresponding to a sequence of the additional species. For example, a tag may comprise a nucleic acid sequence and an authenticating identifier may not include a sequence that is complementary to the nucleic acid sequence. As the authenticating identifier does not have a sequence that can bind to the tag in sequence specific fashion, it can be considered not to have binding specificity for the tag.

As used herein, the term "docking strand" generally refers to a single-stranded nucleic acid that is 200 nucleotides or fewer in length. In some embodiments, a docking strand is 100 nucleotides or fewer. In some embodiments, a docking strand is 50 nucleotides of fewer. In some embodiments, a docking strand binds to an imager strand. In some embodiments, a docking strand is DNA or RNA.

As used herein, the term "imager strand" generally refers to a single-strand nucleic acid that is complementary to (and binds to) a docking strand. In some embodiments, an imager strand is a signal-generating imager strand, meaning that a detectable signal is generating upon binding of an imager strand to a docking strand. In some embodiments, an imager strand is linked to a detectable moiety, such as a fluorophore, quantum dot, or nanoparticle.

As used herein, the term "molecular complex" generally refers to an agglomeration of a plurality of molecules. The molecules can be any molecules that can complex together. In some embodiments, a molecular complex is an agglomeration of a plurality of nucleic acid molecules. In such cases, one or more of the plurality of nucleic acid molecules may be associated with a non-nucleic acid species, such as an enzyme or other detectable agent (e.g., a dye, a pigment, a fluorophore, an optically-active agent, etc.).

As used herein, the terms "nucleic acid" and "nucleic acid molecule" may be used interchangeably and generally refer to a polymeric form of nucleotides of any length, either deoxyribonucleotides (dNTPs) or ribonucleotides (rNTPs), or analogs thereof. Nucleic acids may have any three dimensional structure, and may perform any function, known or unknown. Non-limiting examples of nucleic acids include deoxyribonucleic acids (DNA), ribonucleic acids (RNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components.

As used herein, a nucleic acid brick nanostructure may be a nucleic acid nanostructure that is formed by single-stranded tile-based (SST-based) methods. SST-based methods may be used, for example, to generate larger repetitive nucleic acid crystal assemblies. SST-based methods involve the use of short unique single-stranded tiles (SSTs) capable of self-assembling into a selected pattern or shape.

As used herein, a nucleic acid nanostructure (also referred to as nanostructure) may be a two-dimensional or three-dimensional nanostructure made from (e.g., self-assembles from) nucleic acids (e.g., DNA, RNA, lock nucleic acids (LNA), peptide nucleic acids (PNA), or any combination thereof). It should be understood that neither a single-stranded nucleic acid nor a double-stranded nucleic acid (e.g., a DNA double helix) is considered a "nanostructure." Nucleic acid nanostructures, in some embodiments, serve as scaffolds for the formation of more complex structures, e.g., molecular complexes. In some embodiments, a nucleic acid nanostructure is a DNA origami structure that is assembled using a DNA origami method (see, e.g. Rothemund, P. W. K. Nature 440, pages 297-302, 2006). In some embodiments, a nucleic acid nanostructure is a DNA brick structure that is assembled using a SST-based method, (see, e.g., Ke, Y. et al. Science. 338(6111), 2012; Wei B. et al. Nature 485: 626, 2012; International Publication Number WO 2014/074597, published 15 May 2014; International Publication Number WO 2013/022694, published Feb. 14, 2013; and International Publication Number WO 2014/018675, published Jan. 30, 2014, each of which is incorporated by reference herein). In some embodiments, a nucleic acid nanostructure is assembled through folding of a single strand of nucleic acid as described, for example, in WO 2016/144755, incorporated herein by reference. A nucleic acid nanostructure may form a recognizable shape, such as a letter of the alphabet, a sheet, a rod, a square block, a capsule, etc. as described, for example, in WO 2014/018675.

As used herein, a nucleic acid origami nanostructure may refer to a nucleic acid nanostructure that is formed by assembling two or more 'staple strands' with one or more 'scaffold' strands into a prescribed shape. Staple strands are typically short (e.g., 200 nucleotides or shorter) nucleic acid strands (single-stranded nucleic acids); scaffold strands are typically longer (e.g., longer than 200 nucleotides) nucleic acid strands (single-stranded nucleic acids). A nucleic acid origami nanostructure may be a DNA origami nanostructure. DNA origami nanostructures can be folded, e.g., through self-assembly, into discrete and unique geometric patterns, e.g., two-dimensional (2D) and three-dimensional (3D) shapes, which may be further self-assembled to create larger nanostructures or microstructures comprising two or more discrete origami nanostructures. In some embodiments, a scaffold strand has a sequence derived from M13 bacteriophage. Other scaffolds strands may be used. In some embodiments, a staple strand is a fluorophore-labeled staple strand. In some embodiments, the staple strand is 4 to 30 nucleotides (e.g., 4, 5, 6, 7, 8, 9, 10, 11, 12, 13, 14, 15, 16, 17, 18, 19, 20, 21, 22, 23, 24, 25, 26, 27, 28, 29, or 30 nucleotides) in length. In some embodiments, the staple strand stably binds (for longer than 10 seconds) to a scaffold strand, for example, at room temperature. In some embodiments, the staple strand is longer than 30 nucleotides in length.

As used herein, a shape may be any recognizably distinct image, structure, or design. A shape, in some embodiments, is a geometric shape, such as a square, circle, or triangle. A shape, in some embodiments, is formed from a pattern, which contains repeating elements. A pattern may contain arbitrary elements. In some embodiments, a pattern is asymmetrical. In some embodiments, a pattern is symmetrical.

As used herein, a plurality is any number or value greater than one. A plurality may be at least 2, at least 3, at least 5, at least 10, at least 20, at least 25, at least 30, at least 40, at least 50, at least 100, at least 150, at least 200, at least 250, at least 300, at least 350, at least 400, at least 500, or at least 1,000. A plurality of nucleic acids such as a plurality of nucleic acid staple strands or a plurality of SSTs may comprise at least 2, at least 3, at least 5, at least 10, at least 20, at least 25, at least 30, at least 40, at least 50, at least 100, at least 150, at least 200, at least 250, at least 300, at least 350, at least 400, at least 500, or at least 1,000 nucleic acids. In some embodiments, a plurality of nucleic acids includes 2-1000, 5-1000, 10-1000, 50-1000, 100-1000, or 500-1000 nucleic acids. In some embodiments, a plurality of nucleic acids includes 2-5000, 5-5000, 10-5000, 50-5000, 100-5000, or 500-5000 nucleic acids.

As used herein, the term "sequence complementarity" generally refers to a property of a pair of nucleic acid molecules, where each nucleic acid molecule has a sequence that is complementary to a sequence of the other nucleic acid molecule. The complementary sequences of the pair of nucleic acid molecules can hybridize with each other, including via Watson-Crick base-pairing.

As used herein, the term "supply chain" generally refers to a system of organizations, people, activities, information and resources involved in moving a product from supplier (or manufacturer) to a customer. Various parties can be a part of a supply chain including a manufacturer or supplier, a distributor, a retailer and personnel of these entities. A supply chain can also include entities that contract with one or more of these entities to effect movement of a product from manufacture to the end customer. An example of such an entity is a contract manufacturing organization (a CMO). In general, the "upstream" portion of a supply chain refers to a direction moving away from the customer and toward the manufacturer. For example, a distributor is "upstream" in the supply chain from the customer. Also, in general, the "downstream" portion of a supply chain refers to a direction moving toward the customer. For example, a customer is "downstream" from a distributor.

As used herein, the term "tag" generally refers to a species that comprises an identifier that can be associated with a particular object and that identifies a property of that object. For example, a tag may comprise one or more nucleic acid molecules that comprises a unique nucleotide sequence. This tag can be applied to an object (e.g., a product or article) so that the unique sequence is associated with a property of the object. In some embodiments, the unique sequence is associated with the origin of the object. In general, the identifier, such as a unique nucleotide sequence, can be detected either directly or indirectly by observing a signal associated with a reaction or other interaction involving the tag.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Molecular Authentication Tags

Molecular authentication methods of the present disclosure, in some embodiments, comprise distributing to a first entity of a supply chain a tag comprising a first strand that uniquely identifies a product of interest, and distributing to at least one additional entity an authenticating identifier composition comprising a second strand that binds to the first strand, wherein binding of the second strand to the first strand produces a detectable signal. Molecular authentication methods herein also comprise contacting a product of interest at one step of a supply chain with a tag, wherein the tag comprises a first strand that uniquely identifies the product of interest, and combining the first strand of the tag with an authenticating identifier composition that comprises a second strand, wherein the second strand comprises a domain that binds to the first strand, and wherein binding of the second strand to the first strand produces a detectable signal. A domain may be a particular sequence within a nucleic acid. In some embodiments, a domains are used to describe regions of a nucleic acid that bind to (hybridize to) each other (e.g., includes sequence complementary to each other). For example, domain a of a tag typically binds to domain a* of an authenticating identifier strand.

Figure 7A:
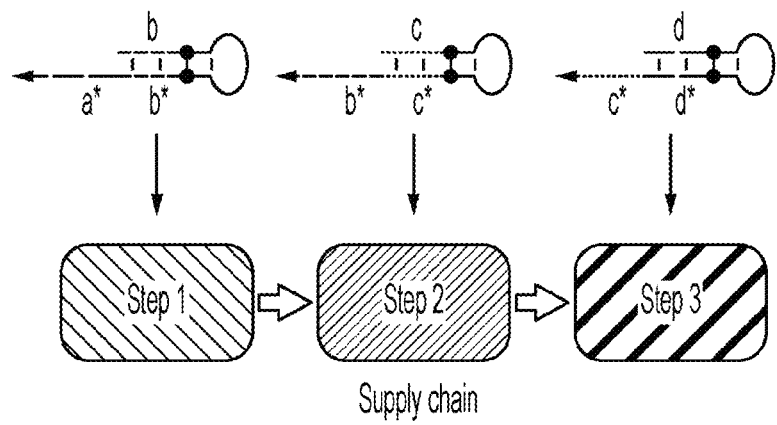
FIGS. 7A-7C illustrate example authentication methods using hairpins.
Figure 8A:
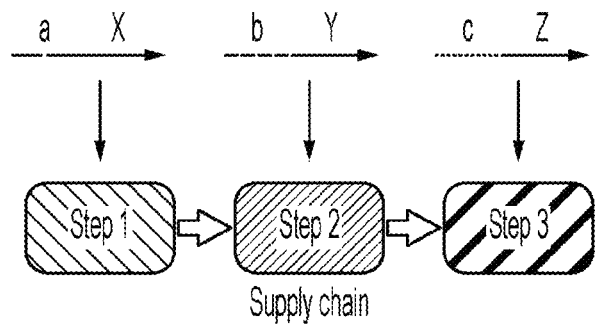
FIGS. 8A-8C illustrate a method of toehold exchange-based supply chain authentication.

A tag, as provided herein and implemented in methods and products/materials described herein, may be a linear nucleic acid (single-stranded or double-stranded), with examples depicted in FIG. 8A, or a hairpin, as depicted in FIG. 7A. The length of a tag may vary, although as described herein, there are several advantages of using tags having a length of shorter than 50 nucleotides, or even shorter than 30 nucleotides. Thus, in some embodiments, the length of a tag is shorter than 45, 40, 35, 30, 25, 20, or 15 nucleotides. In some embodiments, the length of a tag is 10-50, 10-45, 10-40, 10-35, 10-30, 10-25, or 10-20 nucleotides. In some embodiments, the length of a tag is 10, 15, 20, 25, 30, 25, 40, 45, or 50 nucleotides. Moreover, In some embodiments, a tag comprises a plurality of nucleic acid molecules. In such cases, a tag may comprise at least about 2, 3, 4, 5, 6, 7, 8, 9, 10, 11, 12, 13, 14, 15, 20, 25, 30 or more nucleic acid molecules.

Tags, as described herein, are used to uniquely barcode individual products or product batches. The tags (strands) may be applied to or embedded in a product of interest. In some embodiments, the barcodes strands are components of a product of interest. For example, liquid products, such as ink or perfume, may include tags in the product solution. Tags that are applied to a product may be later removed, formulated in a solution, and applied to an application region of a test substrate for product authentication. In some embodiments, barcodes strands are formulated in water or buffer (e.g., TE) with or without additives that improve nucleic acid stability and adhesive/binding properties.

In some embodiments, a tag may be a nucleic acid nanostructure including nucleic acid origami nanostructures (e.g., DNA origami nanostructures) and nucleic acid brick nanostructures (e.g., DNA brick nanostructures). Both DNA origami and DNA brick nanostructures can incorporate unique and identifiable features along the peripheries of the structures by the extension of the staple or brick strands to create overhangs protruding from the structure. These overhangs can have specific, programmable sequences and would not be visible or detectable without specific knowledge of their sequence composition and can be used as binding sites for specific molecular barcode strands that reveal their positioning to create an authenticable pattern.

Figure 1B:
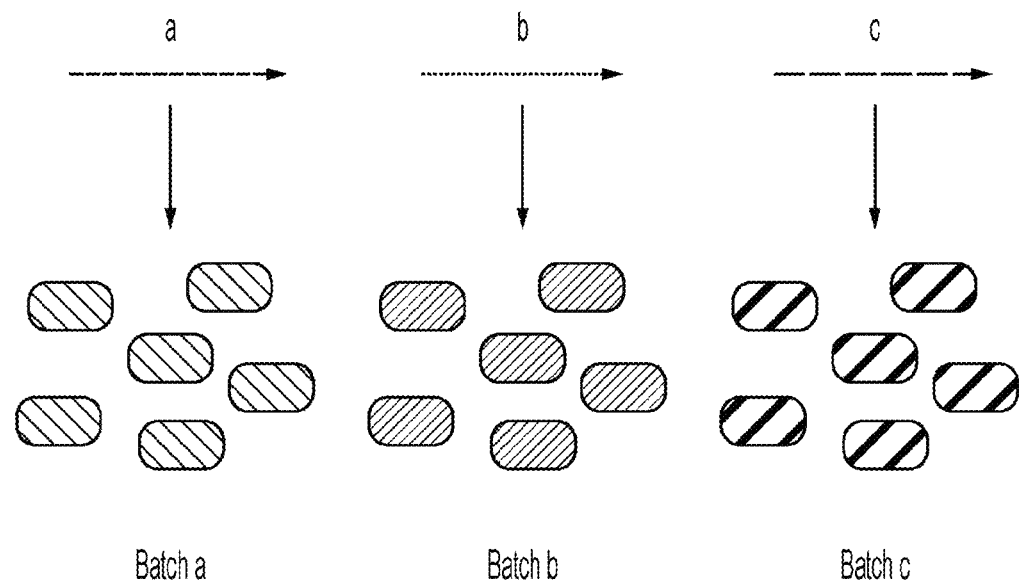

A tag may be intended to uniquely identify an entity (e.g., a product, a batch/lot of products, a company, or an entity in a supply chain, such as a manufacturer, supplier, producer, distributor, or seller) or step of a supply chain. Thus, it should be understood that a unique tag may be associated with only one entity such that the entity may be identified simply by the presence of the tag (e.g., attached to a product or embedded in a product). A tag may be used to barcode an object or an entity. The general concept of "tagging" may be used herein to distinguish one entity from another entity. FIGS. 1A and 1B illustrate example tagging strategies. FIG. 1A shows tag sequences that are specific to different items and are incorporated directly into products for future identification; FIG. 1B shows tags that are specific to groups or batches of items. Tags may be unique between different products or may be conserved between different or products. For example, specific product batches may have tags that are the same within the batch and unique between different batches. A batch may indicate a manufacture lot and each product within the manufacture lot may comprise the same tag. The tag may be used to distinguish and authenticate the different manufacture lots.

Figure 3A:
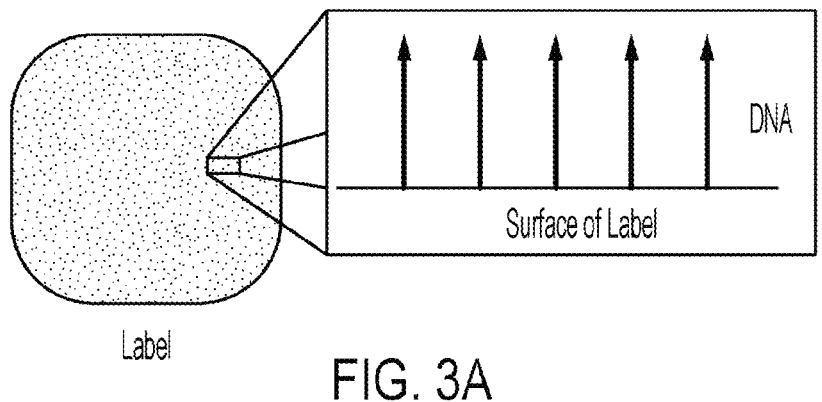
FIGS. 3A-3C illustrate example DNA tagged labels.
Figure 3B:
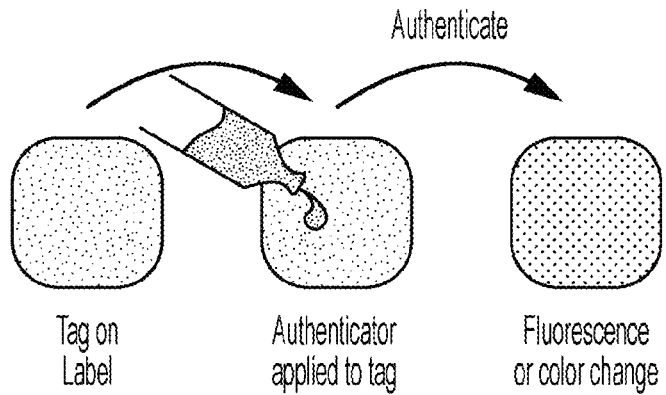
Figure 3C:
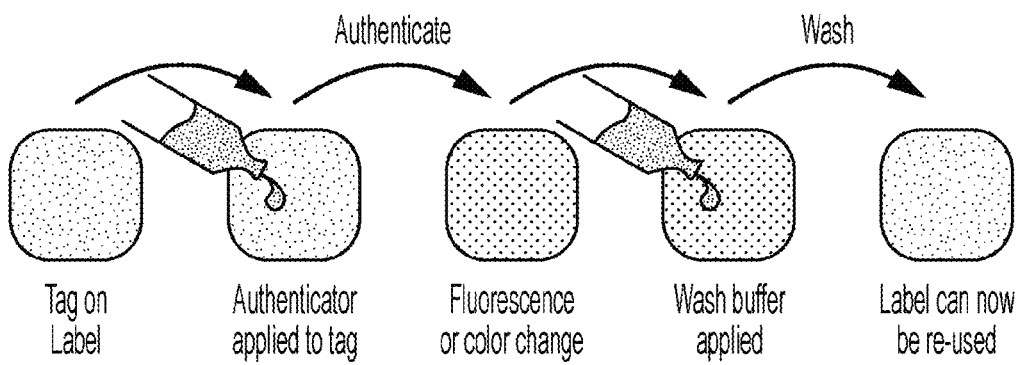

The tag, in some embodiments, may comprise one or more nucleic acid molecules provided on (attached to) a surface of a label (e.g., sticker or other object that can be attached to products and/or packaging), for example, as shown in FIGS. 3A-3C. FIG. 3A shows a label with one or more nucleic acid (e.g., DNA) tags embedded in the surface. The label may be used to secure products my allowing authentication of products and packaging. This label may be referred to herein as a tag. An authenticating identifier (also referred to in the Figures as an authenticator composition), can be applied to the label, and if the label contains the correct tag oligoes or strands, then the label exhibits a color change. The label may be a one-time use label or the label may be re-used. FIG. 3B shows a one-time use label. Authentication of a one-time use label may include application of the authenticating identifier applied to the label that results in a detectable (e.g., visually or electronically) signal. The label may be discarded after authentication is verified and the signal is detected. Alternatively, or in addition to, the label may be saved (e.g., physically or digitally) as a record of authentication. FIG. 3C shows a multi-use or re-usable label that may be authenticated multiple times. The authentication process may be followed by the application of a wash buffer to remove the previously-applied authenticating identifier. The wash buffer may contain low salt or formamide to promote displacement. Pure water may also be used to de-hybridize strands from the tags attached to the surface of a label. Other methods may also be used to facilitate de-hybridization.

Tags, in some embodiments, bind within a source region to test strands and detectably-labeled strands (see, e.g., FIG. 27A) or to bridge strands, thereby displacing them from detectably-labeled strands and source strands. (see, e.g., FIG. 27B). Thus, in some embodiments, barcodes strands comprise a domain that binds to (e.g., is complementary to) test strands and a domain that binds to detectably-labeled strands. In other embodiments, barcodes strands comprise a domain that binds to bridge strands. The binding domains of a tag may be partially complementary to (less than 100% complementary) or wholly complementary to (100% complementary to) a test strand, detectably-labeled strand, or bridge strands (or other strands to which the domain is designed to bind).

A tag, as provided herein and implemented in methods and products/materials described herein, may be a linear nucleic acid (single-stranded or double-stranded). The length of a tag may vary, although as described herein, there are several advantages of using tags having a length of shorter than 50 nucleotides, or even shorter than 30 nucleotides. Thus, in some embodiments, the length of a tag is shorter than 45, 40, 35, 30, 25, 20, or 15 nucleotides. In some embodiments, the length of a tag is 10-50, 10-45, 10-40, 10-35, 10-30, 10-25, or 10-20 nucleotides. In some embodiments, the length of a tag is 10, 15, 20, 25, 30, 25, 40, 45, or 50 nucleotides. In other embodiments, the length of a tag is longer than 50 nucleotides.

Figure 4A:
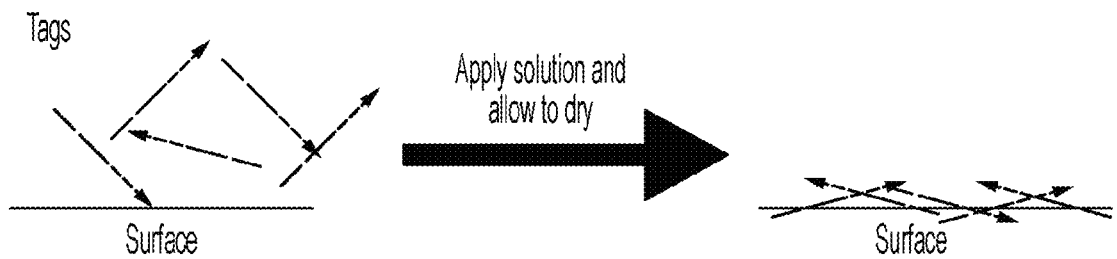
FIGS. 4A-4E illustrate example labels comprising tags.
Figure 4B:
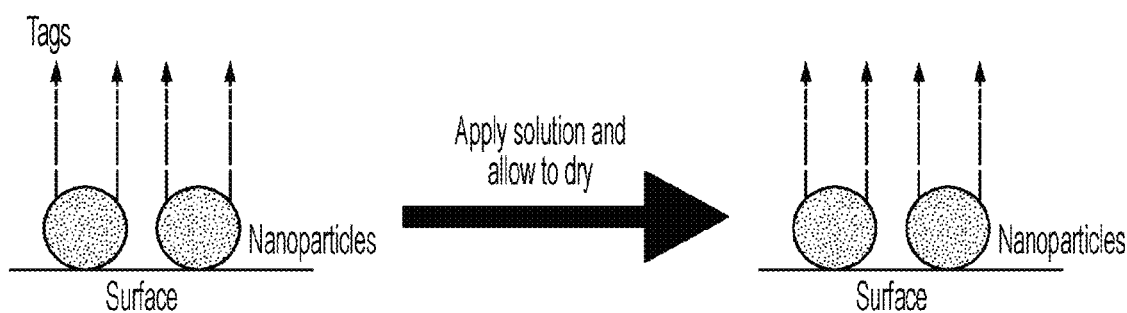
Figure 4C:
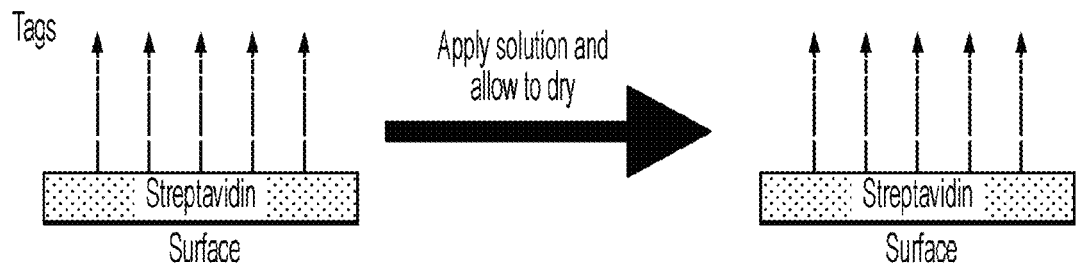
Figure 4D:
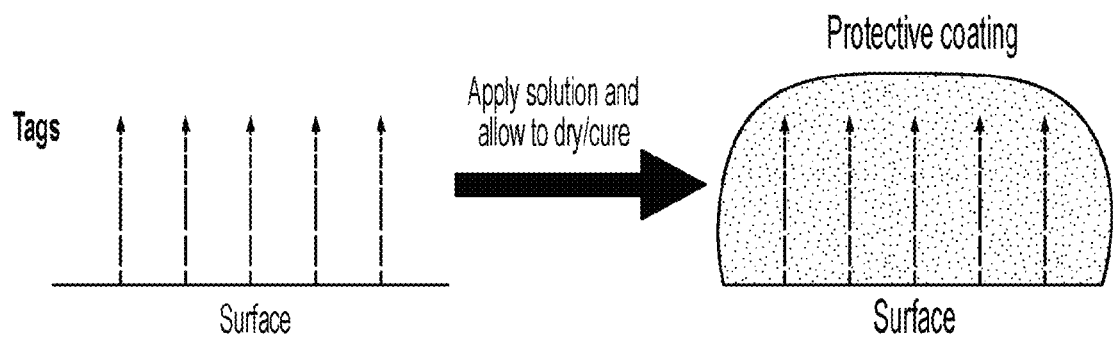
Figure 4E:
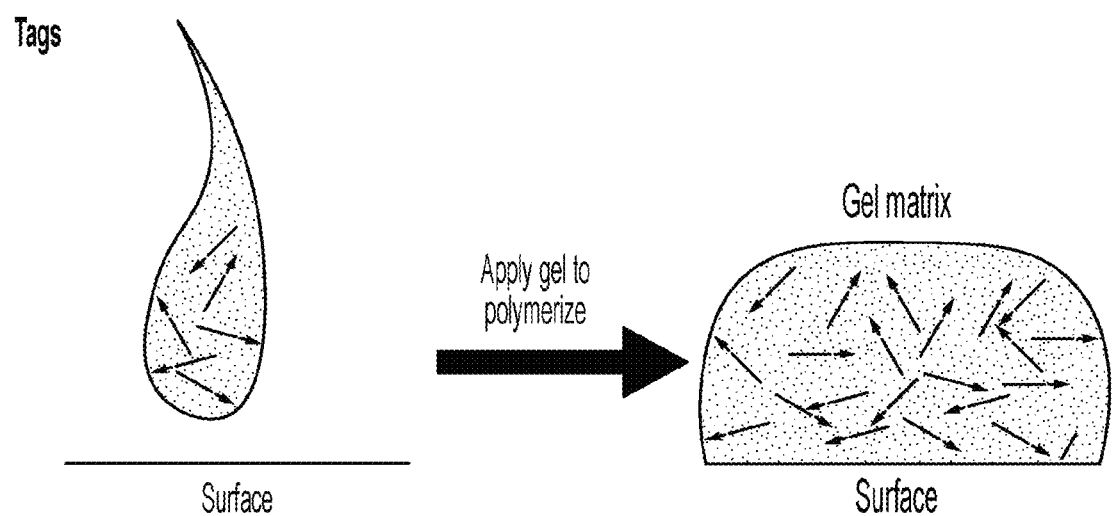
Figure 6A:
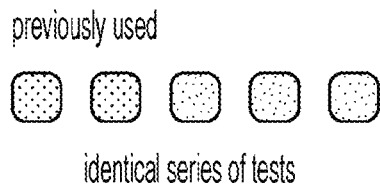
FIGS. 6A-6C illustrate examples of methods of molecular authentication.
Figure 6B:
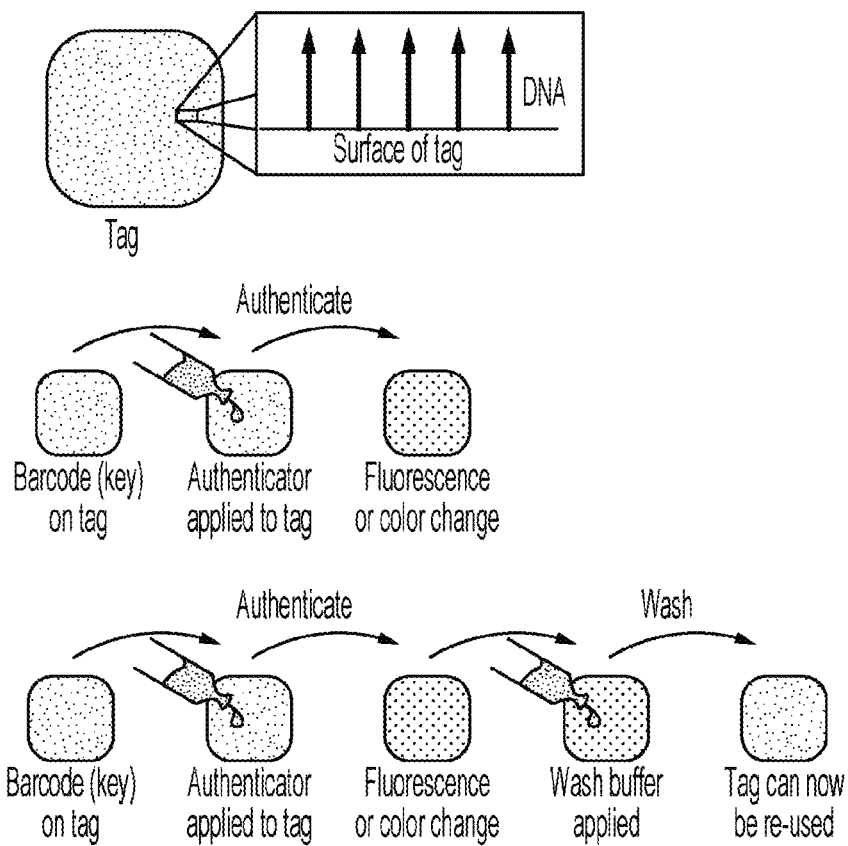
Figure 6C:
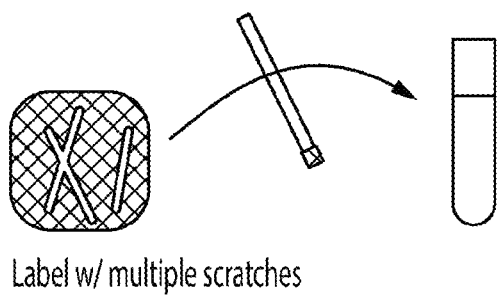

Any suitable strategy, including various chemistries, may be used to attach or embed the tag to the surface of the label (or even onto an article directly). In general, an article to be associated with a tag may be admixed with the tag. As used herein, the term "admixing" generally refers to bringing two separate objects or materials into contact with one another. In some embodiments, admixing two objects or materials together can generate a mixture or suspension comprising the two objects. In some embodiments, admixing two objects or materials with one another can result in one object being attached to or embedded in the other object or a layer of or affixed to the other object. Admixing may attach or embed to the article or may embed the tag into the article (e.g., embedded in a layer attached to the article). FIGS. 4A-4E provide several non-limiting examples. In one embodiment, the tag(s) are dried or freeze-dried to the surface of the label (FIG. 4A). The tags may be randomly dried on the surface or may be provided in a pattern (e.g., using electrostatic interactions or printing processes) and dried to the surface. In another embodiment, the tag(s) are linked to a nanoparticle, which may be immobilized on the label (FIG. 4B). The tags may be linked to the nanoparticle using covalent and/or non-covalent interactions. Covalent interactions may include providing a linker on the surface of the particle and coupling the tag to the linker. The linker may include a polymer based linker. The linker may be a zero-length linker (e.g., couple the tag directly to the bead) or may be a linker that spaces the tag out from the surface of the nanoparticle. Non-covalent interactions that couple the tag to the nanoparticle may include hydrophobic/hydrophilic interactions, electrostatic interactions, and hydrogen bonding. The surface of the nanoparticle may or may not be coated with a material to facilitate non-covalent interactions between the nanoparticle and the tag. In yet another embodiment, a protein-protein binding pair, such as biotin and streptavidin, is used to link the tag(s) to the surface of the label (FIG. 4C). The tags may comprise a biotin tag and the surface may comprise streptavidin. The tag(s), in some embodiments, are coated with a protective coating on the surface of the label (FIG. 4D), and/or embedded in a gel matrix (e.g., polyacrylamide or agarose gel) on the surface of the label (FIG. 4E). The tag may be added to the surface prior to the addition of the gel matrix. Alternatively, or in addition to, the tag may be mixed into the gel matrix prior to addition to the surface of the label. The label itself may be further contained within a plastic seal or other covering that allows the humidity to be controlled and/or protects the tag nucleic acid molecules (e.g., tag strands) from exposure to environmental conditions. In still another embodiment, the tag(s) are embedded in a soluble wax such that they may be scratched off the tag or product and, for example, dropped into a testing vial containing an authenticating identifier (FIG. 6C).

In some embodiments, admixing can yield a mixture or solution comprising a tag and a article. For example, where the article is a liquid, solid or liquid form tag can be added to the article and a mixture generated. In some embodiments, a solution results such that when an authenticating identifier binds with the tag, a detectable signal results.

Products of interest and/or labels are often contacted with tag(s). The term "contacting" refers to applying the tag(s) in any number of ways. The tag(s), in some embodiments, are formulated as a spray solution or an ink solution. In some embodiments, the tag(s) are formulated as a liquid and administered using a dropper/pipette. Drying the tag(s) on a product, in some embodiments, renders the nucleic acid more stable. Tag(s) may also be dried before introduction to a product, and then either dissolved in liquid products or spread onto the product.

Tags, in some embodiments, may be formulated in water or buffer (e.g., TE), with or without additives that improve nucleic acid stability and adhesive/binding properties.

Labels may be designed to be used multiple times, enabling multiple examinations of the same tag(s) along a supply chain, a product to be passed along (e.g., sold) to another customer, or other transfer. FIGS. 6A-6C illustrate example processes for repeating authentication of a single product. FIG. 6A shows a label comprising repeated surface areas and/or geometries that create a multiuse label. Each surface area or geometry may comprise the same tag which may be authenticated using the same authenticating identifier. Alternatively, or in addition to, each surface area or geometry may comprise a different tag to allow for the use of personalized or customized authenticating identifiers. Each user (e.g., member of the supply chain or customer) may use a single surface area or geometry to verify authenticity. In other embodiments, the authenticating identifier may be washed away leaving a 'clean' label (FIG. 6B). In still other embodiments, the label contains tag(s) embedded in a protective wax or other removable material. A small sample of the wax or material may be removed (e.g., scratched off) and added to a test vial for analysis (FIG. 6C). The scratched-off sample may be tested in a liquid test vial, e.g., containing the authenticating identifier. The label may allow authentications to be performed until all of the wax or removable material containing the tag is removed from the label.

The nucleic acids used herein (either as tags or authenticating identifiers) may be modified to prevent them from being successfully sequenced. Thus, in some embodiments, a tag (or authenticating identifier) may include enantiomers of DNA, backbone modifications, covalent modifications to bases that may or may not change their hybridization behavior, and/or unnatural base pairs (e.g., iso-C and iso-G). In some embodiments, the tag (or authenticating identifier) length, sequence, other variable that affects hybridization strength, may be varied. In some embodiments, one or more dummy sequence(s) that do not participate in a reaction may be present to make reverse-engineering difficult.

In some embodiments, sequences for pools of tags can all be recovered independently with usage of distinct PCR primers or together with the same primers, e.g., with next generation sequencing (NGS). NGS using UMI's may be used to recover quantitative population data for embodiments where tags or authenticating identifiers are expected to be at specific relative concentrations.

In some embodiments, a tag "sequence" may refer to a population of sequences with a particular pattern. For example, during synthesis, some specific base positions may incorporate random bases (by including all four possible phosphoramidites at a specific synthesis step, for example). The distribution of possible bases at a particular base location may be further controlled (biased) by including the phosphoramidites at different relative concentrations (e.g. a base may be given a 75% chance to be an 'A' base and a 25% chance to be a 'T'). This bias information may be used to further authenticate a tag (e.g., tag sequence) (pool) through the use of a quantitative NGS method to verify that the proper distribution of strand sequences is present.

Figure 13A:
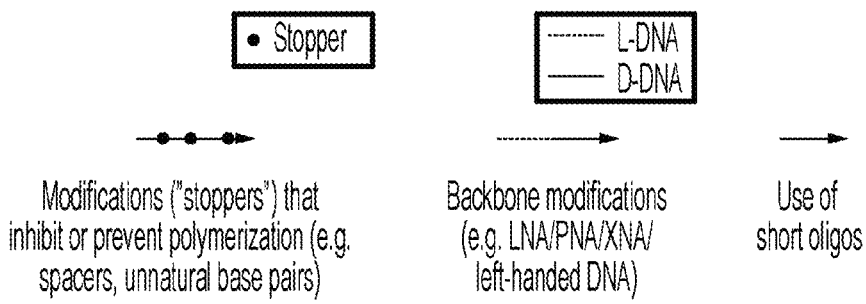
FIGS. 13A-13D illustrate example anti-counterfeiting measures.
Figure 13B:
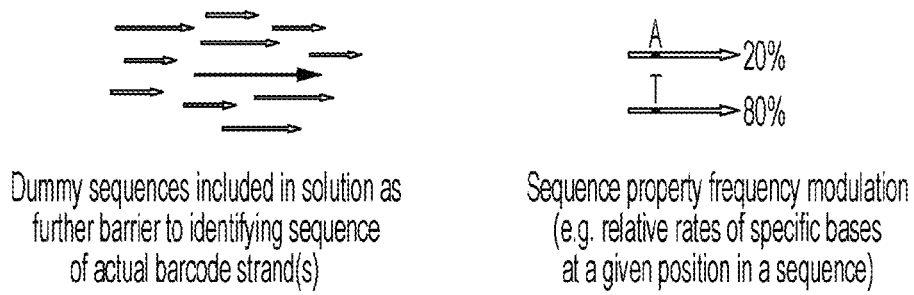

As described elsewhere herein, a tag or the authenticating identifier may comprise a nucleic acid molecule that has a structure such that the nucleic acid molecule cannot be identified by sequencing. FIG. 13A shows examples of unsequenceable oligos that may be used for anti-counterfeiting measures. The unsequenceable oligos may be a portion, or all of, the tags or the authenticating identifiers. For example, the nucleic acid molecule may comprise one or more of a nucleic acid enantiomer, a backbone modification, a covalent modification to a base of the nucleic acid molecule that may modulate hybridization of the base to another base, or at least one unnatural base pair. Unsequenceable oligos may include alternative types of nucleic acids such as peptide nucleic acids, lock nucleic acids, xeno nucleic acids, or left handed DNA. Alternately, or in addition to, the unsequenceable oligos may be of a length that is not sufficient for sequencing (e.g., are too short for sequencing). Furthermore, as described elsewhere herein, an authenticating identifier can include at least one nucleic acid molecule that exhibits sequence complementary to the tag. Tag sequences may be further mixed with several random or known sequences at various concentrations that serve as "dummy" sequences to increase the barrier for counterfeiters to copy and spoof the sequences. FIG. 13B shows the use of 'dummy' sequences for anti-counterfeiting. The 'dummy' sequences may be extraneous sequences in a mix or pool that are not associated with the tag or the authenticating identifier. Alternatively, or in addition to, the use of tags of varying length may be used to reduce or prevent counterfeiting.

Figure 13C:
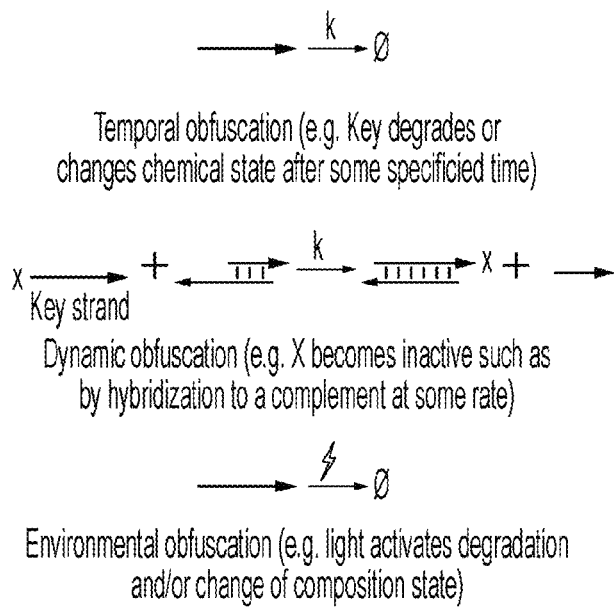
Figure 13D:
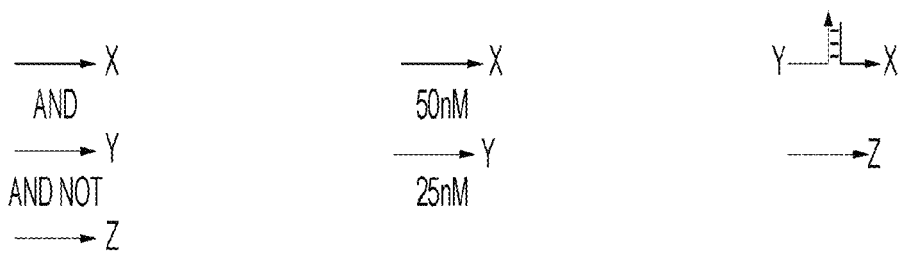
Figure 13D:
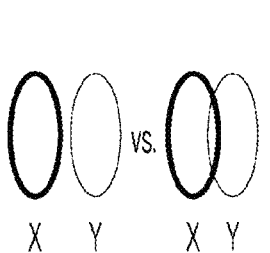
Figure 13D:
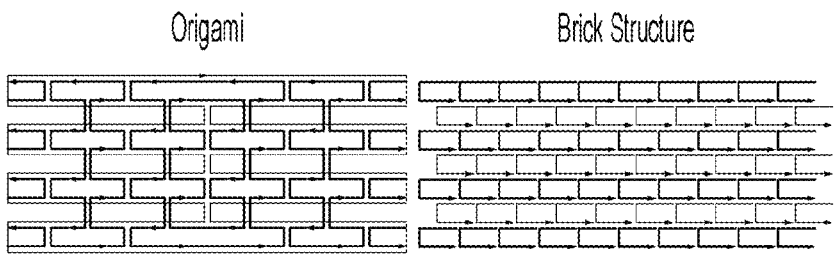

An alternate method for reducing or preventing counterfeiting may be the use of tags that change state. FIG. 13C shows tags that are programmed to change state (e.g., degrade or bind to different hybridization partners) over time. The change in state may be activated and provide for tags and authenticating identifiers that expire after a given period of time. Activation of the change of state may occur when the tags and authenticating identifiers are created or at a later time (e.g., when the tag and authenticating identifiers are combined). Environmental obfuscation methods may also be used to reduce or prevent counterfeiting. For example, light-sensitive reactions (e.g., light-sensitive degradation processes) may be used so that the product has a limited lifetime after being exposed to light (e.g. after opening the seal). The presence and/or absence of multiple tags strands (e.g. tags X, Y, and Z) may be evaluated to verify a solution. If the programmed logical expression evaluates to TRUE, the tag mix may be verified. Further properties of the composition may also be evaluated, such as the relative or absolute concentrations of species in the solution. The hybridization and/or structural state of tag strands in solution may further be evaluated such as through the use of any number of proximity-based molecular reactions. This may increase the difficulty of reproducing tag states even if the tags are sequenced. FIG. 13D shows the use of topological properties of tags for anti-counterfeiting. Topological properties may be modulated and validated, such as through the use of topoisomerase proteins that can loop two circular strands together. Sequencing the strands may not reveal this information. Additionally, specific nanostructures that may be verified (e.g. with atomic force or tunneling electron microscopes) may be incorporated into the tag to further enhance security.

It should be understood that unless stated otherwise, the 5' to 3' orientation of the strands described herein may be reversed (e.g., a tag comprising, from 5' to 3', domain X* and domain a, may be reversed to comprise, 5' to 3', domain a and domain X*). It should also be understood that if the orientation of a tag is reversed, the orientation of the components of a corresponding authenticating identifier may also be reversed.

Authenticating Identifiers

Figure 2A:
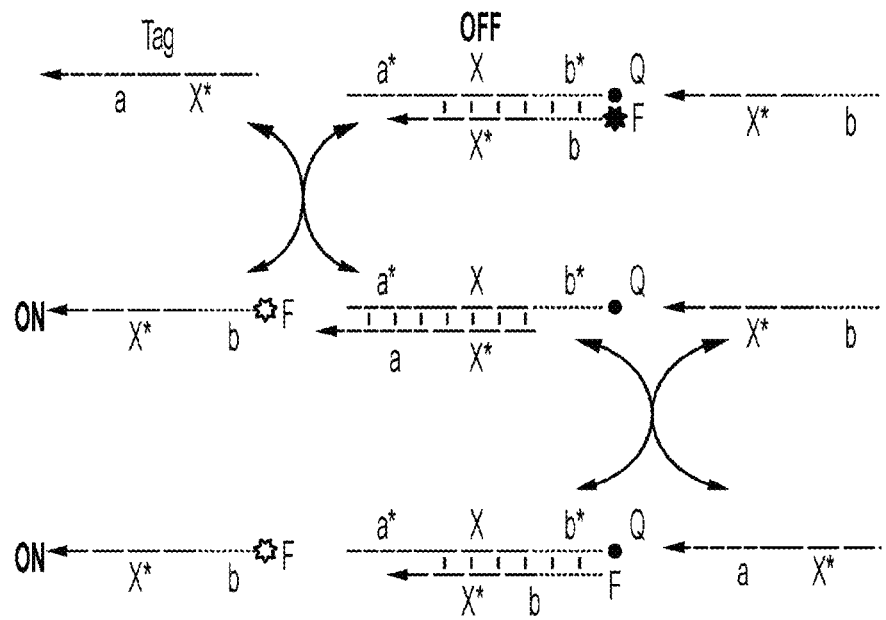
FIGS. 2A-2C illustrate example catalytic tag detection chemistries.
Figure 2B:
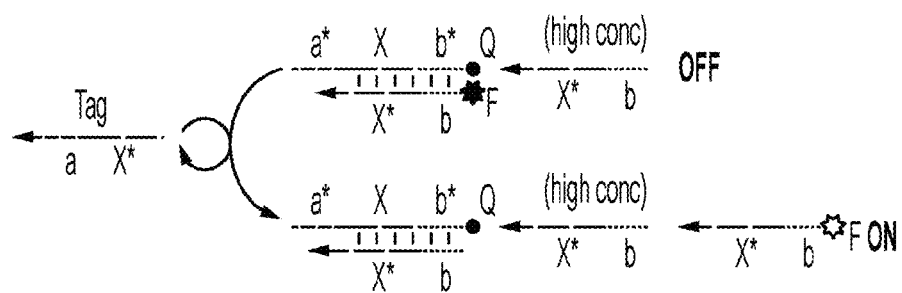
Figure 2C:
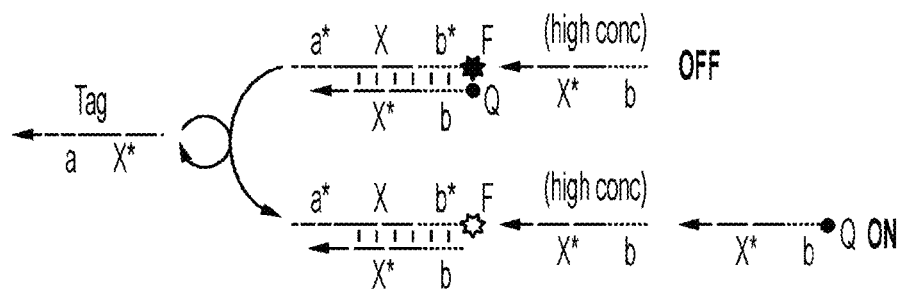

Authenticating identifiers are used as provided herein to authenticate a product, for example, by enabling identification of the tag(s). In general, an authenticating identifier comprises a nucleic acid strand or molecule that interacts with (e.g., binds to, such as via hybridization) a tag (e.g., a nucleic acid molecule or strand exhibiting sequence complementarity to the tag) and produces or quenches a detectable signal (e.g., a fluorescent signal). An example of an authenticating identifier is provided in FIGS. 2A-2C. FIG. 2A depicts the use of a toehold exchange for generating a positive (e.g., ON) authentication cascade. The toehold exchange cascade may comprise a tag strand (e.g., having a length of shorter than 50 nucleotide) comprising 5' domain X* and a 3' domain a. The authenticating identifier comprises a first strand, which includes, in the 5' to 3' direction, domain a*, domain x, domain b*, and one molecule of a quencher-fluorophore pair (e.g., a quencher). The second strand of the authenticating identifier comprises the other molecule of the quencher-fluorophore pair (e.g., a fluorophore), domain b, and domain x*. The third strand of the authenticating identifier comprises domain b and domain x* (without a quencher or fluorophore). Domain a binds to (e.g., is complementary to) domain a*, domain b binds to domain b*, and domain X binds to domain X*. If the correct tag is associated with a product, for example, the tag strand may interact with and bind to the first authenticating identifier strand, through a toehold exchange mechanism, thereby displacing the fluorophore-labeled second strand of the authenticating identifier to produce a detectable signal. The third authenticating identifier strand may comprise the X* and b domains, but may not include the fluorophore-label. The third strand of the authenticating identifier may prevent the fluorophore-labeled second authenticating identifier strand from re-binding to the first authenticating identifier strand, which may quench the signal and produce a false negative. FIG. 2B shows a method of biasing the equilibrium state of the toehold exchange reaction using a high concentration of the displacement strand (e.g., binding strand without fluorophore-label) relative to the concentrations of the fluorophore (F)/quencher (Q) complex and tag strands. The tag strand may act catalytically to enable the system to reach the biased equilibrium state by promoting displacement of the fluorophore-labeled strand and binding of the non-fluorescent strand to the strand with the quencher. By introducing the third authenticating identifier strand at a higher concentration relative to the first and second authenticating identifier strands, the reaction can be driven to the fluorescent "ON" state. FIG. 2C shows that the fluorophore and quencher strands may be reverse such that the quencher labeled strand is displaced from the fluorophore (F)/quencher (Q) complex.

Thus, in some embodiments, the concentration of the third authenticating identifier strand (the strand that comprises the same domains as the second authenticating identifier strand but without a fluorophore or quencher) is at least 2-fold higher than the concentration of the first and/or second authenticating identifier strand. In some embodiments, the third authenticating identifier strand is at least 3-fold, at least 4-fold, at least 5-fold, at least 6-fold, at least 7-fold, at least 8-fold, at least 9-fold, or at least 10-fold higher than the concentration of the first and/or second authenticating identifier strand. In some embodiments, the third authenticating identifier strand is at least 15-fold, 20-fold, 25-fold, 50-fold, or 100-fold higher than the concentration of the first and/or second authenticating identifier strand. In some embodiments, the third authenticating identifier strand is 2-fold to 100-fold, 1-fold to 50-fold, 2-fold to 10-fold, 5-fold to 100-fold, 5-fold to 50-fold, or 10-fold to 100-fold higher than the concentration of the first and/or second authenticating identifier strand.

The length of each of the authenticating identifier strands may be similar to the length of the tag strand. In some embodiments, the authenticating identifier strands have a length of shorter than 50 nucleotides, or even shorter than 30 nucleotides. Thus, in some embodiments, the length of an authenticating identifier strand is shorter than 45, 40, 35, 30, 25, 20, or 15 nucleotides. In some embodiments, the length of an authenticating identifier strand is 10-50, 10-45, 10-40, 10-35, 10-30, 10-25, or 10-20 nucleotides. In some embodiments, the length of an authenticating identifier strand is 10, 15, 20, 25, 30, 25, 40, 45, or 50 nucleotides. In some embodiments, the length of the first authenticating identifier strand (e.g., comprising domains a*, X, and b*, as depicted in FIGS. 2A-2C) is longer than the second authenticating identifier strand (e.g., comprising domains b and X*).

Figure 9A:
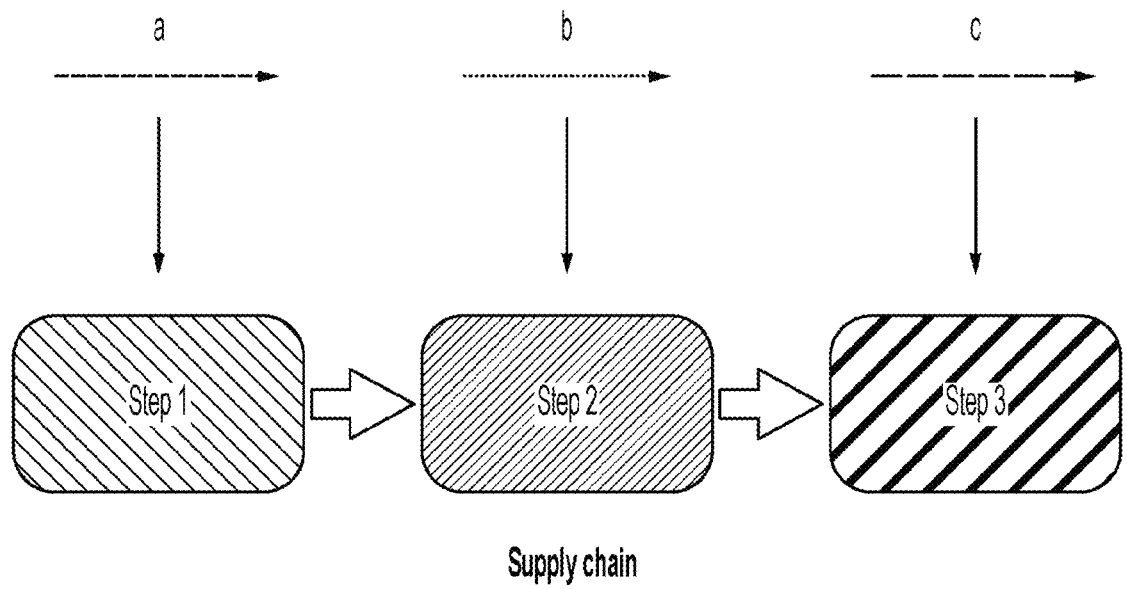
FIGS. 9A and 9B illustrate an example of supply chain authentication.
Figure 9B:
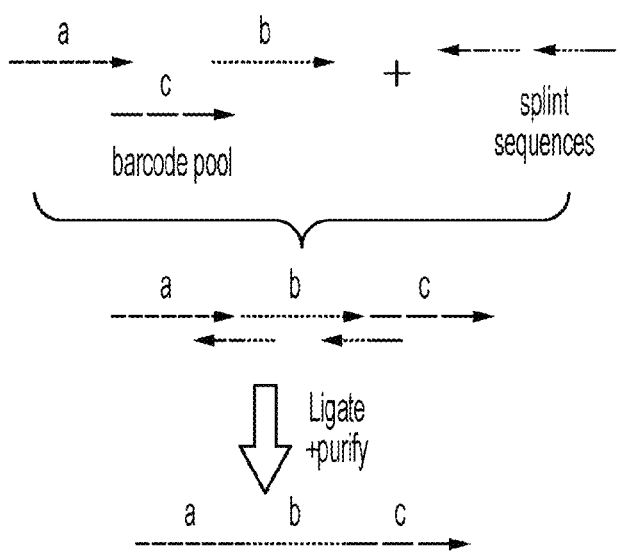

Another example of a molecular authenticating identifier composition is provided in FIG. 9B. In this example, the composition comprises two authenticating identifier strands: a first long strand comprises a quencher linked to domains Z*, c*, Y*, b*, X*, and a*; and additional shorter strands comprise domains X and b, domains Y and c, and domain Z linked to a fluorophore. The different tags, if they contain the correct sequences, ultimately displace the shorter authenticating identifier strands, thereby producing a detectable (e.g., fluorescent) signal.

As described herein, interaction of tags and authenticating identifiers can give rise to a detectable signal. As discussed in the examples above, such interaction may produce a fluorescent signal, including signals that become available as interactions between fluorophores and quenchers are broken (or made). Fluorescent signals are not meant to be limiting. Any detectable signal resulting from the interaction between a tag and authenticating identifier can be implemented. In some embodiments, interaction of a tag and an authenticating identifier can yield a detectable electronic signal, such, as a change in charge, a change in ion concentration, a change in conductivity and/or a change in impedance. In some embodiments, interaction of a tag and an authenticating identifier can yield a detectable optical signal. Signals may be one or more of luminescence, such as fluorescence, chemiluminescence, bioluminescence, colorimetric or any other type of optical emission or absorption. In some embodiments, interaction of a tag and an authenticating identifier can yield or aid in yielding a signal that is visually observable (e.g., a change in color, the development of a distinct visual pattern (e.g., a logo, a detectable code such as an optical barcode, QR code, a geometric pattern, a pattern in a particular shape (e.g., a check mark, an "X"), a complex pattern, a complex shape, etc.) as described elsewhere herein). In some embodiments, a detectable signal generated from interaction of a tag and authenticating identifier may be a pattern of optical signals. Signals may be enhanced by the inclusion of detectable moieties (fluorophores, charged species, etc.) that are released, that bind to the tag or authenticating identifier, or generate a signal when a tag and authenticating identifier interact. Moreover, detection can be completed by any suitable modality. Non-limiting examples, include optical detectors (e.g., fluorimeters, UV-Vis spectrophotometers, infrared spectrometers), microscopy (e.g., Atomic Force Microscopy, electron microscopy) and electronic detectors. In some embodiments, patterns may be invisible to the naked eye, but may be visible with the appropriate detector (e.g., DNA origami patterns visualized via Atomic Force Microscopy).

Figure 17:
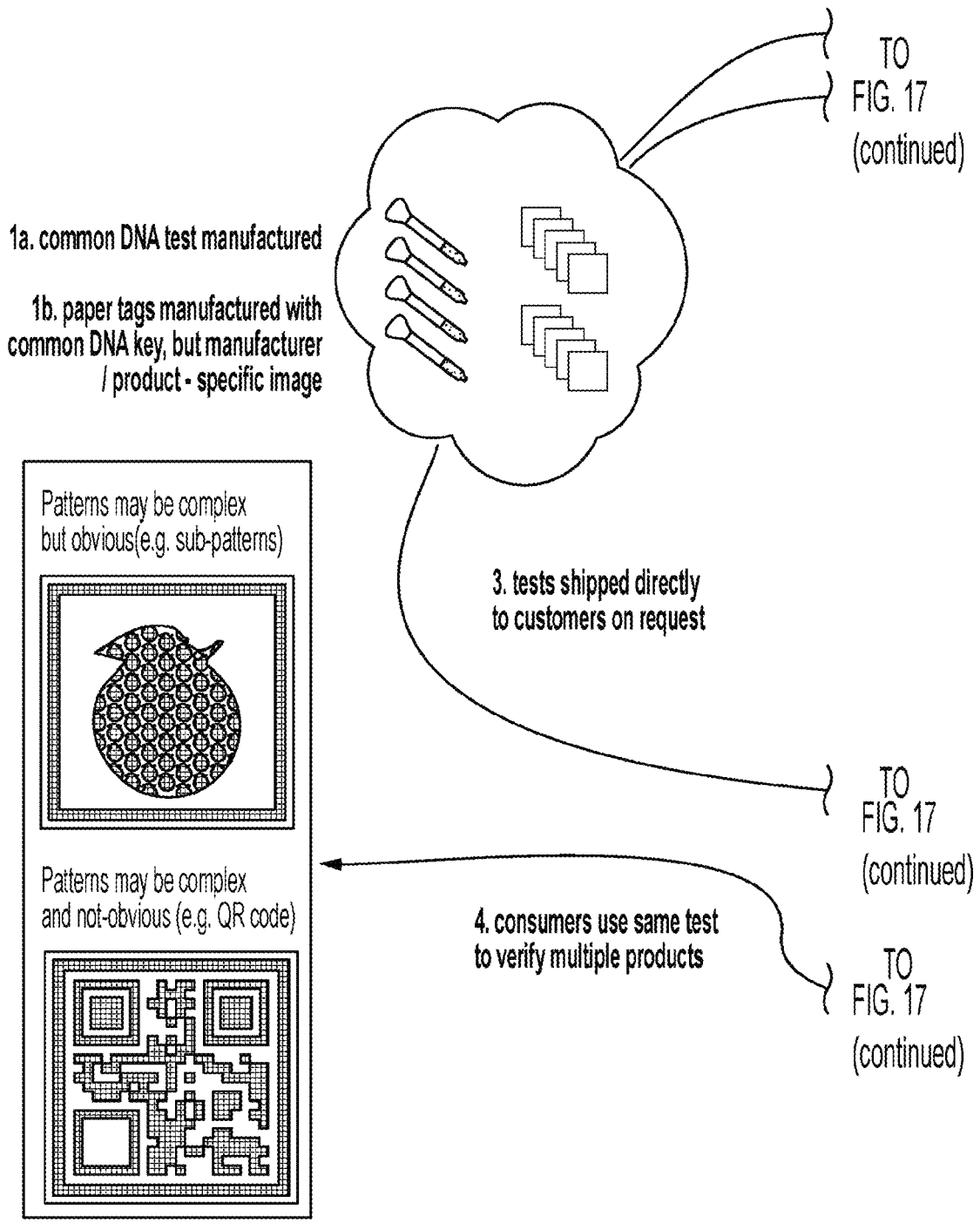
FIG. 17 shows an authentication method using a common test (typically applied by an end user) to multiple products to reveal a specific logo.
Figure 17:
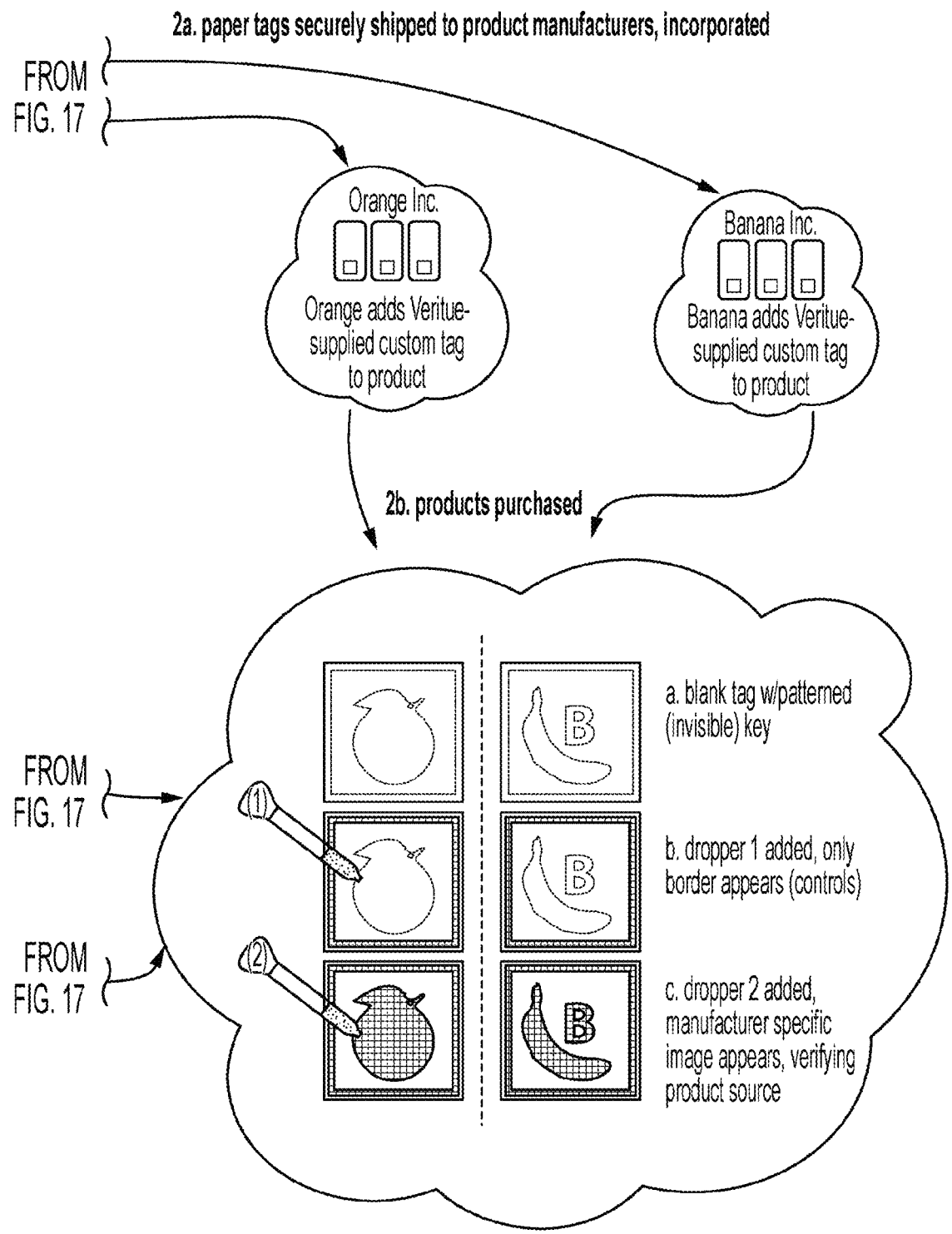

An example of generating a visual shape read-out is graphically depicted in FIG. 17. As shown in FIG. 17, a substrate can be coated with tags such that they are arranged in a particular pattern. As shown in FIG. 17, paper labels can be generated for different manufacturers (e.g., Orange, Inc. and Banana, Inc.) such that the labels contain a border region having the same tag, but have a region patterned as a distinct image such that each label for each manufacturer has a different image pattern. The manufacturers can apply the labels to products. A customer can apply a first authenticating identifier to the label to ensure that the system is working, such that a detectable signal (e.g., a visually observable border) is generated in the border region of the labels. A second authenticating identifier can be added to the labels such that the patterned image becomes visible to the customer (e.g., a detectable signal). In this example, if the developed image is an orange, the label identifies the associated product as manufactured by Orange, Inc. If the developed image is a Banana with a B, the label identifies the associated product as manufactured by Banana, Inc.

Moreover, also as shown in FIG. 17, additional layers of tags can be added to these labels such that a common larger image is developed with differing patterns in the larger image (e.g., see the label comprising a larger orange itself comprising smaller oranges in FIG. 17). Any number of different tags and associated authenticating identifiers can be implemented to effect multi-layer authentication. Furthermore, as is also shown in FIG. 17, the resulting image can be fashioned in a highly complex pattern such as the example two dimensional barcode (e.g., QR code) shown in FIG. 17. This image itself may not readily provide information encoded by the barcode, but can confirm one level of information and a separate barcode reader (e.g., such as software on a mobile device) can be used to retrieve the embedded information.

Figure 18:
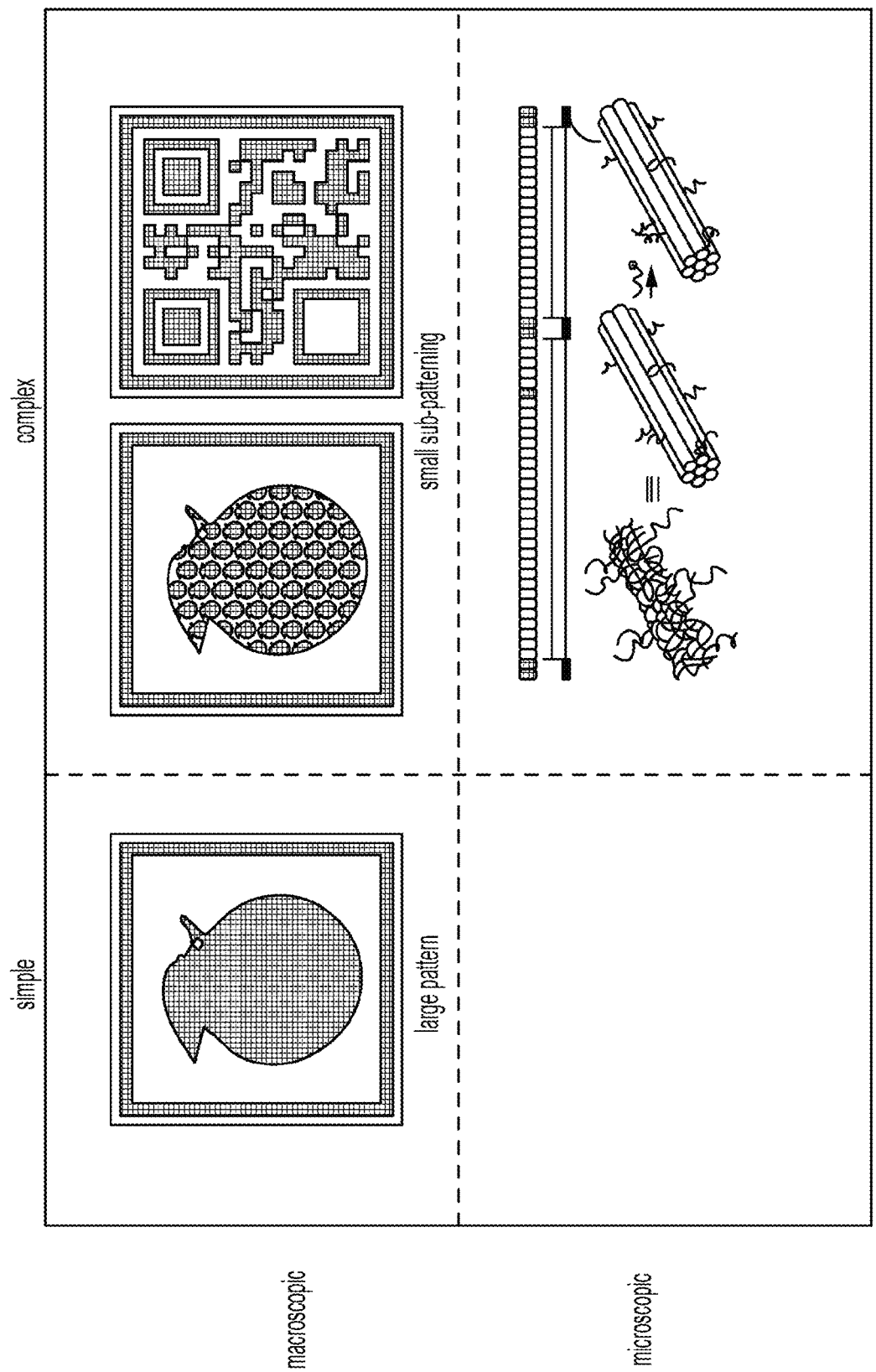
FIG. 18 shows a common tag and authenticating identifier method that may be carried out at the macroscopic and/or microscopic scales.

In another example, FIG. 18 schematically illustrates a comparison of macroscopic and microscopic authentication modalities. In the top row of FIG. 18, are macroscopic patterns that can be generated as described with respect to FIG. 17. In the bottom row of FIG. 18 are microscopic patterning and authentication modalities. Patterning can be made with structures that are invisible to the naked eye and thus may be analyzed with another modality (e.g., microscopy, such as diffraction limited optical, super-resolution optical, atomic force microscopy, or electronic microscopy). For example, one or more species of DNA origami, DNA bricks, DNA crystals, DNA brick crystals, non-DNA structures, or "top-down" via Action-PAINT structures may exist on a surface, but the correct pattern may only be read with the appropriate tag. In some embodiments, an invisible pattern comprises a plurality of nanostructures, such as nucleic acid nanostructures (agglomerations of nucleic acids, nucleic acids coupled to nanoparticles, etc.). Interaction of the proper tag with these structures can displace fluorophores or quenchers from the structures, incorporate fluorophores, quenchers, or biotin-streptavidin makers for visualization (e.g., via atomic force microscopy), or serve as bridges to immobilize nucleic acid strands with detectable features.

In another example, a label may be patterned with nucleic acid tag that interacts with a particular nucleic acid authenticating identifier such that the nucleic acids form a particular shape or structure (e.g., either detectable visually or with appropriate aids such as microscopy) as a result of assembly into particular two-dimensional and/or three-dimensional nucleic acid structures (e.g., via nucleic acid origami, such as DNA origami). Examples of forming two and three-dimensional nanostructures are provided in PCT Publication No. WO2017143006, which is herein incorporated by reference in its entirety for all purposes. The tags may be nanostructures or microstructures, or the tags may be associated with nanostructures or microstructures. Nanostructures may include nanoparticles, nanorods, nanostrings, nanotubes or nanosheets. In some embodiments, the tags may be associated with nanostructures or microstructures, such that agglomeration of nanoparticles in the formation of two-dimensional and three-dimensional nucleic acid structures renders the structures visible macroscopically or detectable microscopically or via other modalities. In some embodiments, nanoparticles or other supporting structures are not used and two-dimensional and three-dimensional structures are purely nucleic acid based. In some embodiments, tags may be patterned on a label such that their formation of higher order structures develops a visible image or an image that can be detected with appropriate instrumentation. Such a strategy can be useful in employing a common authenticating identifier in authentication strategies.

For example, an electronic manufacturer may associate a product with a label comprising tags that form two-dimensional and/or three dimensional structures when contacted with an authenticating identifier. The authenticating identifier can be provided to customers, such that it does not uniquely identify a particular customer. The common authenticating identifier, however, can be applied to the product such that it interacts with the tag and two or three dimensional structures are generated and that can be detected.

In an aspect, the present disclosure provides a method for producing a product that is authenticable by a user. The method comprises admixing an article with a tag having at least one nucleic acid molecule. Interaction between the tag and an authenticating identifier exhibiting binding specificity for the tag may yield a detectable signal that is indicative of authenticity of the product, thereby producing the product that is authenticable by the user. In some embodiments, the method further comprises admixing the article with one or more nucleic acid molecules that do not exhibit binding specificity for the authenticating identifier. In some embodiments, the method further comprises admixing the article with at least about 10, 50, 100, 500, 1000, 5000, 10000, 50000, 100000 or more nucleic acid molecules that do not exhibit binding specificity for the authenticating identifier. In some embodiments the one or more nucleic acid molecules are different.

In another aspect, the present disclosure provides a product that is authenticable by a user. The product comprises an article admixed with a tag having at least one nucleic acid molecule. The interaction between the tag and an authenticating identifier exhibiting binding specificity for the tag yields a detectable signal that is indicative of authenticity of the product. In some embodiments, the product further comprises one or more additional tags admixed with the article and the tag such that the authenticating identifier does not exhibit binding specificity for the one or more additional tags. For example, the product may further comprise at least about 10, 50, 100, 500, 1000, 5000, 10000, 50000, 100000 or more additional tags for which the authenticating identifier does not exhibit binding specificity.

In some embodiments the one or more additional tags are different. Furthermore, the product may comprise a transmission unit configured to transmit an electronic signal indicative of the presence or absence of the detectable signal to a designated party. The designated party can be any person or entity such as, for example, the producer of the product, a regulatory agency or personnel, a distributor in a supply chain, a customer of the producer, and any other party authorized to receive such confirmation or a lack thereof.

In another aspect, the present disclosure provides a method for testing authenticity of a product by a user. The method comprises: (i) applying a solution comprising an authenticating identifier to the product containing or suspected of containing a tag. The authenticating identifier can exhibit binding specificity for the tag and interaction between the authenticating identifier and the tag yields a detectable signal that is indicative of authenticity of the product. The method also can include: (ii) identifying a presence or absence of the detectable signal, thereby testing the authenticity of the product. The presence of the detectable signal may indicate that the article is authentic. Application of the solution to the product can be achieved in any suitable manner, such as, for example, drop-by-drop (e.g., with a dropper), spraying, rubbing, agitation, smearing, in bulk, etc.

In some embodiments, the method further comprises alerting or notifying a party in a supply chain of the product (e.g., the manufacturer, a distributor, etc.) as to the authenticity of the product (and, In some embodiments, such as a finding that the product lacks authenticity, requesting a remedial measure from that party), as is described elsewhere herein. In some embodiments, the product further comprises one or more additional tags and the tag such that the authenticating identifier does not exhibit binding specificity for the one or more additional tags. For example, the product may further comprise at least about 10, 50, 100, 500, 1000, 5000, 10000, 50000, 100000 or more additional tags for which the authenticating identifier does not exhibit binding specificity.

As described elsewhere herein, a tag or the authenticating identifier may comprise a nucleic acid molecule that has a structure such that the nucleic acid molecule cannot be identified by sequencing. FIG. 13A shows examples of unsequenceable oligos that may be used for anti-counterfeiting measures. The unsequenceable oligos may be a portion, or all of, the tags or the authenticating identifiers. For example, the nucleic acid molecule may comprise one or more of a nucleic acid enantiomer, a backbone modification, a covalent modification to a base of the nucleic acid molecule that may modulate hybridization of the base to another base, or at least one unnatural base pair. Unsequenceable oligos may include alternative types of nucleic acids such as peptide nucleic acids, lock nucleic acids, xeno nucleic acids, or left handed DNA. Alternately, or in addition to, the unsequenceable oligos may be of a length that is not sufficient for sequencing (e.g., are too short for sequencing). Furthermore, as described elsewhere herein, an authenticating identifier can include at least one nucleic acid molecule that exhibits sequence complementary to the tag.

Authentication Methods

Figure 19:
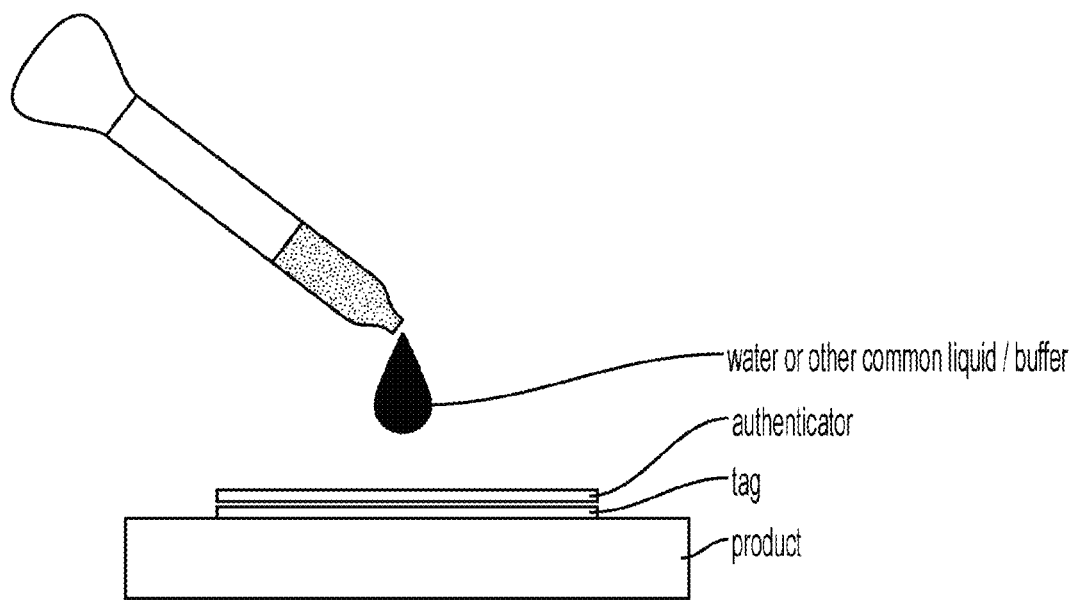
FIG. 19 shows an example authentication system using a paper based tag and authenticating identifier.
Figure 20:
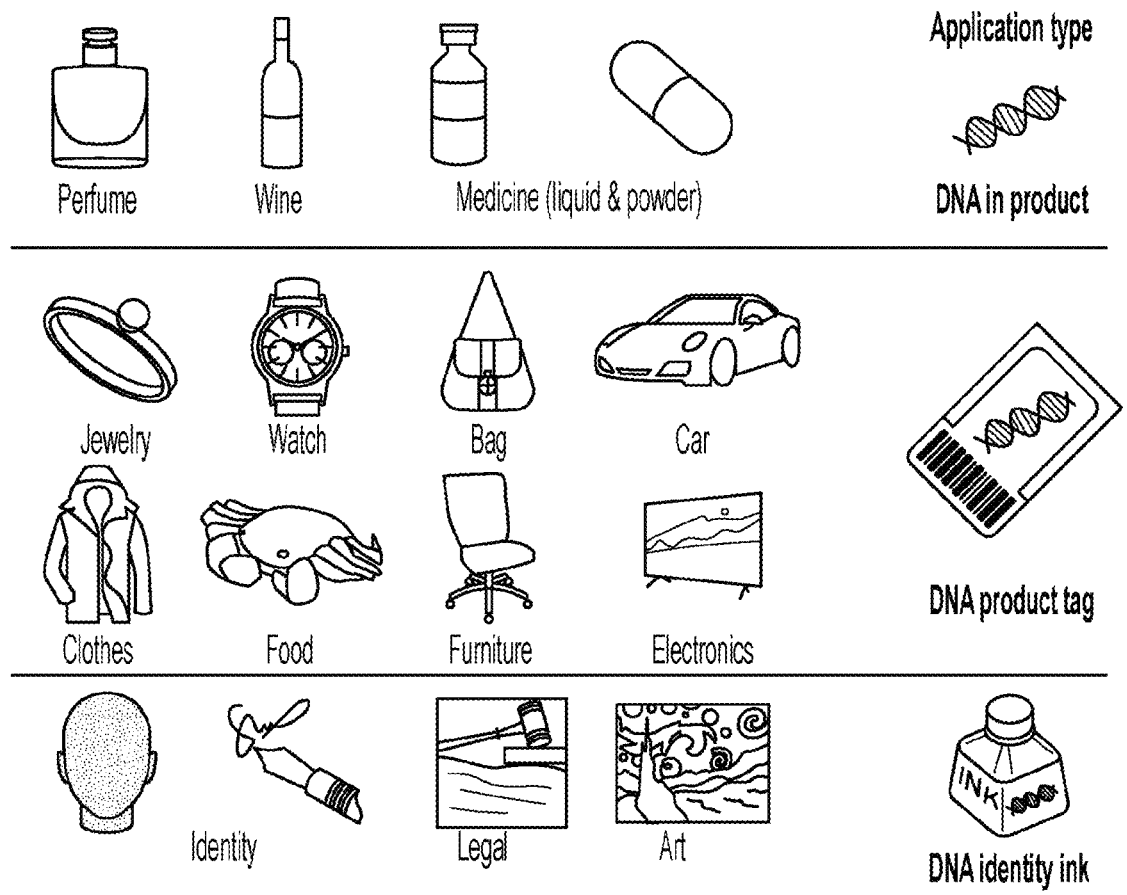
FIG. 20 illustrates example applications of the molecular authentication methods disclosed herein.

The authentication methods described herein may be coupled with one or more signal generating methods to generate a detectable authentication signal. For example, the authentication methods may be coupled with optical, electrical, or topographical detection methods to generate a signal. Optical detection methods may be fluorescent (e.g., via fluorescence generation or fluorescence quenching), colorimetric, or other visual detection method. Electrical detection methods may include the detection of impedance, piezoelectric, amperage, voltage, and other electrical signals. Topographical detection may include the generation of topographical features during authentication that may be detected (e.g., using atomic force microscopy or tunneling electron microscopy). The tag or authenticating may be present in a solid, liquid, or semi-solid form. The tag may be solid and the authenticating identifier may be liquid. The tag may be liquid and the authenticating identifier may be solid. Alternatively, both the tag and the authenticating identifier may be solid. FIG. 19 shows an example of both the tag and the authenticating identifier being in a solid state. Both the tag and the authenticating identifier may be added to a paper or other material and dried or freeze dried to the paper/material. Prior to authentication, both the tag containing material and the authenticating identifier containing material may be disposed adjacent to or stacked on one another. An aqueous solution (e.g., water, buffer, etc.) may be added to the tag and authenticating identifier materials. The aqueous solution may solubilize one of or both of the tag and authenticating identifier and enable the tag and identifier to contact and generate a signal. The material containing the tag (e.g., label or paper) may be one-time use or re-usable, either with or without a subsequent wash step.

Figure 22:
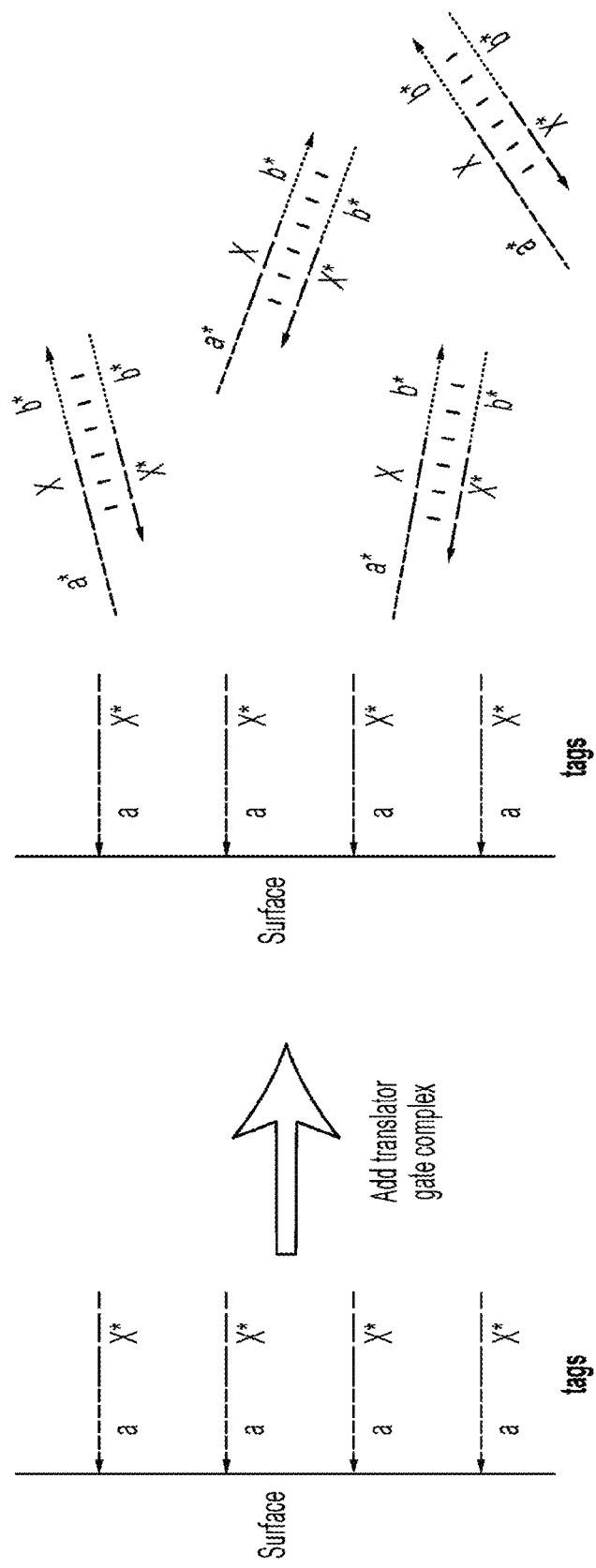
FIG. 22 illustrates an example authentication method that generates a detectible signal from a released intermediate.
Figure 22:
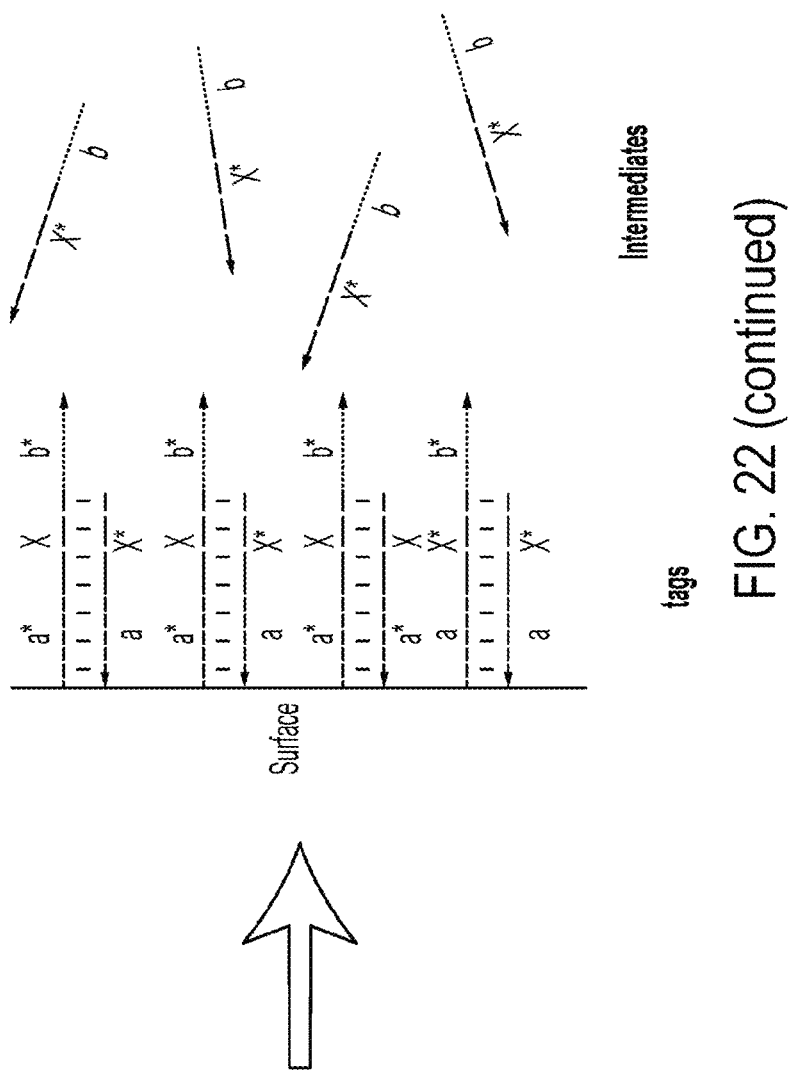

An authentication system may further comprise a translator gate. A translator gate may generate a signal from a released intermediate rather than from an interaction of the tag with the authenticating identifier. FIG. 22 shows an example translator gate that generates an intermediate. The tag may be conjugated to a surface. The surface may comprise one tag or more than one tag. The tag may be conjugated to the surface through a covalent bond or by an association interaction (e.g., hybridization, ligand binding, etc.). The tags may be single-stranded nucleic acid molecules. A translator gate complex may be added to the surface conjugated tags. The translator gate may be double-stranded nucleic acid molecules. One strand of the translator gate complex may share complementarity with the tag. The strand that share complementarity with the tag may release from the other strand and hybridize with the tag. The released single-stranded molecule may be the intermediate. The intermediate may be detected using and of the detection methods described herein.

Figure 14A:
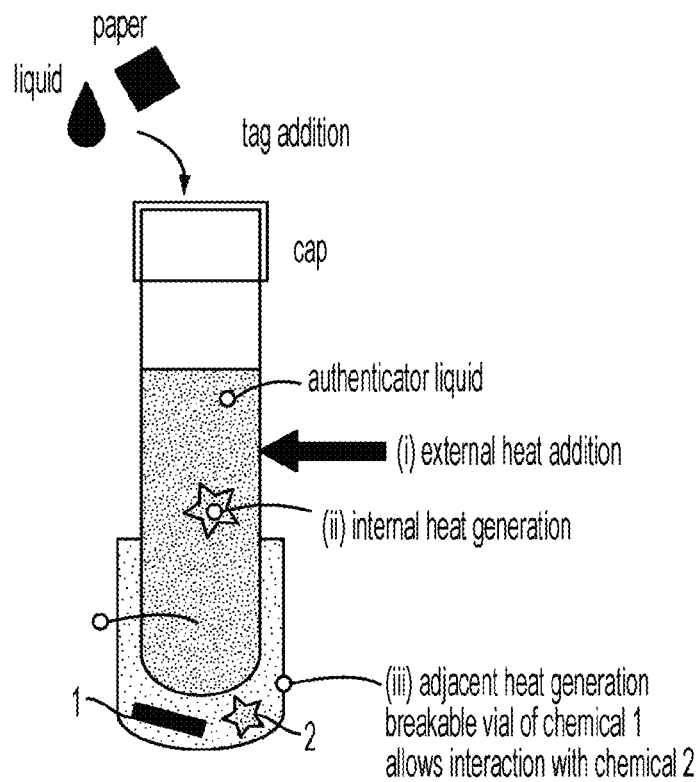
FIG. 14A shows the use of thermal treatment to increase the rate of authentication.
Figure 14B:
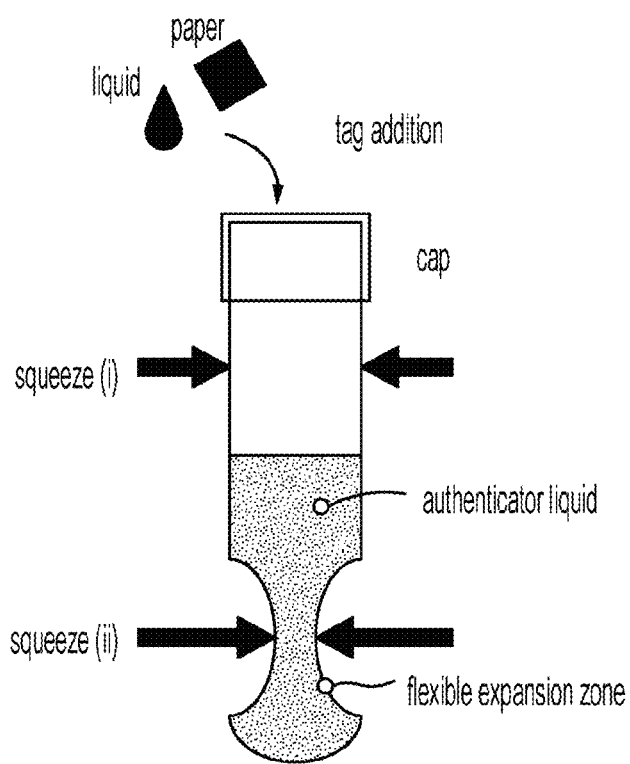
FIG. 14B shows the use of external mixing to increases the rate of authentication.

The authentication reactions that generate a signal may be slow or may be rapid. The rate of signal generation may be increased (e.g., drive to completion more rapidly) with the addition of mixing or heating to the reaction. For example, the tag may be in a liquid or solid (e.g., dried on a paper) form. The authenticating identifier may be in liquid or solid form. FIG. 14A shows the addition of heat to increase the rate of signal generation. Increasing the reaction temperature may result in a decrease in reaction time. Heat may be added externally (e.g., by a user's body temperature) or internally by a chemical reaction (e.g., enthalpic reactions). Alternatively, or in addition to, heat may be added chemically through an adjacent vessel (e.g., by breaking an internal vial and generating a chemical reaction). FIG. 14B shows an example of a liquid authenticating identifier and a solid tag (e.g., dried onto a paper) added to a reaction solution in a flexible tube. The flexible tube may have an expansion zone that facilitates flow from one portion of the tube to another portion of the tube. The tube may be capped and squeezed to employ more rapid mixing of the components. In an example, the mixing may enable nanoparticle dispersion and color generation.

Figure 21:
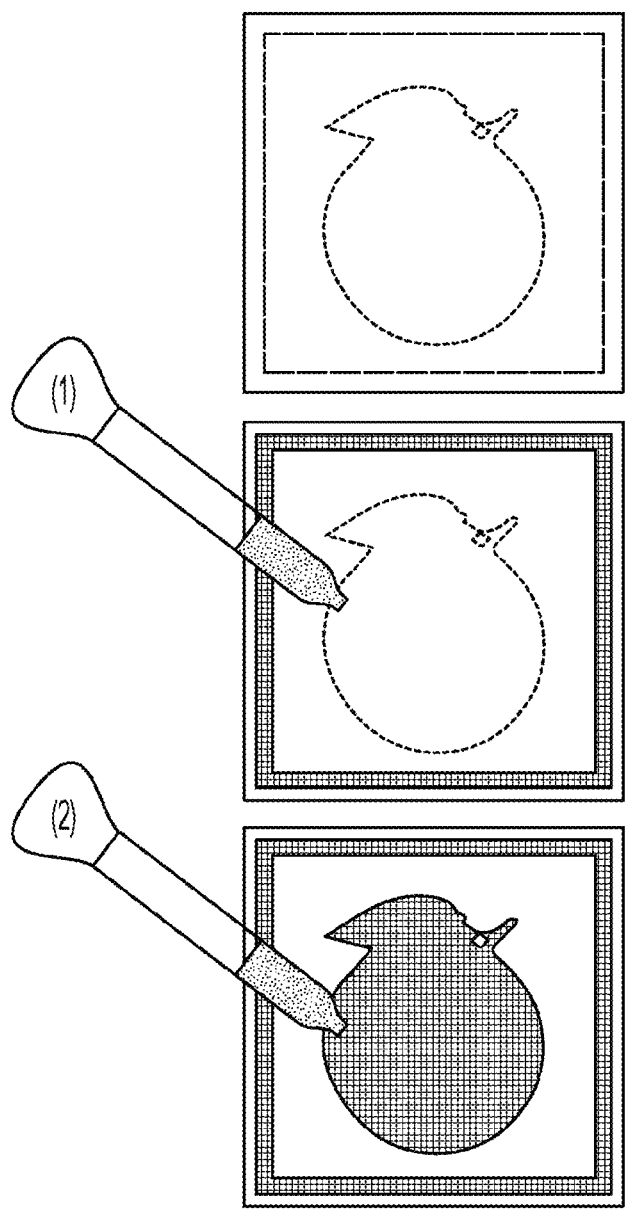
FIG. 21 shows a paper label based authentication method using a company logo.

An authentication method may be a single, double, triple or more component method. Multiple components may enable the detection of a positive control, negative control, and authenticating indicator. In an example, a label (component A) may be provided with a product and an authentication test (component B) may be provided by an independent verification organization. Component B may be provide to Component A to verify the authenticity of the product independent from the manufacturer or supplier. The components may be provided in any form, such as liquid, solid, semi-solid, gel, or any combination thereof. FIG. 21 shows a paper-based label authentication method using a company logo. A blank paper label (component A) may be provided to a consumer by the supplier or retailer. The paper label may comprise one or more regions with one or more tags. The verification organization may provide one or more tests. The test may include liquid or solid components. The first test may be a positive control or a negative control. The first test may be added to the label in liquid form. The first test may generate a signal on one or more regions of the label. For example, the first test, or positive control, may generate a visual boarder around the label. The first test may indicate that the label is operational. A second test may be applied to the label. The second test may indicate the origin of product. For example, the second test may indicate a brand of the product. The second test may comprise the authenticating indicator that matches the brand. If the product is authentic a positive result may be generated. The positive result may be in the form of a color change, shape, change, or both a color and shape change on the label. In an example, a positive result generates a colored logo representing the brand.

Figure 24B:
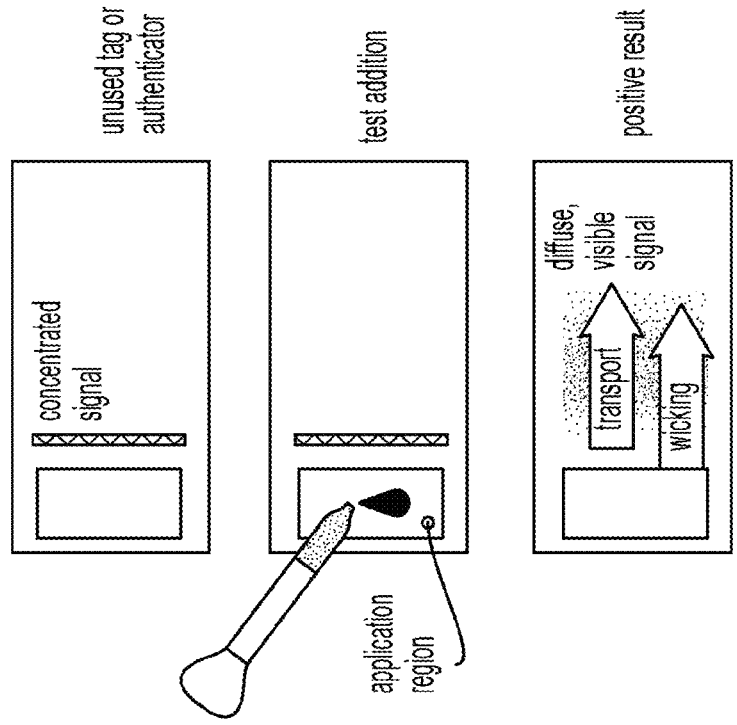
FIGS. 24A and 24B illustrate example visual detection of authentication signals.
Figure 24A:
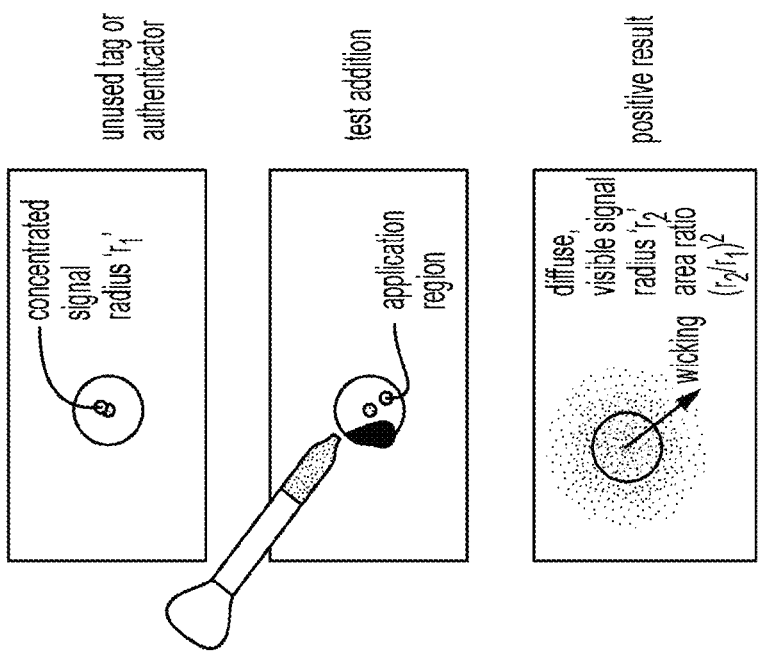

The authentication methods described herein may be coupled with one or more signal generating methods to generate a detectable authentication signal. FIGS. 24A and 24B illustrate example methods for visual detection of authentication signals. The tag may be present on a label. The label may be made of paper or other wicking material. Addition of the authenticating identifier (that comprises test substrate and strands) may generate a visual signal on the label. The label may wick the signal across the label and amplify the signal by expending a visible pigment or fluorescent domain from a small area of high concentration to a larger area of lower concentration. FIG. 24A shows the tag concentrated in a small circular radius. The authenticating identifier may be added to the small circular radius. The authenticating identifier may be in solution form. Contacting the identifier solution with the paper may cause the solution to wick radially outward. If the authenticating identifier matches the tag, the wicking region may generate a visible signal of increasing radius. FIG. 24B shows an alternate detection approach that comprises a line of tag employed on a label. Addition of a solution based authenticating identifier to one side of the concentrated line of tag may cause the authenticating identifier to contact the line and wick the solution away from the application location. If the authenticating identifier matches the tag, the wicked solution may comprise a visible and expanding signal (e.g., via fluorescence or pigment).

Figure 25:
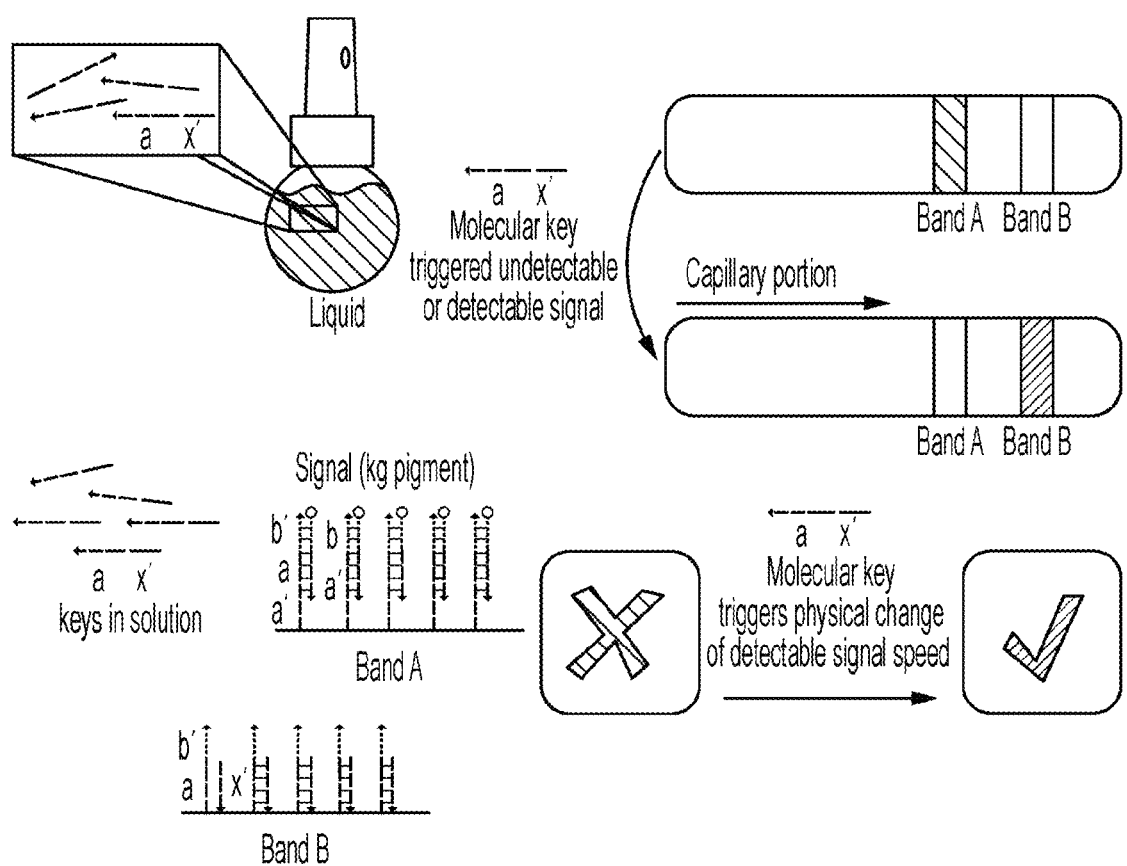
FIG. 25 shows a capillary-based authentication method.

FIG. 25 shows a capillary-based authentication approach. A liquid-based tag may be dropped or sprayed onto a capillary strip, which may enable the pigment to move from one band to another if the correct authenticating identifier is present. An example system uses a cascade toehold-mediated strand displacement reactions to facilitate migration of the pigment bound nucleic acid molecules from the first line to the second line.

Figure 26:
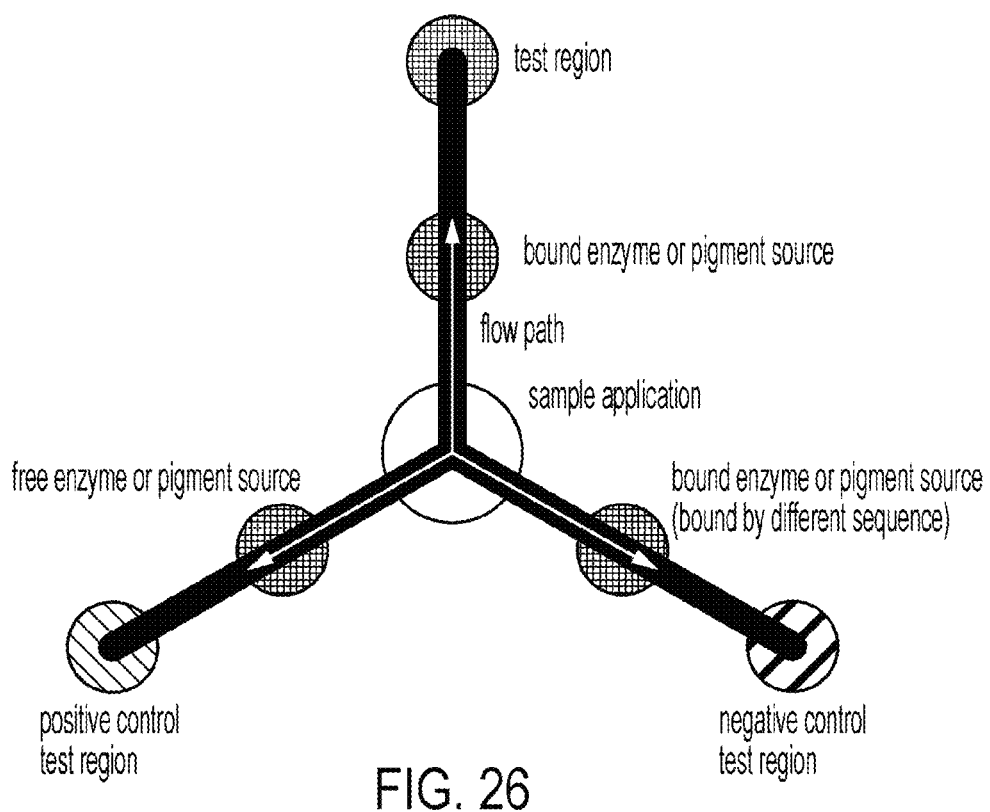
FIG. 26 shows a wicking-based authentication method.

FIG. 26 shows a wicking-based multicomponent authentication method. The label may be a paper based label or may be formed of other wicking materials. The label may have three or more areas. One area may be indicative of a positive control, one area may be indicative of a negative control, and another area may be indicative of the test region (e.g., authentication region). Each area may be fluidly connected by a wicking material or a microchannel. Each area may comprise a different tag. A test fluid comprising the authenticating identifier, positive identifier, and negative identifier may be applied to the center of the label (e.g., center of the wicking area or microchannels). The sample may travel away from the center (e.g., application area) to each of the testing areas. The positive control area may generate a signal if the label and testing fluid are functioning correctly. The negative control may not generate a signal if the label and testing fluid are functioning correctly. The testing area may generate a signal if the authenticating identifier matches the tag present in the test area (e.g., if the product is authentic).

Enzyme-Catalyzed and Colorimetric Authentication

Also provided herein are enzyme-linked compositions and methods for molecular authentication. Enzymes can catalyze reactions that are possible when tag interacts with authenticating identifier. Tag, enzyme and authenticating identifier can all interact together in a molecular complex, such that presence of an enzyme can catalyze reaction of the enzyme with its substrate when present at a test site.

An aspect of the present disclosure provides a molecular complex comprising a first nucleic acid molecule coupled to a second nucleic acid molecule through a third nucleic acid molecule having sequence complementarity with the first nucleic acid molecule and the second nucleic acid molecule, which second nucleic acid molecule may be conjugated to an enzyme.

Another aspect of the present disclosure provides a product comprising an article admixed with a molecular complex, which molecule complex comprises a first nucleic acid molecule coupled to a second nucleic acid molecule through a third nucleic acid molecule having sequence complementarity with the first nucleic acid molecule and the second nucleic acid molecule. The second nucleic acid molecule may be conjugated to an enzyme.

In some embodiments, the enzyme catalyzes a reaction yielding a detectable signal. The detectable signal may be any type of signal described elsewhere herein. In some embodiments, the reaction yields a signal that is detectable by a naked eye, without the aid of a detector, such as an optical detector. The enzyme may be any suitable enzyme such that interaction with its substrate either directly or indirectly generates a detectable signal.

The first nucleic acid may be coupled to an article and may function as a tag. The third nucleic acid molecule may function as an authenticating identifier that interacts with the first nucleic acid molecule. At the site of the third nucleic acid molecule or elsewhere, there may be a substrate that interacts with the enzyme and generated the detectable signal. In some embodiments, the first nucleic acid molecule may be coupled to the article at a first region. The article can include a second region comprising the third nucleic acid molecule having sequencing complementarity with the second nucleic acid molecule. The interaction between the second nucleic acid molecule and the third nucleic acid molecule may yield a detectable signal.

Figure 27A:
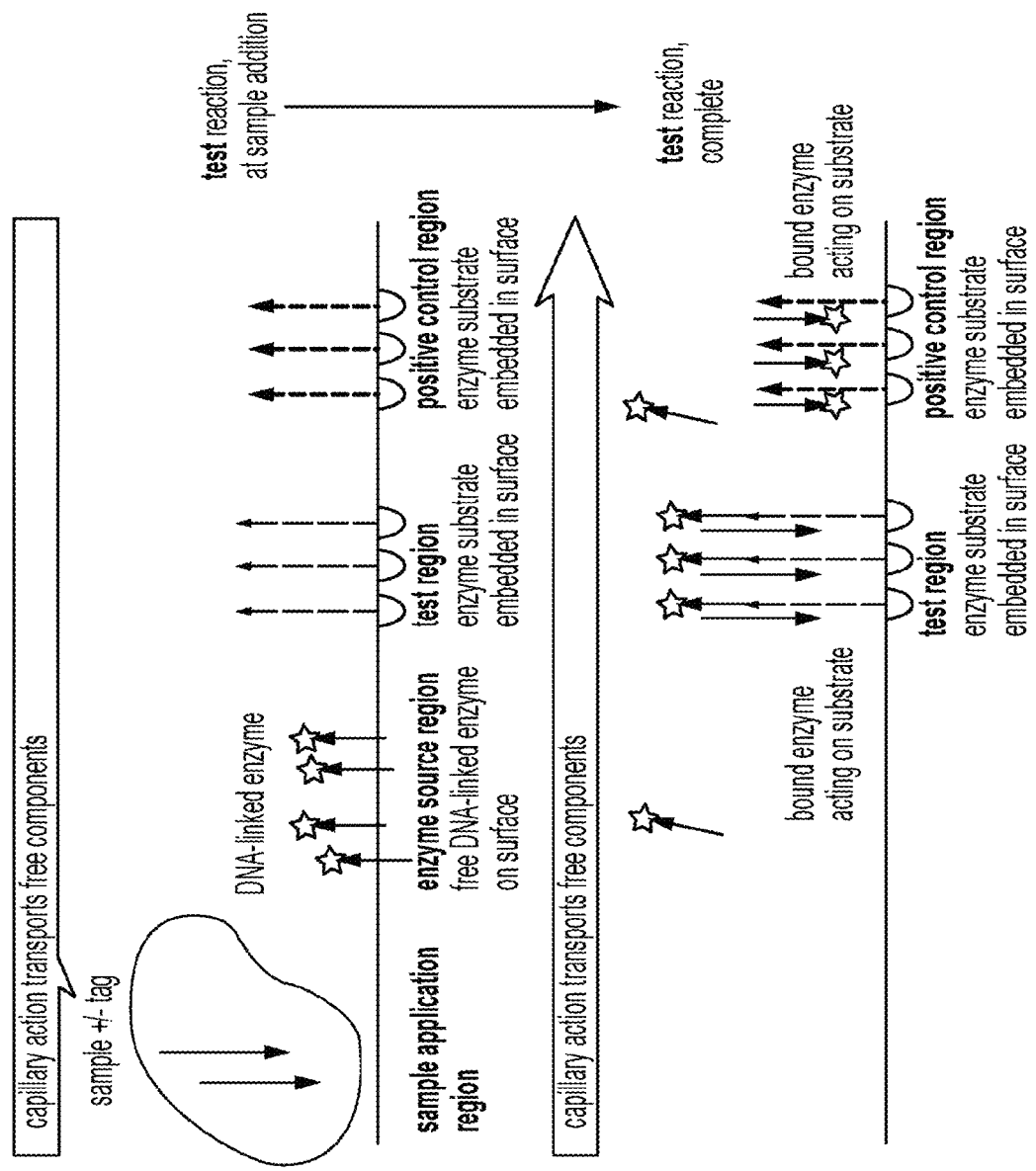
FIGS. 27A-27E illustrate example authentication methods using enzyme catalyzed signal generation.

An example of enzyme-catalyzed authentication is schematically depicted in FIG. 27A. As shown, a liquid sample can be provided to a test strip (e.g., a paper test strip) that transports free components in the liquid sample through the test strip via capillary action. The test strip has various zones, including an enzyme source region (comprising oligonucleotides conjugated to horseradish peroxidase enzyme); a test region comprising authenticating identifiers and a positive control region that has sequence complementarity to the oligonucleotides attached to the enzyme. At both the test region and the positive control region, substrate for the enzyme is present, such that enzyme immobilized at each site can catalytically interact with the substrate and produce a detectable signal (e.g., an optical signal, change in color, etc.).

The sample may contain tags that can authenticate the sample or components of the sample. As the sample travels through the test strip via capillary action, the enzyme-coupled oligonucleotides in the enzyme source region bind to a portion of the tags and also jettison some of these oligonucleotides from the enzyme source region such that they are free in the moving sample. These complexes than flow through the test region and, via, a different portion of the tags, bind to authenticating identifier in the rest region such that the enzyme is immobilized at the test region. The enzyme catalyzes conversion of its substrate and a detectable signal is generated. Moreover, free oligonucleotide coupled to enzyme also binds with oligonucleotides in the positive control region such that enzyme again converts its substrate, indicating that enzyme was released from the enzyme source region by the appropriate tags. The positive control region indicates that the test is complete.

Figure 27B:
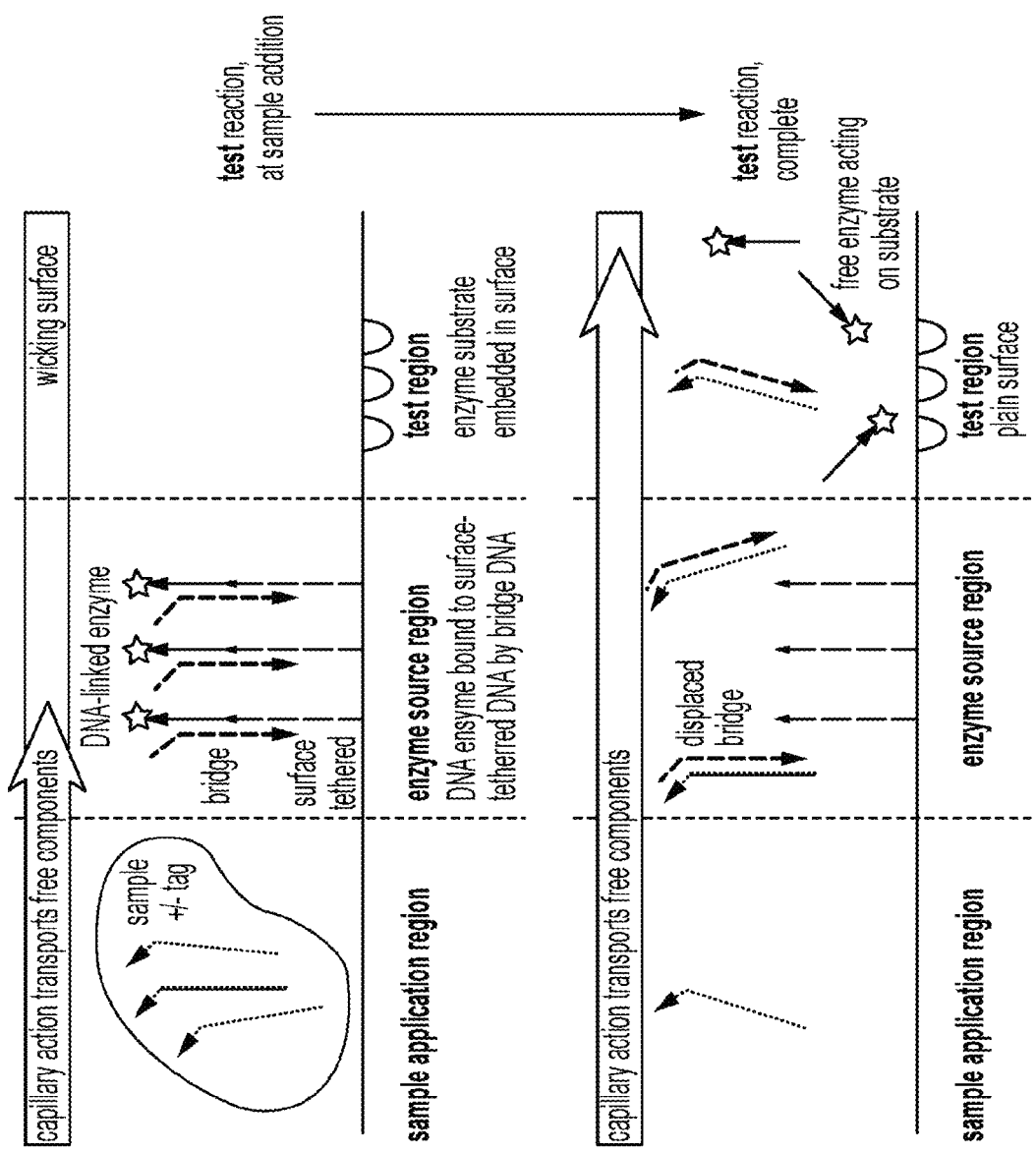

Another example of enzyme-catalyzed authentication is schematically depicted in FIG. 27B. As shown, a liquid sample can be provided to a test strip (e.g., a paper test strip) that transports free components in the liquid sample through the test strip via capillary action. The test strip has various zones, including an enzyme source region comprising authenticating identifiers bound to a complement (e.g., a full complement) of the sample tags, which complement is also bound to oligonucleotide conjugated with enzyme (e.g., horseradish peroxidase). At the test region, substrate for the enzyme is present, such that enzyme present at the test region can catalytically interact with the substrate and produce a detectable signal (e.g., an optical signal, change in color, etc.).

The sample may contain tags that can authenticate the sample or components of the sample. As the sample travels through the test strip via capillary action, complementary oligonucleotides coupled to the authenticating identifier and the enzyme-coupled oligonucleotides in the enzyme source region bind to the tags such that the interaction of the complement with the oligonucleotides conjugated to the enzyme and interaction with the authenticating identifier are both broken. Flow transports free oligonucleotides conjugated to the enzyme from the enzyme source region to the test region, where the enzyme interacts with its substrate and generates a detectable signal.

Figure 27C:
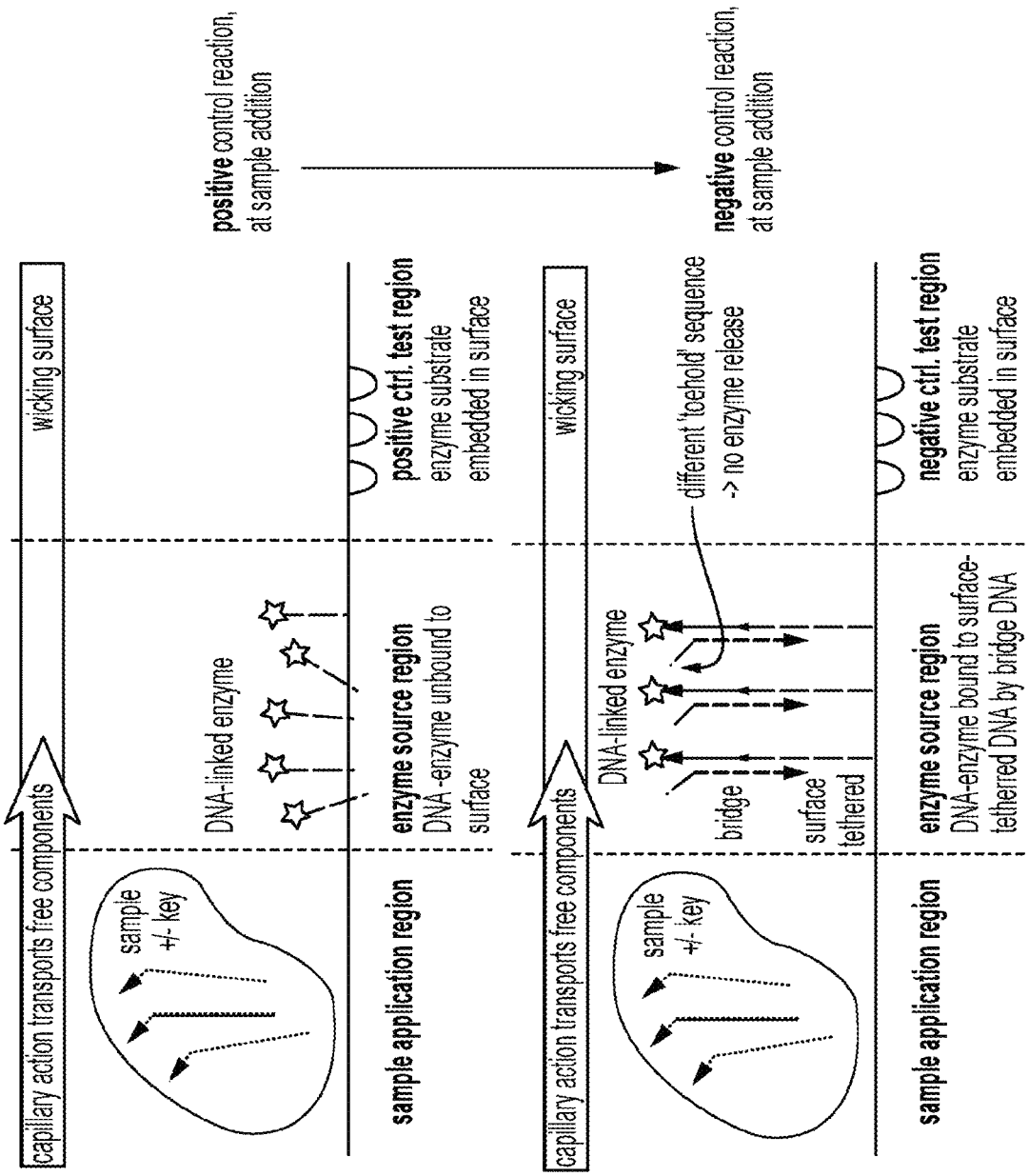

In another example and as discussed above with respect to FIG. 27A, positive and controls can be implemented in enzyme-catalyzed authentication. As shown schematically in the top panel of FIG. 27C, oligonucleotides conjugated to enzyme in the enzyme source region can be transported to the positive control region via flow (e.g., free oligonucleotides transported). The positive control region includes embedded substrate. Upon contact of the substrate with the enzyme, a detectable signal may be generated.

Negative controls regions can also be implemented. An example of negative control is shown in the bottom panel of FIG. 27C. In this example, the enzyme source region comprises a similar construction to that shown and discussed above with respect to FIG. 27B. However, the complement of the corresponding tag may comprise a region that is not complementary to the tags. This region reduces (or even eliminates) competition between the authenticating identifier/enzyme oligonucleotide and the tags for the complement. Reduced or eliminated competition for the complement can effectively inhibit or even prevent jettisoning of enzyme oligonucleotides. As they are not free for transport and to interact with substrate in the negative control region upstream, they function as a negative control.

Figure 27D:
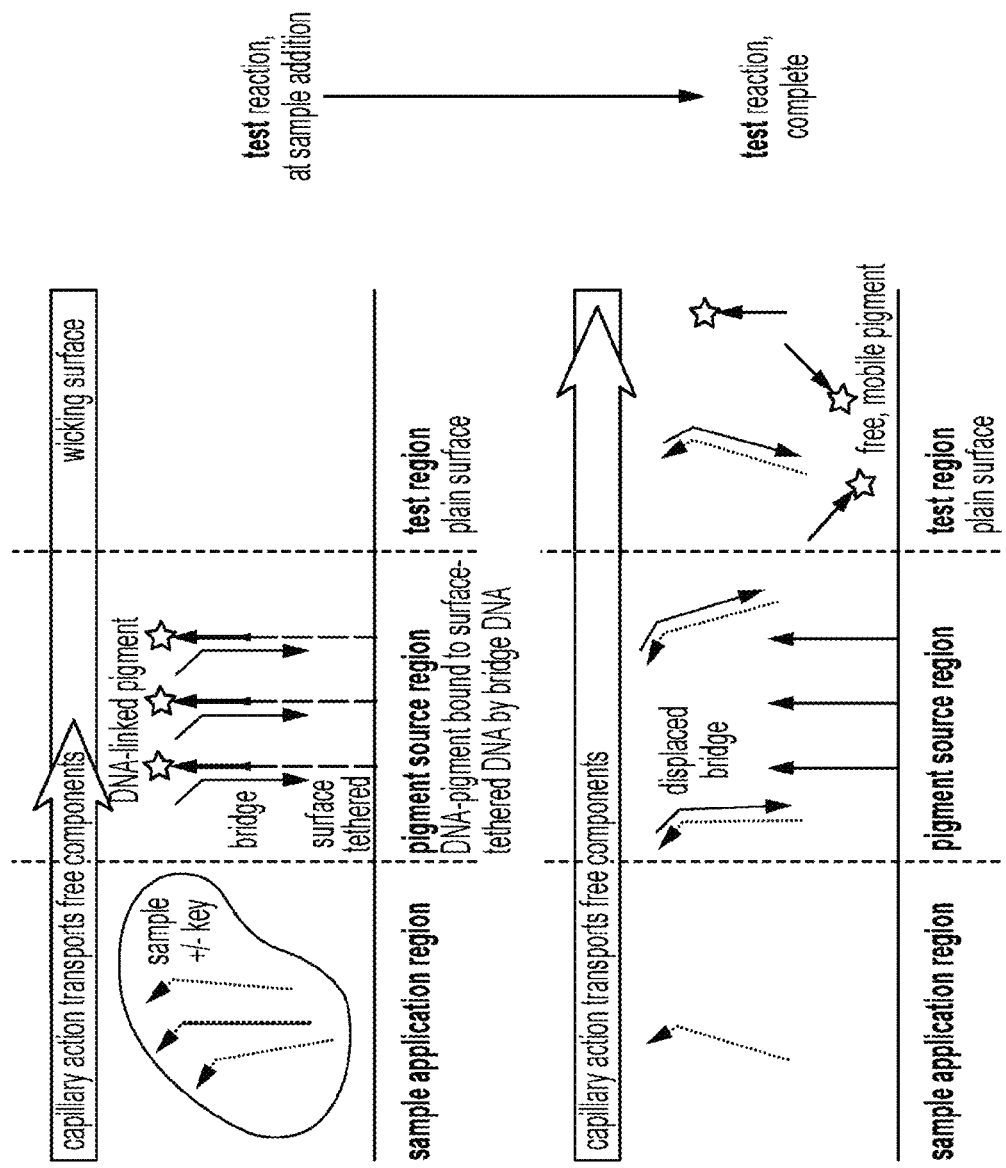
Figure 27E:
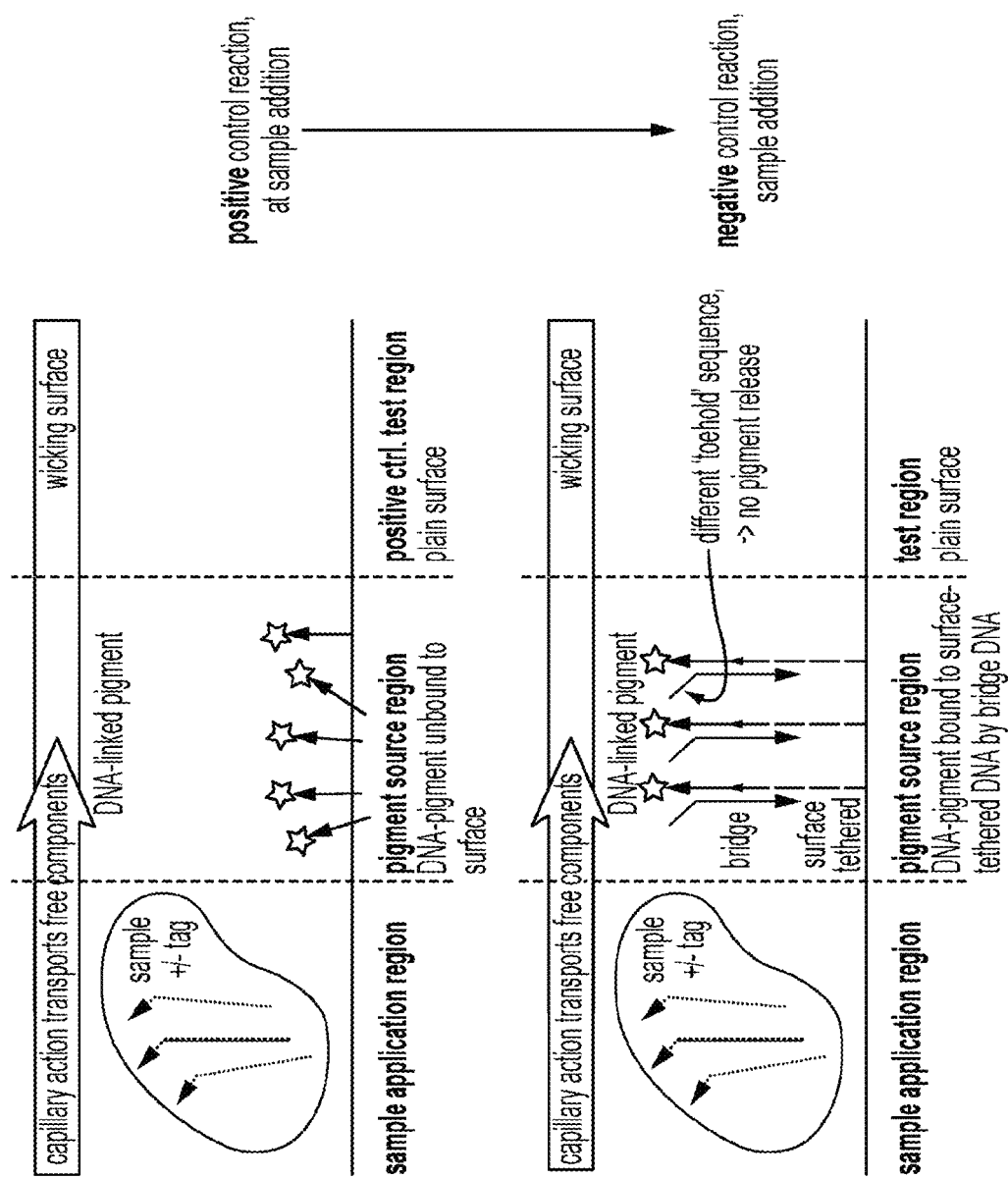

An additional example is provided in FIG. 27D. In this example, colorimetric identification is implemented. This example is analogous to the example of FIG. 27B and discussed above, except that pigment (e.g., dye) is coupled to oligonucleotides in a pigment source region, rather than enzyme in an enzyme source region as in FIG. 27B. Upon displacement of oligonucleotides linked to dye from the pigment source region via interaction of the complexes in the pigment source region with tag, the free mobile pigment is transported to the test region where it be detected (e.g., via colorimetric detection). Analogous positive and negative controls to those for enzyme-catalyzed authentication can also be implemented in colorimetric detection.

Test Substrates

A test substrate as provided herein may be used to authenticate a product of interest, for example, by enabling detection of tags coupled to the product of interest. A test substrate may comprise any wicking material, which enables a solution containing nucleic acids (e.g., DNA), through capillary action, to move from one end of the substrate to another end of the substrate. A test substrate, in some embodiments, comprises paper, such as filter paper. In some embodiments, a test substrate is a strip of paper (elongated paper) or other wicking material having a source region located adjacent to a test region, which is located adjacent to a control region, as depicted in FIG. 1, for example.

Source Region and Detectably-Labeled Strands

In some embodiments, a test substrate comprises a source region that includes detectably-labeled strands, such as enzyme-linked strands or pigment-linked strands (see, e.g., FIG. 27A). Detectably-labeled strands, in some embodiments, are linear nucleic acids (strands) attached to a detectable molecule, such as a fluorescent molecule, an enzyme, or a pigment. Detectably-labeled strands are typically located near (before) the test region on the test substrate such that as a liquid sample moves through a test substrate it first encounters the source region before moving forward to the test region. In some embodiments, the detectably-labeled strands are enzyme-linked strands (e.g., a nucleic acid linked to (e.g., covalently attached to) an enzyme). In other embodiments, the detectably-labeled strands are pigment-linked strands (e.g., a nucleic acid linked to a pigment molecule). The detectable-labeled strands comprise a domain (a particular nucleotide sequence) that binds to (e.g., is partially or wholly complementary to) a domain of a particular tag.

In other embodiments, a test substrate comprises a source region that includes detectably-labeled strands, immobilized source strands, and bridge strands, wherein the bridge strands bind both the detectably-labeled strands and the source strands (see, e.g., FIG. 27B).

Non-limiting examples of enzymes for use as provided herein include glycosidases (e.g., alpha-mannosidase, beta-galactosidase, and alpha-glucosidase), esterases, phosphatases (e.g., acid phosphatase, alkaline phosphatase), arylsulfatases, aminopeptidases (e.g., gamma-glutamylaminopeptidase), and iminopeptidases. In some embodiments, an enzyme is horseradish peroxidase (HRP). Other enzymes may be used as provided herein.

Non-limiting examples of fluorescent molecules (e.g., fluorophores) for use as provided herein include 5-FAM, Calcein, DiO, Fluorescein, FLUO-3, FLUO-4, enhanced green fluorescent protein (EGFP), green fluorescent protein (GFP), Oregon Green 514, QuantiFluor™ dsDNA, QuantiFluor™ ssDNA, QuantiFluor™ RNA, Rhodamine Green, SYBR Gold, SYBR Green, SYTO 9, SYTOX® Green, yellow fluorescent protein (YFP), Alexa Fluor 555, Cy3, Ethidium Bromide, Ethidium Homodimer-1, Propidium Iodide, Resorufin, red fluorescent protein (RFP), Rhod-2, Rhodamine Red, SYTOX Orange, TAMRA, Texas Red, TRITC, Allophycocyanin, Cy5, DRAQ5, SYTOX Red, and SYTOX Blue. Other fluorescent molecules may be used.

Non-limiting examples of pigments for use as provided herein include biological pigments, such as chlorophyll, bilirubin, hemocyanin, hemoglobin, myoglobin, luciferin, carotenoids, phytochrome, phycobiliproteins, melanin, urochrome, and flavonoids. Other pigments may be used.

When enzymes are used to label the detectably-labeled (enzyme-linked) strands, certain color-producing (colorimetric) substrates may be embedded in the test substrate for product authentication. Thus, in some embodiments, a test substrate comprises enzyme-linked strands and embedded colorimetric substrate (specific to the particular enzyme).

Non-limiting examples of colorimetric substrates include alpha 6-bromo-naphthyl, beta 6-bromo-naphthyl, alpha naphthyl, beta naphthyl, p-nitrophenol, o-nitrophenol, 5-bromo-4-chloro-3-indolyl, alpha 4-methoxy naphthyl, beta 4-methoxy naphthyl, bromothymolphthalein, phenolphthalein, 4-methylumbelliferyl, fluorescein, and 7-amino-4-methylcoumarin. In some embodiments, the colorimetric substrate is 3,3',5,5'-tetramethylbenzidine (TMB), 2,2'-azino-bis(3-ethylbenzothiazoline-6-sulphonic acid) (ABTS), or 3,3'-diaminobenzidine (DAB).

In some embodiments, the enzyme is HRP and the substrate is DAB.

The length of a detectably-labeled strand, immobilized source strand, and/or bridge strand, in some embodiments, is shorter than 50 nucleotides, or even shorter than 30 nucleotides. Thus, in some embodiments, the length of a detectably-labeled strand, immobilized source strand, and/or bridge strand is shorter than 45, 40, 35, 30, 25, 20, or 15 nucleotides. In some embodiments, the length of a detectably-labeled strand, immobilized source strand, and/or bridge strand is 10-50, 10-45, 10-40, 10-35, 10-30, 10-25, or 10-20 nucleotides. In some embodiments, the length of a detectably-labeled strand, immobilized source strand, and/or bridge strand is 10, 15, 20, 25, 30, 25, 40, 45, or 50 nucleotides.

Test Region and Test Strands

In some embodiments, a test substrate comprises a test region that includes test strands, which are typically immobilized on (e.g., tethered to) the test substrate. In some embodiments, the test region also includes an embedded enzyme substrate. Test strands comprise a domain that binds to (e.g., is complementary to) a domain of a particular tag. Thus, a particular tag may be designed to bind to both a detectably-labeled strand and a test strand, thereby serving the function of a bridge to link a detectably-labeled strand to a test strand.

The length of a test strand, in some embodiments, is similar to the length of a tag, detectably-labeled strand, and/or control strand. In some embodiments, a test strand has a length of shorter than 50 nucleotides, or even shorter than 30 nucleotides. Thus, in some embodiments, the length of a test strand is shorter than 45, 40, 35, 30, 25, 20, or 15 nucleotides. In some embodiments, the length of a test strand is 10-50, 10-45, 10-40, 10-35, 10-30, 10-25, or 10-20 nucleotides. In some embodiments, the length of a test strand is 10, 15, 20, 25, 30, 25, 40, 45, or 50 nucleotides.

Control Region and Control Strands

In some embodiments, a test substrate comprises a control region (e.g., positive control region) that includes control strands, which are typically immobilized on (e.g., tethered to) the test substrate. Binding of the detectably-labeled strands to the control strands immobilizes the detectably-labeled strands in the control region so that the label can be detected, indicating that the test is complete and acting as a positive control, for example. When the detectably-labeled strands comprise an enzyme (e.g., HRP) and the control region comprises an embedded enzyme substrate (e.g., DAB), the enzyme reacts with the substrate to generate a detectable signal.

The length of each of a control strands in some embodiments, is similar to the length of a tag, detectably-labeled strand, and/or test strand. In some embodiments, a control strand has a length of shorter than 50 nucleotides, or even shorter than 30 nucleotides. Thus, in some embodiments, the length of a control strand is shorter than 45, 40, 35, 30, 25, 20, or 15 nucleotides. In some embodiments, the length of a control strand is 10-50, 10-45, 10-40, 10-35, 10-30, 10-25, or 10-20 nucleotides. In some embodiments, the length of a control strand is 10, 15, 20, 25, 30, 25, 40, 45, or 50 nucleotides.

Nanoparticle Authentication Methods

In some embodiments, one or more authentication strands are conjugated to nanoparticles (e.g., gold nanoparticles). In some embodiments, an individual nanoparticle comprises a set of the same authentication strands (i.e., the authentication strands are identical to one another). In other embodiments, an individual nanoparticle comprises a number of different authentication strands (i.e., the authentication strands are not all identical to one another). In some embodiments, the nanoparticles are present in an authenticating identifier. In some embodiments, when the nanocarriers are present in an authenticating identifier in the aggregated state, the composition appears one color, but changes color when the nanocarriers are in the disaggregated state. In some embodiments, when the nanocarriers are present in an authenticating identifier in the disaggregated state, the composition appears one color, but changes color when the nanocarriers are in the aggregated state. An "aggregated state" as used herein, generally refers to a composition where at least 50%, 55%, 60%, 65%, 65%, 70%, 75%, 80%, 85%, 90%, 95%, 96%, 97%, 98%, 99%, or more of the nanoparticles are linked to other nanoparticles, typically via authentication strands or via authentication strands in combination with tags. A "disaggregated state" as used herein, generally refers to a composition where at least 50%, 55%, 60%, 65%, 65%, 70%, 75%, 80%, 85%, 90%, 95%, 96%, 97%, 98%, 99%, or more of the nanoparticles are not linked to other nanoparticles.

In some embodiments, the nanoparticles are gold nanoparticles having a diameter of less than 50 nm, such as 5 nm, 10 nm, 15 nm, 20 nm, 25 nm, 30 nm, 35 nm, 40 nm, 45 nm, or 50 nm. In one embodiment, the nanoparticles are gold nanoparticles having a diameter of 15 nm. Nanoparticles made of other materials that produce a color change may also be used as provided herein.

Figure 28A:
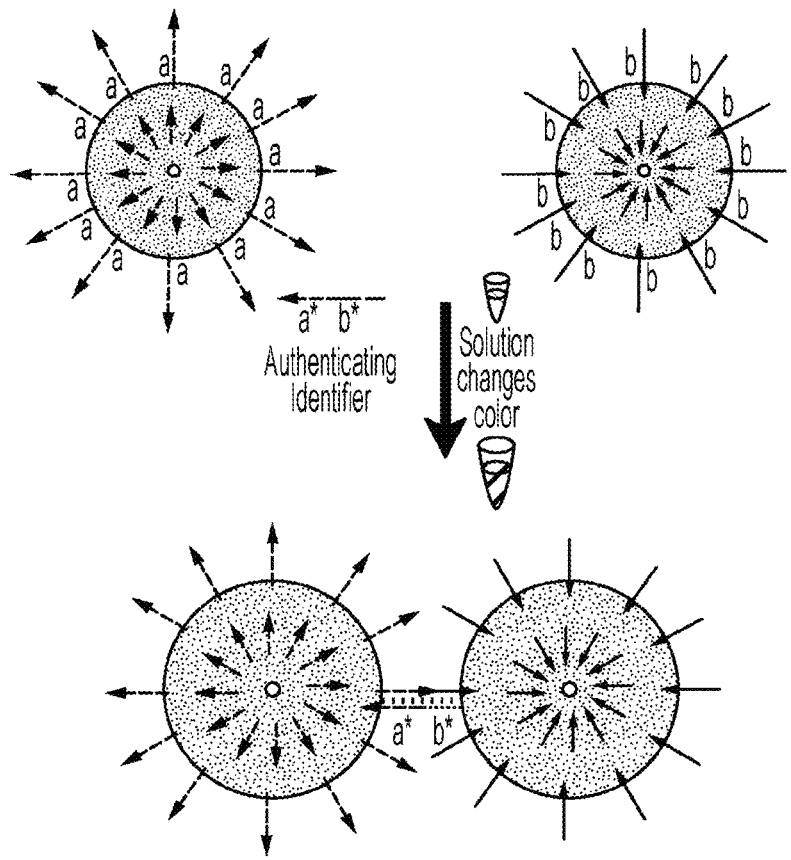
FIGS. 28A-28E illustrate example nanoparticle-based authentication methods.
Figure 28B:
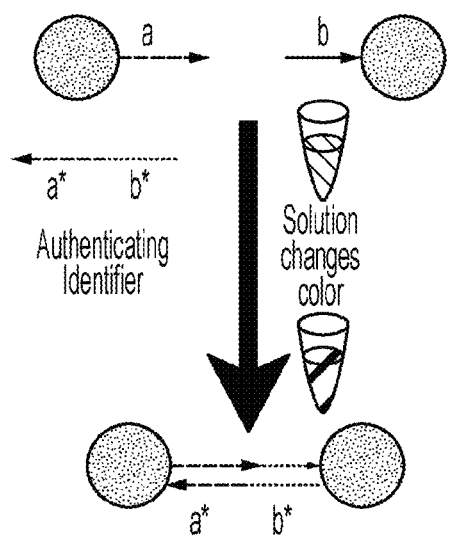
Figure 28C:
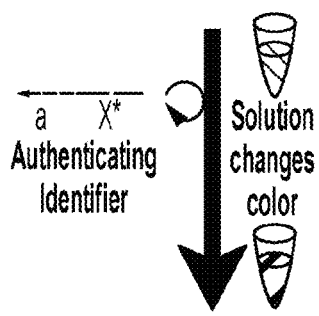
Figure 28D:
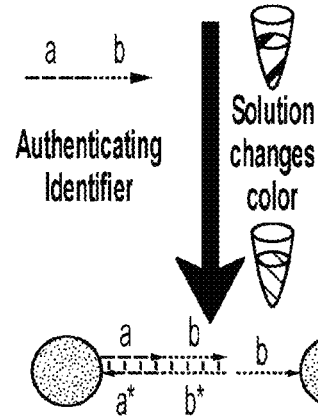
Figure 28E:
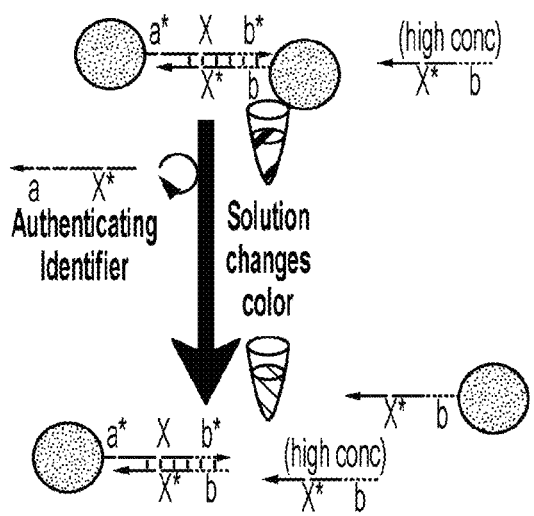

Nanoparticle aggregation and nanoparticle separation assays may be coupled with an authentication method to generate a visual authentication signal. Aggregation or separation of nanoparticles may generate a visual color change in a solution comprising the nanoparticles. Altering the spacing between the nanoparticles (e.g., via aggregation or separation) may generate a visible color shift. FIGS. 28-28D show various methods for nanoparticle-based colorimetric authentication. FIG. 28A shows nanoparticles that are brought together (e.g., aggregated) using the authenticating identifier. The nanoparticles may be bound or linked to a single-stranded tag. Alternatively, a portion of the nanoparticles may be bound to a single-stranded tag and a second portion of the nanoparticles may be bound to a single-stranded hybridization sequence. Both the tag and the hybridization sequence may share sequence complementarity with the authenticating identifier. The authenticating identifier may be single-stranded Addition of the authenticating identifier may enable aggregation of the nanoparticles due to hybridization of one end of the authenticating identifier with the tag and the other end with the hybridization sequence to generate a double-stranded complex. Aggregation of the nanoparticles may generate a visible or colorimetric signal. If the authenticating identifier does not match the tag, nanoparticle aggregation may not occur and a colorimetric signal may not be generated. FIG. 28B shows nanoparticle aggregation promoted using a catalytic authenticating identifier. A portion of the nanoparticles may be bound to a single-stand of a double-stranded tag and another portion of the nanoparticles may be bound to a single-stranded displacement sequence. The nanoparticles comprising the displacement sequence may be present at a higher concentration than the tag bound nanoparticles. The authenticating identifier may share sequence complementarity with a portion of the bound tag and may enable the release of the non-bound portion of the tag. Due to the high concentration of the nanoparticles comprising the displacement sequence, the authenticating identifier may be displaced and the displacement sequence may hybridize to the bound tag, thus providing nanoparticle aggregation.

An alternative to nanoparticle aggregation detection may be nanoparticle separation detection. FIG. 28C shows a strand displacement reaction for separation of nanoparticles. The nanoparticles may be bound together (e.g., aggregated) by the tag. One end of one strand of the tag may be bound to one nanoparticle and one end of the other strand of the tag may be bound to another nanoparticle. In the absence of the authenticating identifier, the two strands of the tag may hybridize and aggregate the particles. The addition of the authenticating identifier may displace one of the strands of the tag and separate the nanoparticles. The separation of the nanoparticles may generate a shift in the color of the solution comprising the nanoparticles. FIG. 28D shows a catalytic authenticating identifier method for separating nanoparticles. Particles may be bound, or aggregated, by the tag, which may be double-stranded. One side of one of the strands of the tag may be bound to one nanoparticle and one side of the other strand of the tag may be bound to another nanoparticle. A solution comprising the nanoparticles may also comprise a displacement sequence present in a higher concentration than the tag or authenticating identifiers. The displacement sequence may not be bound to a nanoparticle. Addition of the matching authenticating identifier may enable displacement of one of the strands of the tag to separate the nanoparticles and generate a signal. The displacement strand may then displace the authenticating identifier to enable the authenticating identifier to displace and separate an additional nanoparticle aggregate.

Figure 29B:
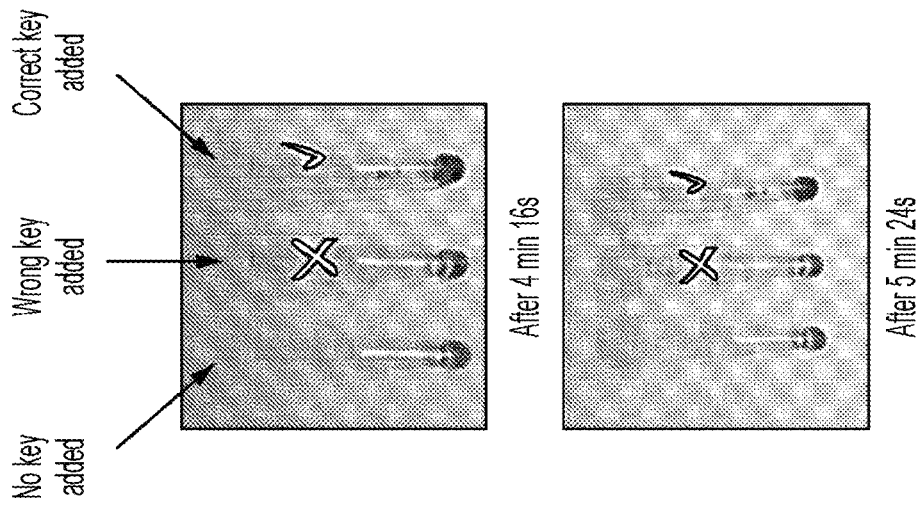
FIGS. 29A and 29B show an experimental example of colorimetric authentication due to nanoparticle aggregation.
Figure 29A:
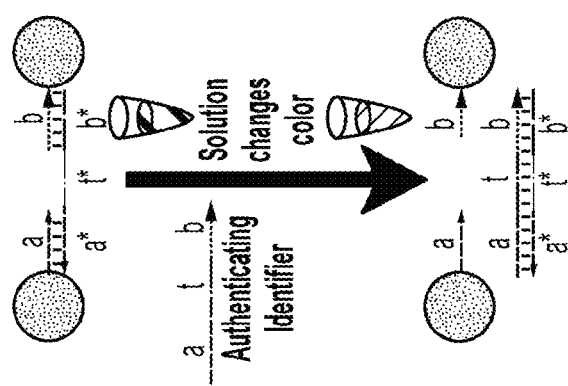

FIGS. 29A and 29B show an example colorimetric authentication method using nanoparticle separation. FIG. 29A show an illustrative schematic of the separation strategy. The nanoparticles are bound to a tag. Each nanoparticle may comprise the same tag. Alternatively, or in addition two, one population of the nanoparticles may comprise one tag and another population of the nanoparticles may comprise a different tag. The tags may be single-stranded tags. The tags may share sequence complementarity with a splint sequence. The splint sequence may hybridize with the tags and aggregate the particles. The authenticating identifier may have sequence complementarity with the splint sequence. Addition of the authenticating identifier may trigger separation of the splint sequence from the tags and hybridization with the authenticating identifier and, thus, separation of the nanoparticles. FIG. 29B shows images taken approximately four minutes and five minutes after addition of a solution comprising either no authenticating identifier, a non-matching authenticating identifier, or a matching authenticating identifier to a solution comprising the aggregated nanoparticles. Both the solutions without the authenticating identifier and with the non-matching authenticating identifier do not show a visible color change. The solution with the matching authenticating identifier added shows a visible color change at both time points.

Figure 30A:
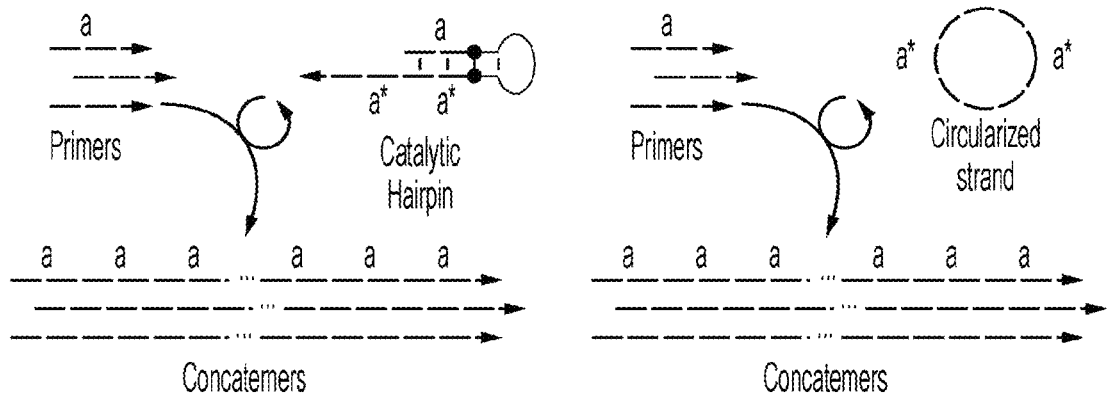
FIGS. 30A-30D illustrates examples of authentication using concatemerization-based aggregation.
Figure 30B:
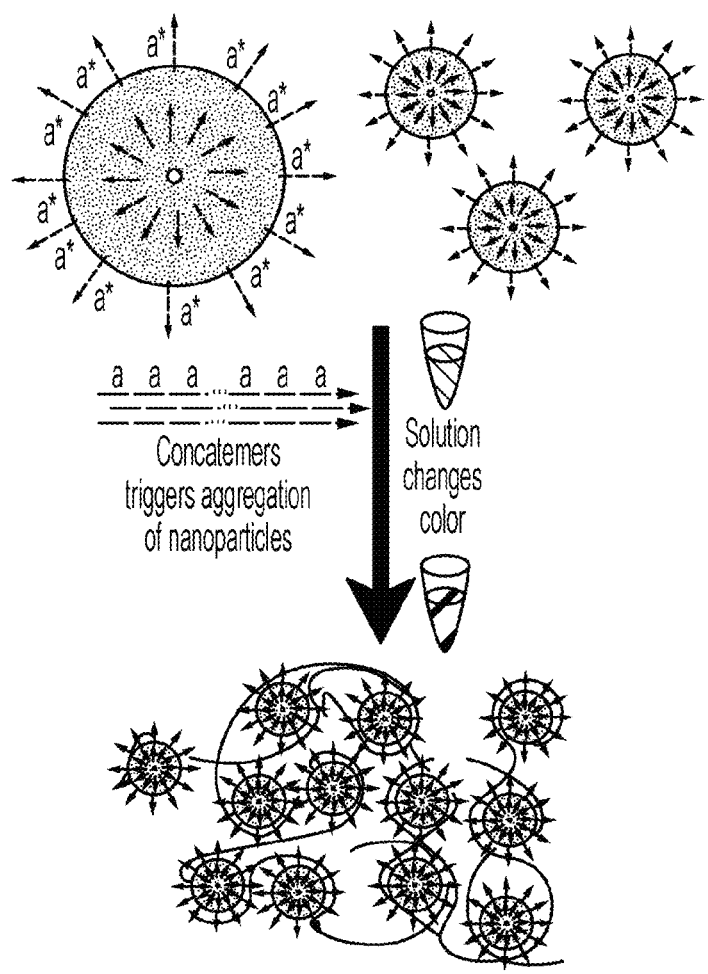
Figure 30C:
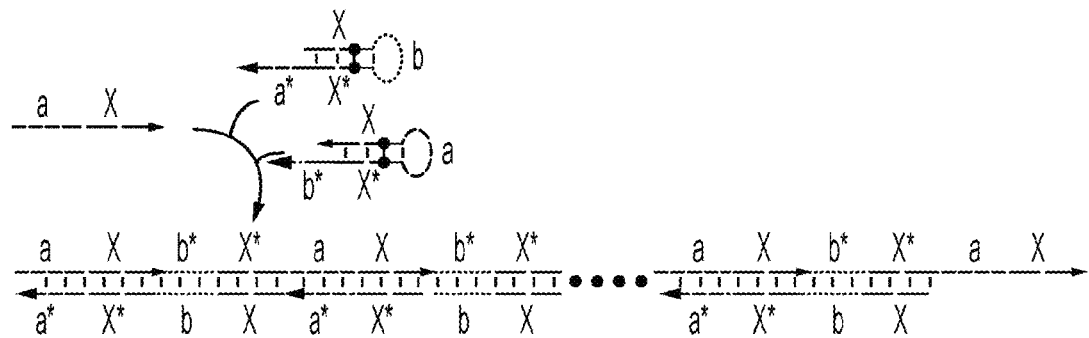
Figure 30D:
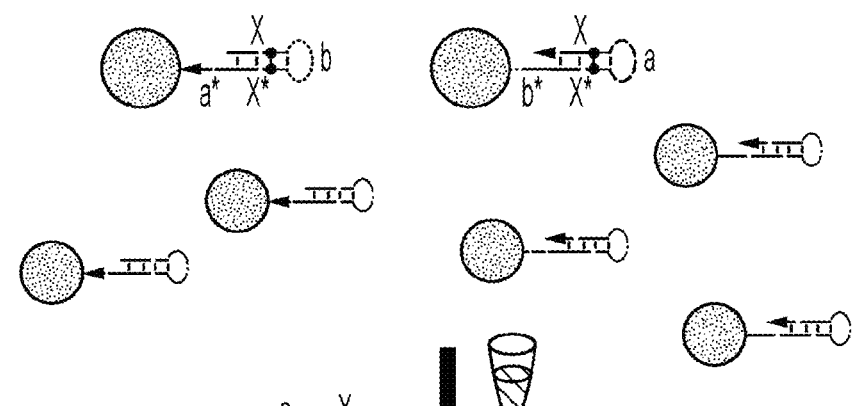
Figure 30D:
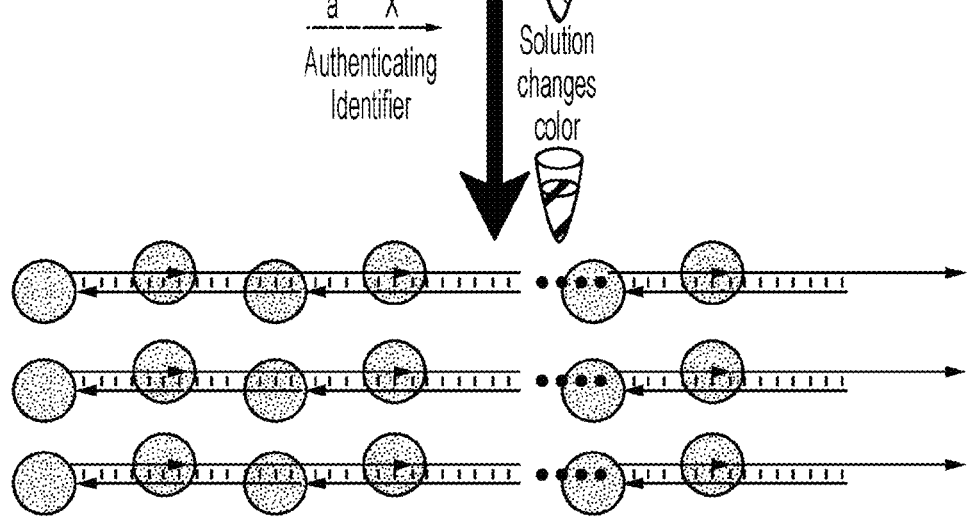

Nanoparticle aggregation may be facilitated through concatemerization. For example, concatemeraization may be used to generate long repeated nucleic acid sequences. FIG. 30A shows polymerization-based concatemerization reactions. A primer exchange reaction (PER) or rolling circle amplification (RCA) may be used to generate long repetitive single-stranded sequences, e.g., concatamers. FIG. 30B shows the use of concatemers to enable nanoparticle aggregation. Nanoparticles may be bound or linked to one or more tags. The tags may be single-stranded tags. The tags may share sequence complementarity with portions of a concatemer. The concatemers may act as scaffolds to trigger aggregation of the nanoparticles. Portions of the concatemers may hybridize with the tags, connecting and aggregating the nanoparticles. Another concatemerization reaction that may be used is hairpin chain reaction, shown in FIG. 30C. Hairpins may be combined with single stranded nucleic acid molecules to form long repetitive double-stranded nucleic acid sequences. FIG. 30D shows the use of hairpin chain reaction for the formation of concatemers comprising nanoparticles. Nanoparticles may be conjugated or bound to one or more tags. The tags may be hairpins. The authenticating identifier may be a single-stranded sequence that enables the hairpin chain reaction. Addition of the authenticating identifier may activate the hairpin chain reaction and generate concatemers that contain the nanoparticles conjugated to the hairpin tags. Formation of the concatemers and aggregated nanoparticles may generate a visual signal.

Figure 31:
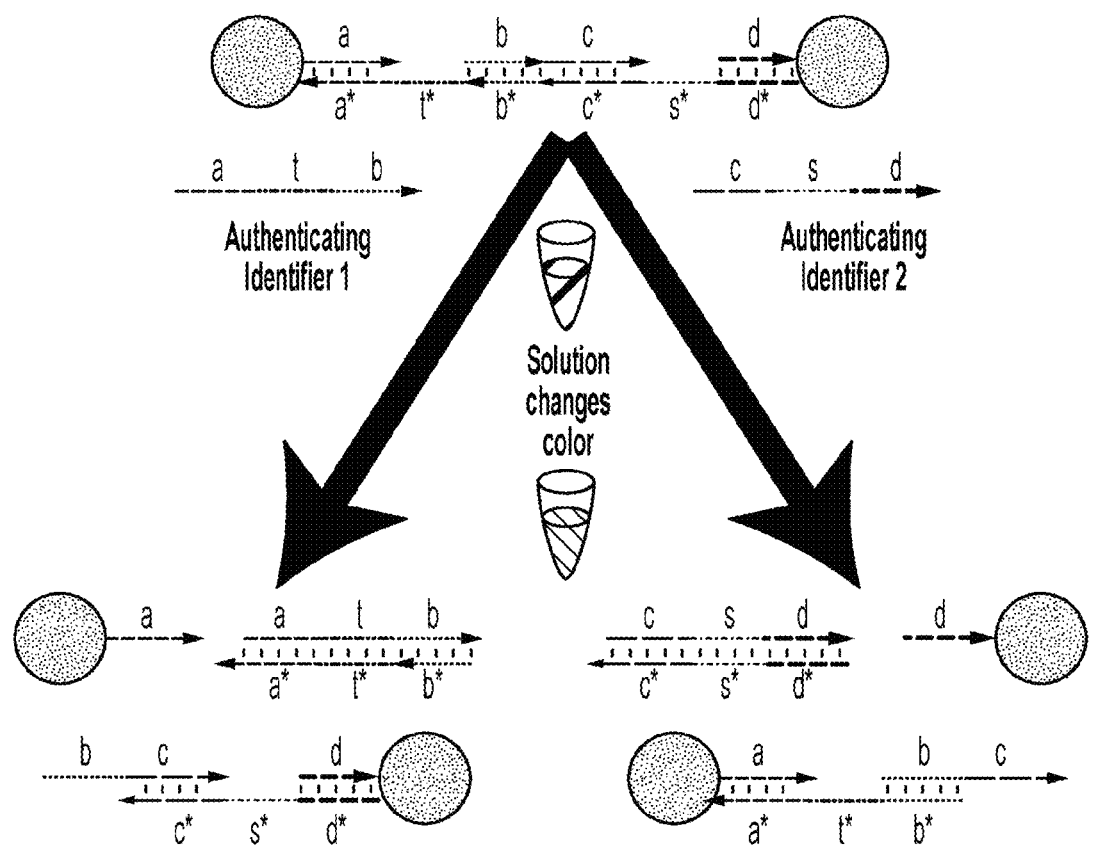
FIG. 31 illustrates an example method of authentication using accelerated nanoparticle separation.

The rate of nanoparticle aggregation and separation and, therefore, signal generation may be increased by providing multiple binding and displacement sites within the tags. FIG. 31 shows an example separation authentication method that uses nanoparticles conjugated to multiple tags and dual authenticating identifiers. A population of the nanoparticles may be conjugated to one double-stranded tag and another population of the nanoparticles may be conjugated to another double-stranded tag. Each tag may comprise a short strand conjugated to the nanoparticle and a long strand hybridized to the short strand. The long strands may share sequence complementarity with a splint oligo. The splint oligo may hybridize with the long strands of both tags and, therefore, aggregate the particles. Two authenticating identifiers may be added to a solution comprising the aggregated nanoparticles. The authenticating identifiers may be single-stranded nucleic acid molecules. The authenticating identifiers may be complementary to the long strands of the tag. Addition of the authenticating identifiers may displace the short strand (e.g., conjugated to the nanoparticle) and the splint oligo to enable the authenticating identifiers to hybridize with the long strands. The displacement may disrupt and separate the aggregation. This authentication strategy may be employed with greater than or equal to 1, 2, 3, 4, 5, 6, 8, 10, 12, 14, 16 18, 20, 25, 30, 40, 50, or more tags. This authentication strategy may be employed with greater than or equal to 1, 2, 3, 4, 5, 6, 8, 10, 12, 14, 16 18, 20, 25, 30, 40, 50, or more authenticating identifiers. The number of tags and authenticating identifiers may be the same or different. There may be more tags than authenticating identifiers. Alternatively, there may be more authenticating identifiers than tags.

Figure 32B:
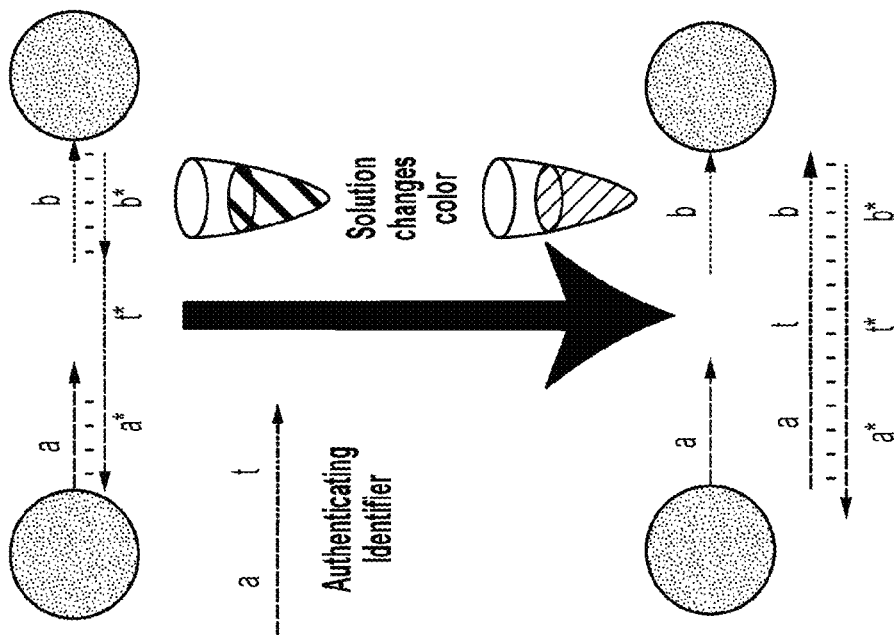
FIGS. 32A and 32B illustrate example methods of authentication using authenticating identifiers that act as primers to permit nanoparticle separation.
Figure 32A:
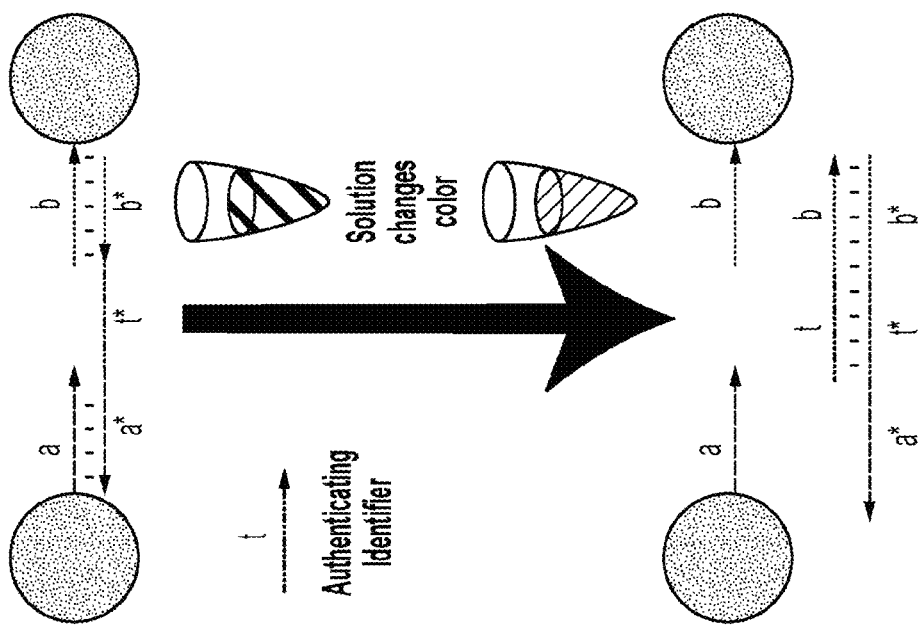

Using authenticating identifiers that act as primers may be another method for increasing nanoparticle aggregation and/or separation and, therefore, rate of signal generation. FIGS. 32A and 32B illustrate example methods of authentication using authenticating identifiers that act as primers to permit nanoparticle separation. FIG. 32A shows an authenticating identifier that enables displacement of a hybridized tag. A pair of nanoparticle may be conjugated with a double-stranded tag. The double-stranded tag may comprise two short strands, with binding domains a and b, and one long strand, with binding domains a*, t*, and b*. Each of the short strands may be conjugated to a different nanoparticle. The long strand may share sequence complementarity with the short strands such that the short strand with domain a hybridizes with the a* domain of the long strand and the short strand with the domain b hybridizes with the b* domain of the long strand, thus facilitating particle aggregation. The authenticating identifier may be a short, single-stranded nucleic acid that acts as a primer. The authenticating identifier may have domain t that is complementary to domain t* of the long strand. The authenticating identifier may hybridize with the long strand of the tag and enable a primer extension reaction, thus causing the nanoparticles to separate. FIG. 32B shows a similar authentication method that uses an authenticating identifier with both a t domain and an a domain. The additional a domain may increase primer specificity by facilitating a branch migration reaction. One or more polymerase enzymes may enable the primer extension reaction. The polymerase enzymes may be free in solution or may be bound to or conjugated to the nanoparticles. Conjugating the polymerase enzymes to the nanoparticles may increase the reaction efficiency.

Figure 33B:
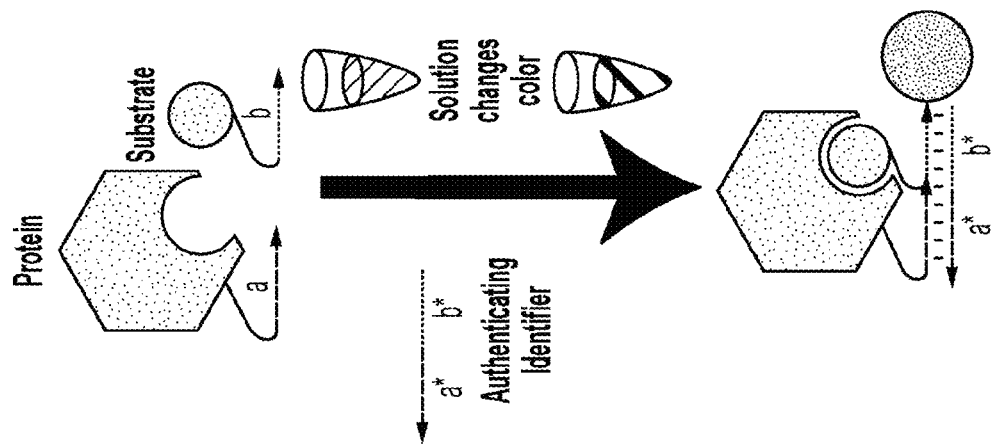
FIGS. 33A and 33B illustrate example methods of authentication using colorimetric protein systems.
Figure 33A:
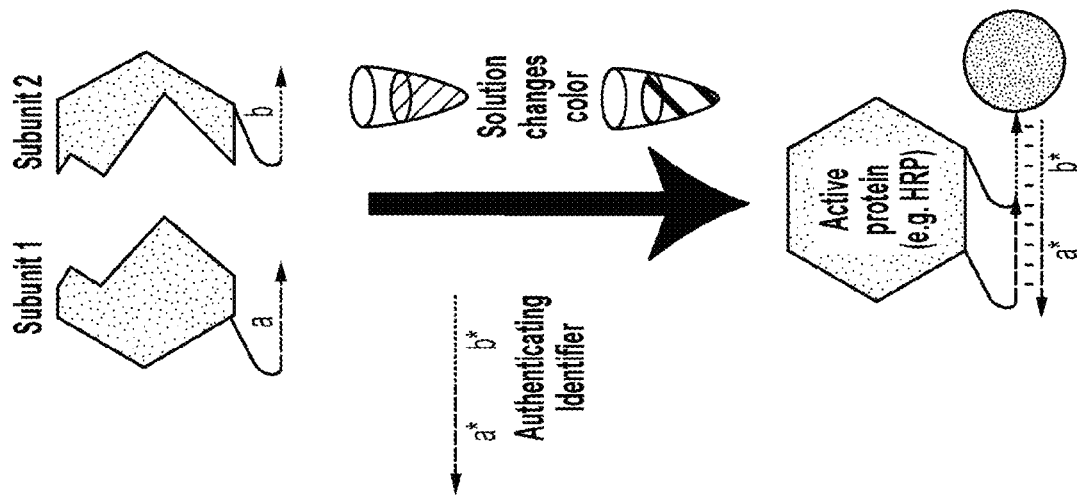

An alternative authentication method may include the use of colorimetric protein systems. Colorimetric protein systems may or may not use nanoparticles to generate a visual color change. FIGS. 33A and 33B illustrate example methods of authentication using colorimetric protein systems. FIG. 33A shows a split-protein colorimetric system. A protein may comprise one or more subunits. The protein may not be active if all of the subunits are not present and coupled. For example, horse radish peroxidase (HRP) may comprise two subunits. Each of the subunits may be bound to an individual tag comprising a single-stranded nucleic acid. The subunits may initially be separate and, therefore, not active. The authenticating identifier may comprise a single-stranded nucleic acid that share complementarity with each of the individual tags. Addition of the authenticating identifier to a solution comprising the HRP subunits may enable hybridization of the tags with the authenticating identifier and coupling of the subunits. Coupling of the HRP subunits may generate an active enzyme. The active enzyme may interact with a substrate to produce a colorimetric product. One or more of the subunits may or may not be bound to a nanoparticle. FIG. 33B shows a protein-substrate colorimetric system in which an individual tag is bound to a protein and another individual tag is bound to a substrate. The authenticating identifier may comprise a single-stranded nucleic acid that share sequence complementarity with the individual tags. Addition of the authenticating identifier may couple to protein to the substrate such that the protein acts on the substrate and a color is generated. Either the protein or the substrate may or may not be conjugated to a nanoparticle.

Figure 34:
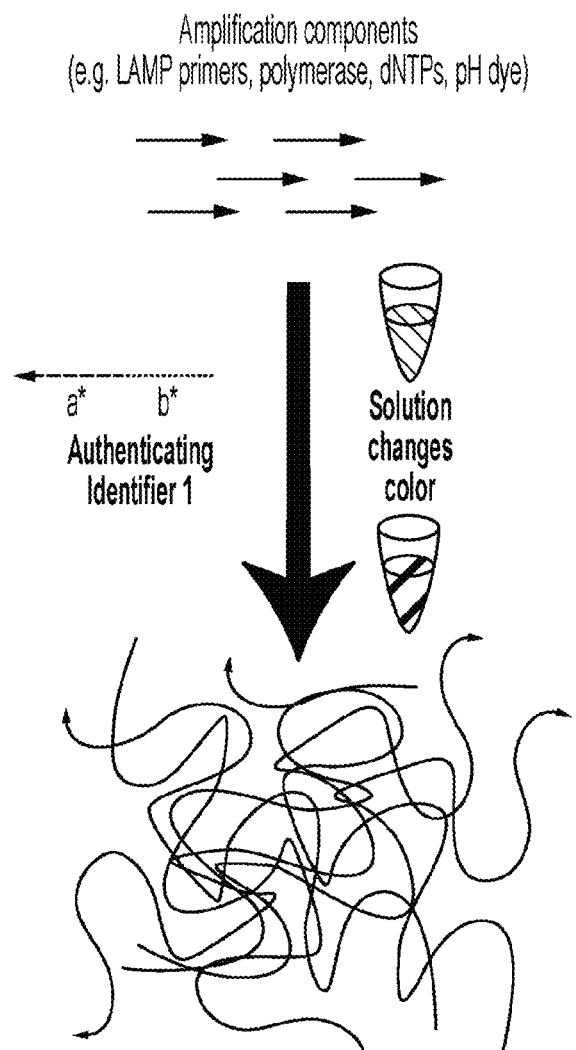
FIG. 34 illustrates an example method of authentication using amplification-based colorimetric signal detection.

Another alternative to a nanoparticle authentication method is the use of isothermal amplification methods to generate colorimetric signals. FIG. 34 illustrates an example method of authentication using amplification-based colorimetric signal detection. The authenticating identifier may trigger isothermal amplification of the tag. The tag may be in solution or may be dried on a label or paper. The authenticating identifier may be in solution and added to the tag. The solution may include primers (e.g., loop mediated isothermal amplification primers), polymerases, nucleotides, pH dye, etc. The authenticating identifier may enable isothermal amplification which, in turn, may generate a colorimetric signal through the use of chemical additives. Chemical additives may include pH dyes or pyrophosphate competitors.

Universal Authentication Methods

Figure 16A:
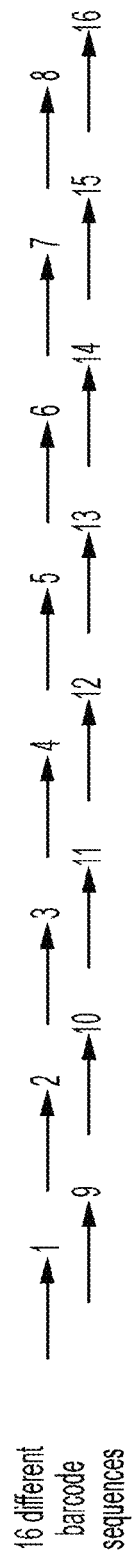

Authentication methods may be personalized or unique to a person, company, or product. Each product may have a unique tag or multiple unique tags. For example, a unique tag may be added to a product at each stage of a supply chain. Each unique tag may have a matching authenticating identifier. To increase the efficiency of authenticating products or items that corresponded to multiple unique tags a universal authentication method may be used. FIGS. 16A-16D illustrate examples of universal authentication methods for the detection of multiple unique tags. FIG. 16A shows an example of sixteen unique tag sequences. The each unique tag sequence may be coupled to the product or item individually or may be assembled into a single tag. The sixteen unique tags may be translated into a sixteen digit binary code sequence (e.g., a barcode). For example, the presence of one of the sixteen tags may correspond to a bit-value of '1' and the absence of the tag may correspond to a bit-value of '0'. Alternatively, or in addition to, the presence of a tag may correspond to a bit-value of '0' and the absence may correspond to a bit-value of '1'. The binary code of the product, or barcode, may be determined by the presences or absences of the individual tags. Each tag may be assigned to a location, or address, in the barcode. For example, the first tag may be assigned to the first bit location, the second tag may be assigned to the second bit location, and so on.

Figure 16B:
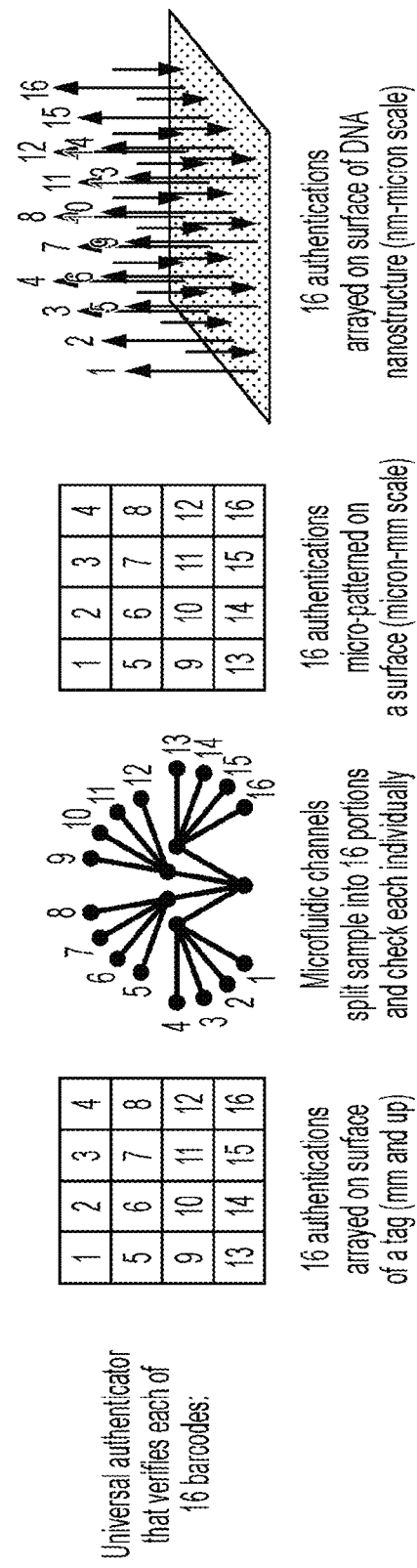

A universal authentication method may detect the presence or absence of each of the sixteen tags. FIG. 16B shows example universal authenticators that may be used to verify the presence or absence of each unique tag. A universal authenticator may include a gridded paper label with sixteen different regions, each associated with a different tag. The regions may be on the centimeter, millimeter, micron, or submicron scale. The authenticator may also be a patterned surface rather than a gridded paper. If the tag is present, a detectable signal may be generated in the corresponding region. In another universal authenticator, a microfluidic device may comprise sixteen different channels each containing one tag. The microfluidic device may be embedded in a paper surface (e.g., in a label). In another example, the universal authenticator may be a surface with the sixteen tags adhered. The tags may form nanoscale structures, such as a DNA origami or DNA brick structure, in the presence of select authenticating identifiers. FIG. 16C shows example detection methods for the sixteen unique tags. The presence or absence of a unique tag may generate a detectable signal. The signal may be colorimetric and detected by eye, fluorescent and detected by a reading device (e.g., microscope), or, in the case of DNA nanostructures, may be detected by DNA paint, atomic force microcopy, or tunneling electron microscopy. The underlying structure is not limited to DNA nanostructures and may include other nanostructures formed by nanoparticles, nanotubes, nanosheets, etc. FIG. 16D shows example binary strings that may be generated from the presence or absence of each tag of the sixteen tags. Though the example shows uses sixteen tags, this universal authentication method may be shrunk to fewer tags or expanded to more tags. For example, the universal authentication method may detect the presence or absence of at least 2, 4, 6, 8, 10, 12, 14, 16, 18, 20, 24, 36, 48, 60, or more tags. The resultant binary readouts may be validated visually, according to a list of valid barcodes, or digitally by checking a computer database with an algorithm capable of verifying valid binary codes.

Fluorescent Molecules and Quenching Molecules

The tag/authenticating identifier systems of the present disclosure include a (at least one) fluorescent molecule, such as a fluorophore. Non-limiting examples of fluorescent molecules include 5-FAM, Calcein, DiO, Fluorescein, FLUO-3, FLUO-4, EGFP, GFP, Oregon Green 514, QuantiFluor™ dsDNA, QuantiFluor™ ssDNA, QuantiFluor™ RNA, Rhodamine Green, SYBR Gold, SYBR Green, SYTO 9, SYTOX® Green, YFP, Alexa Fluor 555, Cy3, Ethidium Bromide, Ethidium Homodimer-1, Propidium Iodide, Resorufin, RFP, Rhod-2, Rhodamine Red, SYTOX Orange, TAMRA, Texas Red, TRITC, Allophycocyanin, Cy5, DRAQS, SYTOX Red, SYTOX Blue and wtGFP.

In some embodiments, the tag/authenticating identifier systems include a (at least one) quenching molecule. Quenching refers to any process which decreases the fluorescence intensity of a given substance. A variety of processes can result in quenching, such as excited state reactions, energy transfer, complex-formation and collisional quenching. Molecular oxygen, iodide ions and acrylamide are non-limiting examples of chemical quenchers. The chloride ion is a quencher for quinine fluorescence.

Supply Chain Authentication and Tracking

Figure 5A:
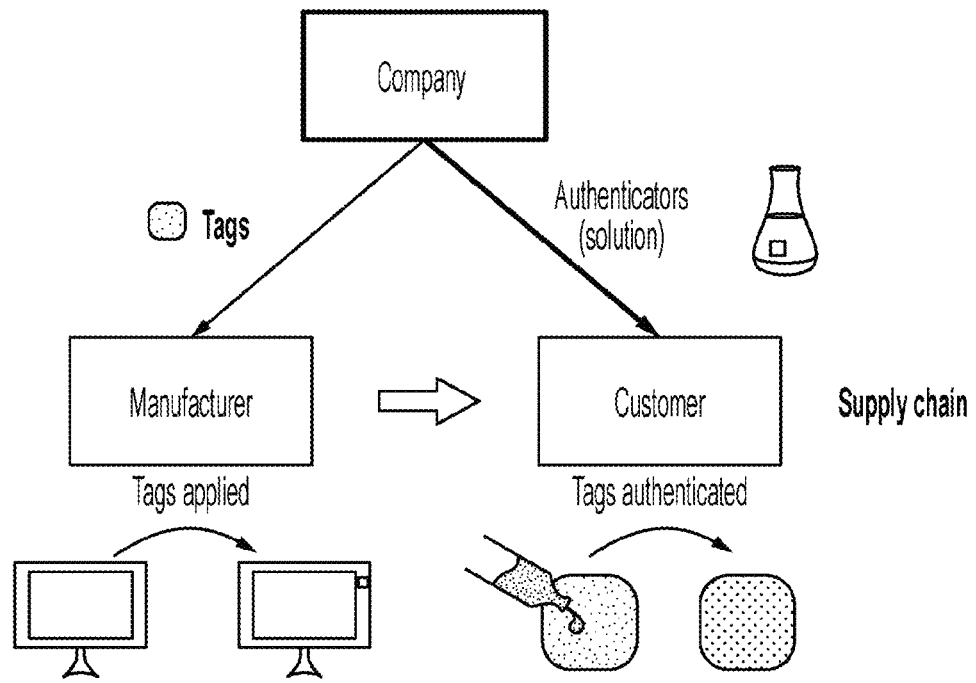
FIGS. 5A-5D illustrate example authentication workflows.
Figure 5B:
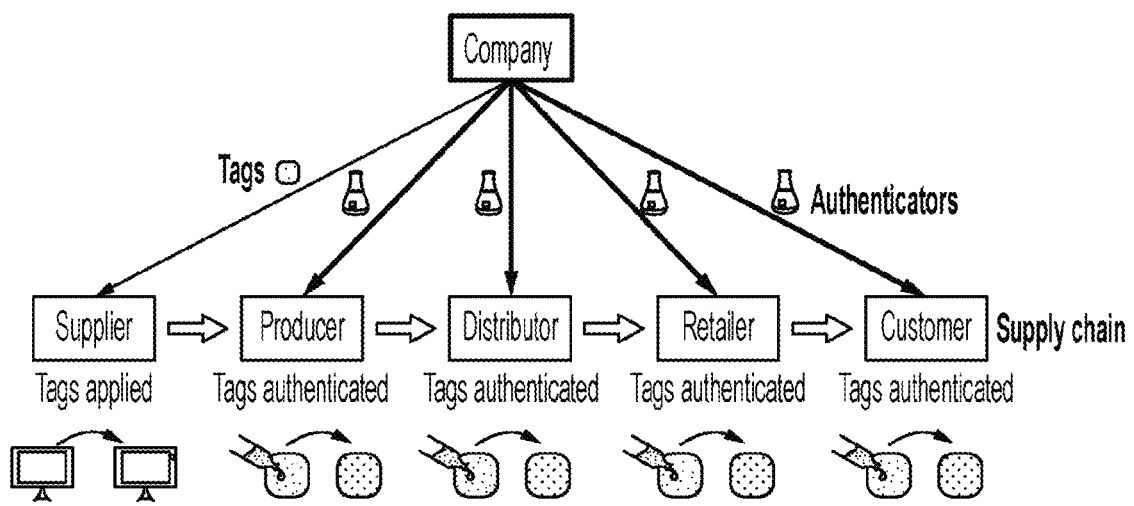
Figure 5C:
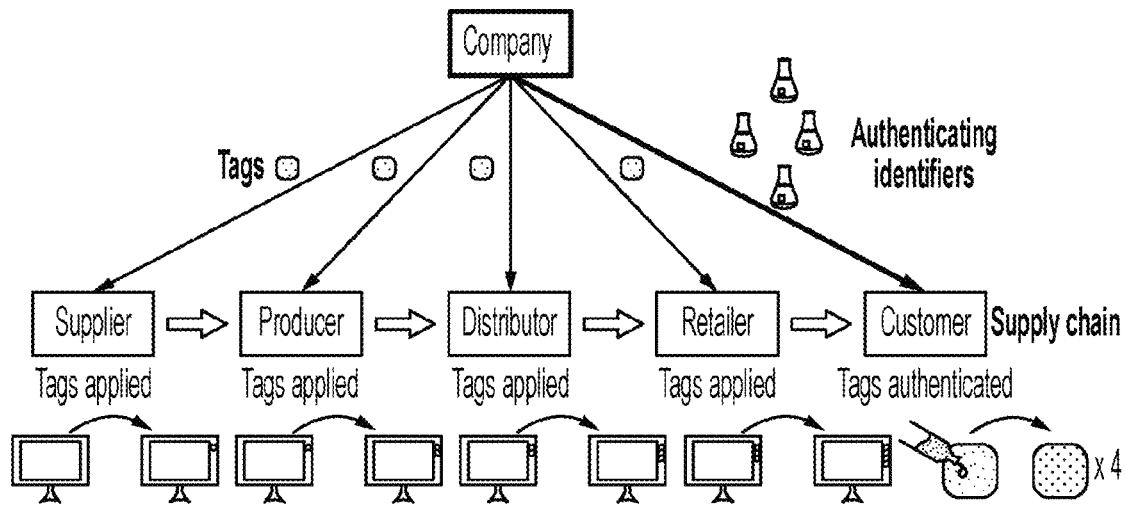
Figure 5D:
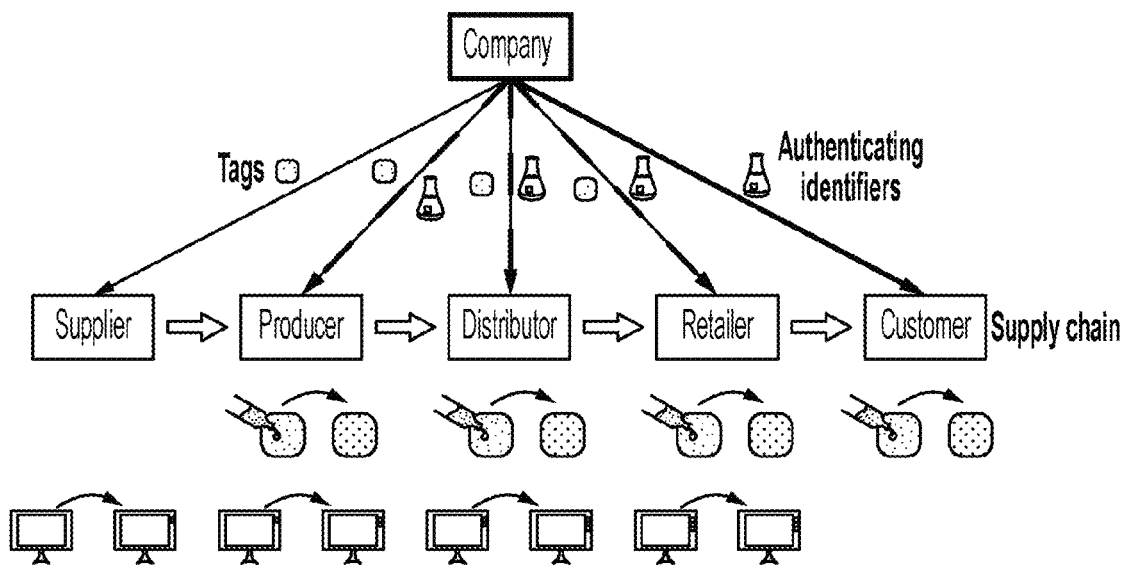

In some embodiments, the tags of the present disclosure are used for supply chain authentication. In many cases, it is useful to validate that multiple steps have been performed during the formulation of a specific product, from raw materials to final packaging. Thus, provided herein are several methods for supply chain tracking in which specific tags or sets of tags can be introduced at multiple (e.g., each) step of a supply chain. Several examples of supply chain authentication and tracking are provided in FIGS. 5A-5D. FIG. 5A shows an example supply chain in which Company A customizes a system that includes a tag and an authenticating identifier. The tag may be distributed to the manufacturer, who applies the tag to a product, product part, or packaging prior to shipment to the customer. An authenticating identifier may be distributed to the customer for use in authenticating the tag and, therefore, the product, product part, or packaging. The tag may be provided to the manufacturer as a label or as a solution or solid phase for addition to the product. The authenticating identifier may be provided as a solution or a solid. The solid may be hydrated prior to authentication. FIG. 5B shows a supply chain that includes a tag or multiple tags that are applied by a supplier to a product, product part, or packaging, and the product, product part, or packaging is authenticated at subsequent steps of the supply chain. This can be achieved using a single re-useable label or several different labels that comprise the same tag. In the case of the re-usable label, the product may be authenticated at each stage of the supply chain and the label may be washed for use in the following step of the chain. In the case of a single use label, the supplier may provide multiple labels with the same tag or different tags and a single label may be authenticated at each stage of the supply chain. In yet another example, a different tag is applied to a product, product part, or packaging at several steps of the supply chain, and the customer authenticates each step at the end of the supply chain (FIG. 5C). In still another example, each step of the supply chain a different tag is applied at and a previously-applied tag is authenticated (FIG. 5D). This supply chain deployment strategy may be customizable so that each step in the supply chain may add a tag and/or authenticate a tag from previous steps of the process, depending on the market need and most vulnerable channels in the supply chain.

Detected signals can be used to alert or notify any party, such as a party in a supply chain, as to the authenticity of the product. Moreover, upon alert or notification, remedial measures (e.g., product replacement, refund, etc.) can be requested by the user or even on behalf of the user (e.g., automatically via a computer system). This may be particularly useful where the requesting party (an upstream distributor, the customer, etc.) discovers from analysis that a product or article is not authentic (e.g., no detectable signal is observed when tag and authenticating identifier are brought together).

The number of tags that can be synthesized is not limited, and tags may include sets of different tags. In some embodiments, a mixture of tags may be introduced to identify different pieces of information about a product. For example, one tag might correspond to the distributor, another to the time period of the batch, and another to the retailer. Alternatively, or in addition, different tags may correspond to different steps along a supply chain pathway, as described previously.

Entities of a supply chain may be anyone involved at any stage/step of the supply chain. Examples include manufacturers and customers. Other examples include, suppliers, producers, distributors, and retailers.

Different chemistries/reaction conditions may be used to authenticate a product, product part, or packaging, including primer exchange reactions, toehold exchange reactions, and ligation reactions, and hybridization chain reactions (see, e.g., International Publication Number WO 2018/057502, published Mar. 29, 2018).

In an aspect, the present disclosure provides a method for product authentication. The method comprises: (a) generating an authenticating pair comprising a tag and an authenticating identifier usable for authenticating a product from a first party by a second party. The product may comprise the tag, tag may include at least one nucleic acid molecule and the authenticating identifier may exhibit binding specificity for the tag. The method also can include (b) providing the tag or information concerning the tag to the first party to effect the first party to produce the product comprising the tag; and (c) providing the authenticating identifier or information concerning the authenticating identifier to a second party. Interaction between the tag and the authenticating identifier exhibiting binding specificity for the tag may yield a detectable signal that is indicative of authenticity of the product. The tag may be provided to the first party and/or the authenticating identifier may be provided to the second party in any suitable form, including a solid, a semi-solid, a liquid (e.g., solution form) or a vapor.

Generating an authenticating pair can include selecting a tag from a plurality of tags and selecting an authenticating identifier from a plurality of authenticating identifiers. In some embodiments, the authenticating identifier exhibits binding specificity for the tag. In some embodiments, the authenticating identifier may not exhibit binding specificity for other tags from the plurality of tags. Furthermore, information concerning the tag and/or authenticating concerning the authenticating identifier may be provided to the first party and second party, respectively, in electronic format. In some embodiments, electronic information can be provided via a computer system and/or over an electronic network, including with an example computer system described elsewhere herein.

As described elsewhere herein, a tag or the authenticating identifier may comprise a nucleic acid molecule that has a structure such that the nucleic acid molecule cannot be identified by sequencing. For example, the nucleic acid molecule may comprise one or more of a nucleic acid enantiomer, a backbone modification, a covalent modification to a base of the nucleic acid molecule that may modulate hybridization of the base to another base, or at least one unnatural base pair. Furthermore, as described elsewhere herein, an authenticating identifier can include at least one nucleic acid molecule that exhibits sequence complementary to the tag. The first party and the second party may be members of a supply chain. For example, the first party may be a party (e.g., the product manufacturer, a distributor, a retailer, a contract manufacturer organization (CMO), any party authorized to produce the product, etc.) upstream from a customer in the supply chain. The second party may be a party (e.g., a contract manufacturer organization (CMO), a supplier, a distributor, a retailer, a customer) downstream from the product manufacturer.

In some embodiments, the product further comprises one or more additional tags and the tag such that the authenticating identifier does not exhibit binding specificity for the one or more additional tags. For example, the product may further comprise at least about 10, 30, 50, 100, 300, 500, 1000, 3000, 5000, 10000, 30000, 50000, 100000 or more additional tags for which the authenticating identifier does not exhibit binding specificity.

Primer Exchange Reaction

Figure 7B:
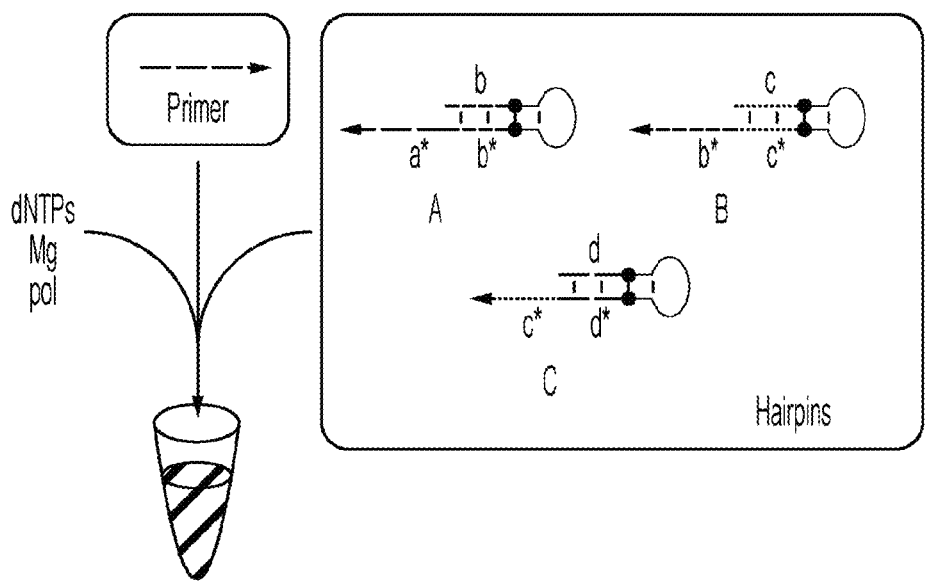
Figure 7C:
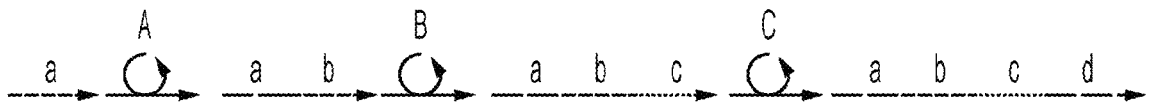

Tags may be generated using one or more primer exchange reactions. FIGS. 7A-7C depict an example of a primer exchange system for producing one or more tags. The hairpin components may be introduced at each stage of the supply chain pathway. FIG. 7A shows an example three step supply chain pathway with a unique hairpin component being added at the completion of each step. For example, a manufacturer, distributor, or retailer may add a hairpin component prior to forwarding the product to the next step in the supply chain (e.g., to the customer). These hairpin components may be combined with a primer, dNTPs, and a strand displacing polymerase (FIG. 7B) to synthesize a multi-domain strand (FIG. 7C). The complete multi-domain strand may function as a tag, which can be authenticated, as provided herein, using an authenticating identifier. The primer exchange reaction (see, e.g., WO 2017/143006, published Aug. 24, 2017, incorporated herein by reference in its entirety) may be performed at the end of the supply chain or at each step of the supply chain. The multi-domain tag may provide information regarding the steps of the supply chain. For example, the multi-domain tag may indicate at which facility a product is manufactured or assembled, which distribution centers the product passed through, and/or which retailer sold the product.

Toehold Exchange Reaction

Figure 8B:
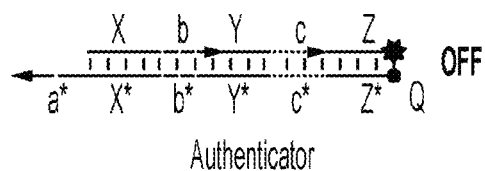
Figure 8C:
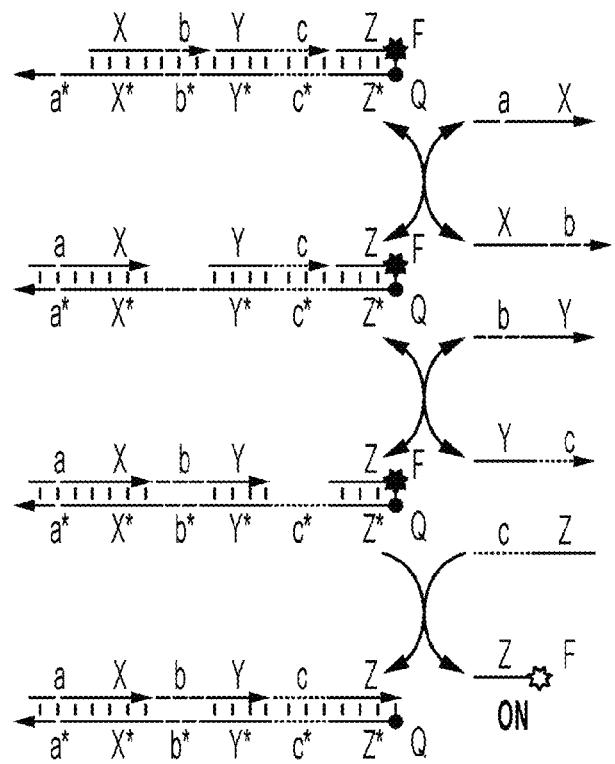

Toehold exchange reactions may be used to generate a signal indicative of authentication. FIGS. 8A-8C depict an example of a hybridization-based system, where an oligo (e.g., single linear strand) is introduced at different (e.g., each) steps of a supply chain pathway and toehold exchange-based supply chain authentication is used. FIG. 8A shows oligoes that are added at each step along the supply chain pathway. The oligos may be single-stranded or may be double-stranded. The oligos may be linear or may include secondary structure, such as hairpins. The oligos may be combined into a single strand or may not be combined. The tag may comprise all the oligos added at the different stages of the supply chain. A nucleic acid complex with several strands and a quenched fluorophore on one of the ends (FIG. 8B) may be used to confirm authenticity, through several toehold exchange reactions (see, WO 2012/058488, published May 3, 2012, incorporated herein by reference). The complex may be in an 'OFF' configuration when the fluorophore is quenched (e.g., authenticity not verified). The several toehold exchange reactions may result in a detectable signal (FIG. 8C), or 'ON' configuration, indicating that the product is authentic. The toehold exchange reaction may not reach completion (e.g., not generate a detectable signal) unless all of the single stranded oligos are present. For example, the supply chain pathway may include a manufacturer, distributor, and retailer, each of which incorporates an oligo into the authentication system. The toehold exchange reaction may include a complex that binds to each of the oligos from the manufacturer, distributor, and retailer. If one of the oligos is not present in the tag, the toehold exchange reaction may not permit displacement of the quencher or fluorophore strand and a detectable signal may not be generated, indicating that authentication may not be completed.

Ligation Reaction

Ligation may be an alternative method for generating tags. FIGS. 9A-9B depicts another example of a ligation-based authentication system. FIG. 9A shows a tag component (e.g., oligo) that may be added at each stage of the supply chain pathway. The tag component may be single-stranded or may be double-stranded. The tag component may be linear or may comprise secondary structure, such as a hairpin. The tag components may be combined at each stage of the supply chain or at the end of the supply chain. At the end of the supply chain, for example, the tags may be combined with splint strands in a ligation reaction to synthesize a multi-domain strand (FIG. 9B). The complete multi-domain strand may function as a tag, which can be authenticated, as described elsewhere herein, using an authenticating identifier. A complete tag sequence (e.g., a-b-c) may be generated if all of the oligos from the supply chain are present. The tag may be authenticated using any of the methods described herein. The ligated tag may be purified or may not be purified.

Hybridization Chain Reaction

Hybridization chain reactions may be used when generating tags (see, e.g., Evanko, D. Nature Methods, 1, 186-187, 2004). This series of reactions relies on hybridization events between complementary sets of DNA hairpin molecules. In some aspects, two species of DNA hairpins remain unassociated in solution until the introduction of initiator strands to trigger a chain of hybridization reactions. The DNA monomers may then self-assemble to yield diverse DNA polymers.

Consumable Product Authentication

Tags may be used for authentication of consumable products. Consumable products may be foods (e.g., produce, meats, processed foods, etc.) or goods (e.g., soaps, toothpastes, detergents, toiletries, etc.) FIGS. 10A-10C illustrate methods for plant product authentication. FIG. 10A shows containers comprising unique tags that may be provided to different producers, distributors, or other actors. The container may comprise an application method. Application methods may include spraying, painting, dipping, stamping, or any other application method. FIG. 10B shows application of the tags by spraying the tags onto the product. The product may be produce or any other edible item. The solution comprising the tag sequences may be non-toxic and may not be washed prior to consuming the product. The solution comprising the tag may be water soluble and may be easily removed with washing. The solution comprising the tag may not be removed with water, but may be removed with a detergent or solubilizing agent. FIG. 10C shows multiple products that may be re-packaged such that the tag sequences may remain with the plant products and can be recovered using any of the authentication procedures described herein. The products may be labeled with information from the producer, distributor, or retailer. For example, the producer may label the produce with a tag that is indicative of the origin of the produce and the date harvested. The distributor may label the produce with the batch in which the produce was received and/or distributor information. The retailer may label the produce with date of receipt and inventory specific information.

Tag Domain Designs

Figure 11A:
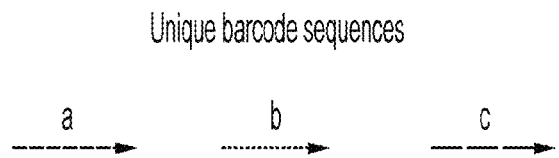
FIGS. 11A-11D illustrate tag domain designs.
Figure 11B:
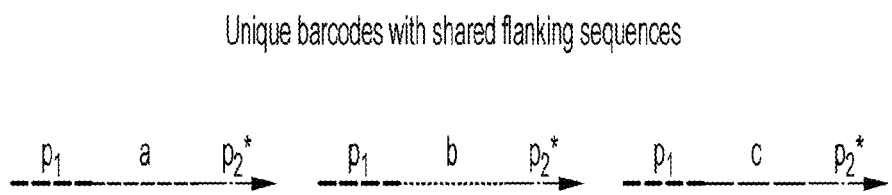
Figure 11C:
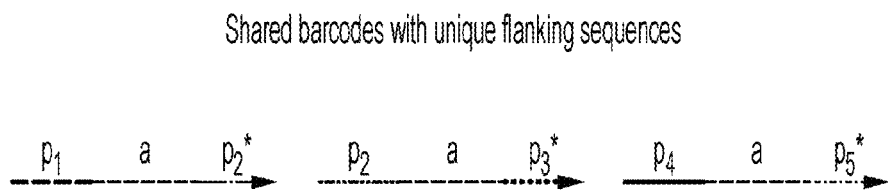
Figure 11D:
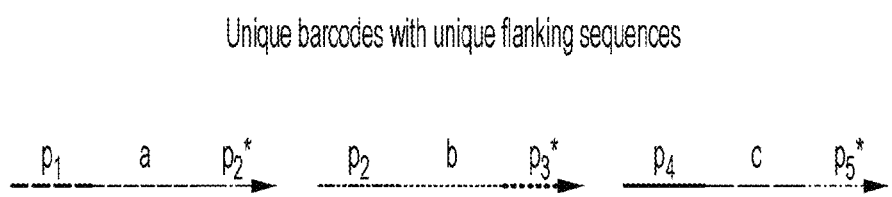

Tags may be generated or assembled using any method disclosed herein (e.g., using PCR or ligation). Tags may comprise unique and shared sequences. For example, tags may comprise shared flanking sequences. FIGS. 11A-11D illustrate example tag domain designs. FIG. 11A shows three unique tag sequences, denoted as a, b, c, that may be used to label three items. Each item may be labeled with a unique tag or each item may be labeled with a combination of the unique tags. FIG. 11B shows unique tag sequences that share one or more common sequence components, such as flanking sequences on either or both sides of unique tag sequences. The flanking sequences may serve as primer binding sites for amplification. The flanking sequences may be present on a single end or on both ends of the unique tag domains. Each tag may share the same flanking sequence or a portion of the tags may share the same flanking sequence and, thus, allow for selective amplification of the tags. FIG. 11C shows that unique tag sequences that contain identical (or no) oligo sequences between unique pairs of flanking sequences. The unique flanking sequences may enable a unique pair of amplification primers to amplify a select tag. FIG. 11D shows that different unique tags may contain unique flanking sequences on either or both sides of a unique oligo. Each tag may comprise a unique oligo sequence. Each tag may also comprise one or more flanking sequences. The flanking sequences may be unique (e.g., not shared) between the tags. Alternatively, or in addition two, the tags may comprise flanking sequences on one end that are unique and the other that are shared. The tag designs may allow for selective amplification or purification of individual tags from a pool of tags.

Tag Amplification and Ligation

Figure 12A:
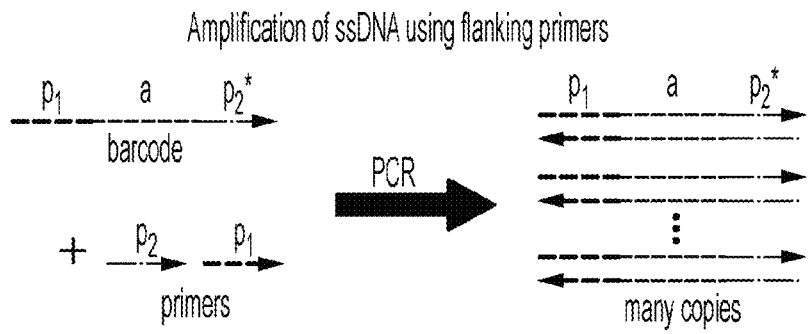
FIGS. 12A-12D illustrate example amplification and ligation strategies.
Figure 12B:
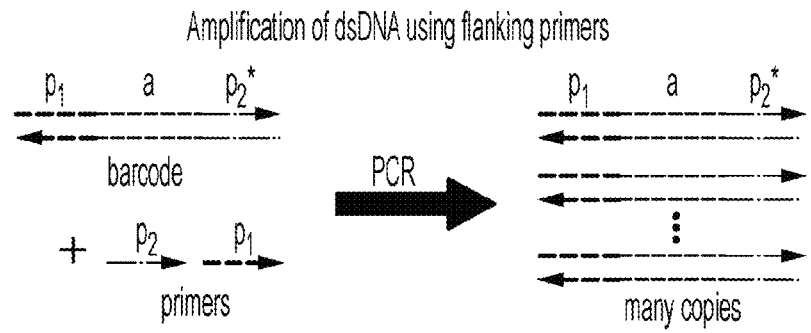
Figure 12C:
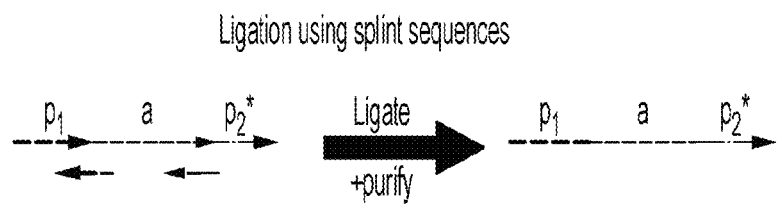
Figure 12D:
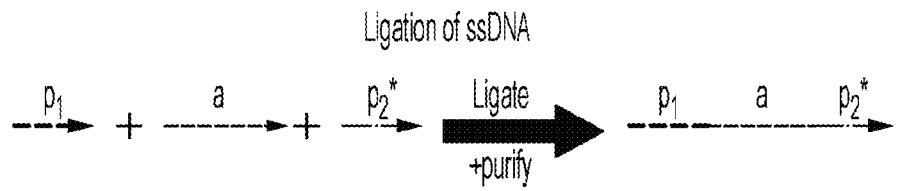

Tags may be synthesized, assembled, copies, and disassembled. Tags may be generated via base-by-base synthesis or by assembling component parts. A small amount of tags may be generated by base-by-base synthesis and the tag may be copies or amplified using polymerase chain reaction (PCR). Alternatively, or in addition to, tags may be generates from the assembly of short oligo sequences into a longer nucleic acid sequence. The short oligo sequences may be assembled using ligation. FIGS. 12A-12D illustrate example amplification and ligation strategies for generating and copying tags. FIG. 12A shows primers that are combined with single-stranded tag sequences to permit amplification (e.g., using PCR and thermal cycling). The tags may include shared flanking sequences that are complementary to a select primer. Alternatively, a portion of the tags may comprise a shared flanking sequence such that a portion of the tags share complementarity with a select primer sequence. The tags and primers may undergo PCR and thermal cycling to amplify (e.g., copy) the tags. FIG. 12B shows amplification of double-stranded tags. As with single-stranded tags, the tags may include shared flanking sequences that are complementary to a select primer. The primer may hybridize with a portion of a tag and permit a primer extension reaction to copy the tag. All of the tags may comprise a shared flanking sequence or a portion of the tags may comprise shared flanking regions. In an example, a portion of the tags comprise a first flanking sequence and another portion of the tags comprise a second flanking sequence. The tags may comprise any number of shared flanking sequences, such as greater than or equal to 1, 2, 3, 4, 5, 6, 8, 10, or more shared flanking sequences. The flanking sequences may allow for selective amplification and purification of the tags. FIG. 12C shows ligation of tag components without flanking sequences. Ligation may be used to combine tag components to generate tags. The tag components may be ligated using splint sequences that are complementary to the ends of select tag components. The tag components may be assembled and ligated in a random or non-random order. The split sequences may facilitate ordered assembly of the tags. FIG. 12D shows ligation of tag components using flanking sequences. The tag components may comprise flanking sequences. The flanking sequences of one tag component may be complementary to a flanking sequence of another tag component. The flanking sequences may enable ligation of the tag components to generate tags. The tag components may be assembled randomly or assemble in an order. The tags may be purified after amplification or assembly or may not be purified.

Timing and Temperature of Amplification

The tag that is to be authenticated may be present in the liquid, solid, or product at sufficient amounts (or quantities) as to generate detectable (e.g., visible) signal(s) after direct authentication. In some embodiments, a tag and/or a signal may be amplified prior to, during, or after authentication. In some embodiments, a tag may be amplified (e.g., through the use of PCR). In some embodiments, a signal may be amplified (e.g., through amplification of a detectable signal, e.g., through use of mechanical, electrical, or chemical approaches). In some embodiments, amplification of a tag or signal is performed in order to detect a tag or signal. In some embodiments, amplification is performed before the authentication step, providing more input signal to the authentication reaction. In other cases, it may be done after sequence authentication, enabling a low authentication signal to be read or interpreted. In some embodiments, nucleic acids are amplified in a sequence-dependent manner (e.g., using primer-tag complementarity), enabling the amplification itself to be wholly or at least partially authenticating.

Tag signals that are amplified before authentication are generally copies of the tag sequences themselves, or are closely or directly derived sequences (i.e., in a deterministic 'translation,' such that downstream authentication of sequence continue to reliably indicate an authentic tag). Alternatively, signals amplified after authentication may be any resulting nucleic acid signals or other physical, chemical, or electrical signals.

Components required for any amplification scheme may be included in a solution, into which the tag in question is added. Addition of tag into a solution comprising components required for any amplification scheme may initiate an amplification reaction. Alternatively, a solution comprising components required for any amplification scheme, which may further comprise a tag, may be freeze-dried and stored prior to a later reconstitution with water, a liquid product, or another solution. In other embodiments, wet or dry components that make up said solution may be included in a 'microfluidic' device of paper, PDMS, or other material. In this manner, the order or timing of amplification, authentication, and signal display may be controlled.

Nucleic acid amplification or signal amplification may generally be carried out at constant temperature ('isothermal'), which may reduce the use of complex external equipment. In some embodiments, isothermal techniques may operate optimally at ambient and/or room temperature. In some embodiments, ambient and/or room temperature is about 20 to 25° C. In other embodiments, isothermal techniques may operate optimally at temperatures below room temperature (e.g., about 15° C., about 10° C., about 4° C.). In other embodiments, isothermal techniques may operate optimally at temperatures below room temperature (e.g., about 30° C., about 37° C.). In such embodiments, a simple heating source may be employed, optionally contained within the same device required for readout (e.g., device for reading fluorescence or quantifying signal). In some embodiments, a simple heating source may be a light source or a chemical source that generates heat. In some embodiments, isothermal temperature may be regulated by a body temperature.

In some embodiments, nucleic acid amplification or signal amplification may be performed at different or varied temperature. In some embodiments e.g., when using PCR for amplification, a multiple-temperature device may be used. A multiple-temperature device may be a Peltier-based device, or any other device that may incubate samples or solutions of tags between fixed temperature zones.

Enzymatic Amplification

In some embodiments, nucleic acid amplification may be performed using any possible enzymatic method. An example enzymatic method generally utilizes a polymerase, optionally a strand-displacing polymerase, and/or other enzymes to generate free 3' ends for nucleotide extension. Enzymatic methodologies include but are not limited to Polymerase Chain Reaction (PCR), Loop-Mediated Isothermal Amplification (LAMP), Rolling Circle Amplification (RCA), Recombinase Polymerase Amplification (RPA), nick and extend-type schemes (wherein double-stranded DNA is repeatedly nicked by an endonuclease and extended by a strand displacing polymerase), and signal amplification by exchange reaction (SABER). In some embodiments, an enzymatic methodology may increase DNA linearly with time. In some embodiments, an enzymatic methodology may produce polynomial (e.g., quadratic) or geometric (exponential) amplification. In some embodiments, multiple enzymatic methodologies may be used.

Non-Enzymatic Amplification of Nucleic Acids

In some embodiments, a tag or signal may be amplified using non-enzymatic methodologies. Dynamic nucleic acid, e.g., DNA, circuits can be generated that rapidly change state in the presence of a nucleic acid 'trigger.' The trigger may be the tag itself, or another species downstream of authentication. The nucleic acid amplification circuit constitutes a 'kinetically-trapped' system of species that converts to a system at a lower thermodynamic potential energy, but contain no traditional chemical enzymes that alter covalent bonds. Example triggers may include those in Yin, P. et al., *Nature*, 451(7176):318-22, 2008; and Zhang, D. Y. et at, *Science* 318(5853):1121-5, 2007.

Methods of Non-Nucleic Acid Signal Amplification

During or after authentication, signals may be directly converted to a non-nucleic acid signal such as the presence of a gold or other nanoparticle or enzyme. In some embodiments, localization of a gold nanoparticle of 5-250 nm diameter to a particular position on a Lateral Flow Device (LFD), soluble aggregation assay, or other similar devices/assays may effectively amplify a single tag nucleic acid molecule into a visual signal of higher amplitude. Similarly, a Horseradish Peroxidase enzyme may be localized by an authentic tag onto a LFD location, enabling the enzyme to act enzymatically on substrate-embedded molecule(s) to produce a strong colorimetric reaction, resulting in a visible dot or stripe. In yet other embodiments, the concentration of a signal may be altered to give the appearance of a strong signal from one of a low chemical concentration. In some embodiments, a diffuse signal in solution or on paper may be concentrated, or a concentrated signal may be transported into a diffuse one.

Use of Nanostructures for Molecular Authentication

Nucleic acid nanostructures for use in molecular authentication may be assembled, e.g., pre-formed, nanostructures. Assembled nanostructures functioning as authenticatable tags may comprise structural features, e.g., single-stranded oligonucleotides, hairpin loops or proteins, wherein the structural features of the assembled nanostructures may bind to authenticating identifiers, e.g. complementary nucleic acid sequences or a small molecule, that comprise a detectable moiety, e.g., a fluorescent molecule. Structural features of an assembled nanostructure may encode a authenticatable pattern, wherein the pattern is only decipherable after targeting, e.g., binding, with authenticating identifiers. Imaging of assembled nanostructures, e.g., assembled DNA nanostructures, after targeting with authenticating identifiers may be visualized with Atomic Force Microscopy (AFM), Transmission Electron Microscopy (TEM), or super-resolution imaging techniques such as DNA-PAINT. Structural features of assembled nanostructures may be revealed only in the presence of a solution of authenticating identifiers that use specific hybridization reactions to expose and/or attach the structural features on the nanostructures. Hybridization reactions may also include direct hybridization, toehold exchange reaction, primer exchange reaction, ligation reaction, or hybridization chain reaction.

Nucleic acid nanostructures for use in molecular authentication may be disassembled nanostructures, e.g., at least one scaffold strand or a plurality of single-stranded tiles (SSTs) that may use a plurality of additional strands or tiles in order to assemble a nanostructure. Addition of the a plurality of additional strands or SSTs (i.e., authenticating identifiers) to the disassembled nanostructure allows for assembly of the nanostructure and authentication of the disassembled nanostructure (i.e. tag). In some embodiments, the assembled nanostructure forms only when a solution of authenticating identifiers are added to and incubated with the disassembled nanostructure, e.g., for 10 minutes at room temperature. The solution of authenticating identifiers may be comprised of staple strands or SSTs and may be designed such that one, a few, or any number of strands or SSTs may be used to assemble the nanostructure. Assembly of the nanostructure may allow for formation of a pattern. The assembled nanostructure may be imaged using AFM, TEM, or any other suitable microscope. In some embodiments, the assembled nanostructure be authenticated using non-denaturing gel electrophoresis, e.g., polyacrylamide gel electrophoresis.

Use of Micro-Arrays for Molecular Authentication

Micro-array synthesis allows for geometric patterning of docking strands (oligonucleotides) of specific sequences that are spaced less than a few microns apart from each other, e.g., by ink jet or contact printing. Micro-arrays may be used for molecular authentication. Tags, e.g. docking strands, may be arranged in specific spatial patterns or arrays along a micro-array surface with a pattern only being revealed when complementary authenticating identifiers that specifically bind to the surface-mounted tags are introduced. Patterns or arrays of nucleic acids may also be formed by methods used in the electronics industry for integrated circuit manufacturing, e.g., photolithography. A pattern or array may comprise at least two tags, e.g., docking strands, that are positioned apart from one another at a distance of from about 20 nm to 5 microns, from 20 nm to 1 micron, from 20 nm to 500 nm, 1 micron to 5 microns, or at least about 5 microns. Soft lithography, including micro-contact printing, may utilize a stamp that physically transfers nucleic acid-containing "ink" to a substrate, e.g., paper. Additionally, patterns of oligonucleotides may be formed using ink jet or other printing processes. There may be at least one, at least two, at least three, at least four, at least five, or at least ten unique patterns or arrays. A pattern or array may comprise at least two, at least three, at least four, at least five, or at least ten unique oligonucleotides. There may be at least one, at least three, at least four, at least five, or at least ten unique authenticating identifiers. In some embodiments, the authenticating identifiers comprise a detectable moiety, e.g., a fluorophore, to enable the use of microscopy methods to reveal and authenticate the underlying pattern of the micro-array when the authenticating identifiers are bound to the oligonucleotides of the micro-array. The pattern or array may represent a decipherable image or may be a pattern of intermittently bright, dim, and/or dark spots to be compared against a known master pattern, as shown in FIG. 16B.

Use of Microfluidics for Molecular Authentication

Microfluidic channels may be used to divert a solution of authenticating identifiers along multiple spatially separated directions. This may be used to analyze each of several possible molecular barcodes individually (see e.g. FIG. 16B). Using the geometric arrangement of molecular authentication reactions, multiple verifications may be carried out on the same sample, and the resultant pattern can be validated by fluorescent or color change readouts, e.g., by the naked eye or a device, e.g., a microscope. In some embodiments, microfluidic channels may be constructed of glass or rubber. In some embodiments, channels may be patterned on a paper substrate utilizing wax or other material as a hydrophobic boundary to constrain the movement of a liquid from capillary action.

Use of Macroscale Patterning for Molecular Authentication

Ink jet printing may be used to deposit solutions of tags, e.g., oligonucleotides onto a substrate, e.g., paper, in a specific geometric pattern to provide patterns of sufficient scale and size such that they can be detected with the naked eye. These geometric patterns may be in unique and identifiable shapes, including letters, shapes, images, optical barcode, QR code, etc. Multiple layers of deposited solutions of tags may be printed on top of one another. In some embodiments, the solutions, once dried onto the substrate, e.g., paper, do not reveal a detectable authenticatable pattern until a solution of authenticating identifiers is deposited onto the dried solutions of tags. There may be at least one, at least two, at least three, at least four, at least five, or at least ten layers of deposited solutions of tags. A layer may comprise at least one, at least two, at least three, at least four, at least five, or at least ten unique oligonucleotide(s). A solution of authenticating identifiers may contain at least one, at least three, at least four, at least five, or at least ten unique oligonucleotide(s).

Detectable moieties, e.g., fluorophores, may be attached to the authenticating identifiers such that, when specifically bound to the tags, an underlying pattern be visualized. In some embodiments, binding of authenticating identifiers to the tags causes a color change of a pattern.

In some embodiments, oligonucleotides in solutions deposited on a surface may be considered 'bound' to the surface in that they do not diffuse significantly when an aqueous medium is applied. For example, they may be bound or crosslinked to a bulky molecules such as streptavidin or nanoparticles that don't exhibit significant movement on a surface upon application of an aqueous medium, or bound to strand conjugated/hybridized/cross-linked to bulky molecules. Oligonucleotides may be designed to be of a length such that they become trapped in the pores of the surface upon dehydration. Oligonucleotides may become covalently bound to the surface such as through a crosslinking reaction or become associated to the surface through charged particles.

Multiplexed Patterns

As the composition of patterns described herein can be controlled at any of scale or size, patterning of tags, e.g., oligonucleotides, may also be used to encode exponentially many patterns within an array. An array with a 'n' number of uniquely addressable spots or locations may contain or not contain a specific feature, e.g., an oligonucleotide, such that there are $2^n$ possible configurations of a given grid or pattern within the array. Therefore $2^n$ possible identifiers can be constructed, as shown in FIGS. 16A-16D, e.g., $2^{16}$ identifiers geometrically positioned across different scales. In multiplexed technologies, such as those that may be analyzed or read using DNA-PAINT or multiple strand displacement reactions, if each of 'n' number of spots or positions has 'm' number of possible configurations, there are mu possible configurations or identifiers within a given array. In all scales and sizes, this multiplexed approach allows the same 'm' number of oligonucleotides as can typically be used in any of the 'n' spots or positions, reducing the complexity of the molecular barcode solution (s), because only 'm' possible authenticating identifiers may be used. As a result, only 'm' number of authenticating identifiers may be manufactured, reducing the overall monetary and resource cost of the methods herein across many different patterns. A pattern or array may comprise at least two features, e.g., oligonucleotides, that are positioned apart from one another at a distance from about 20 nm to 5 microns, from 20 nm to 1 micron, from 20 nm to 500 nm, 1 micron to 5 microns, or at least about 5 microns.

A combinatorial use of barcodes may further be used without the use of a patterned substrate. For example, if there are 'n' different barcode sequences that may be either present or absent in a solution, then there are 2' possible combinations of those barcodes. Only 'n' associated detection authentication reactions may be used to check the presence/absence of the barcodes to determine the composition. For example, with just 16 different barcodes that are either present or absent in a mixture of oligonucleotides to be authenticated, there are $2^{16}$ unique combinations. Each of the unique combinations may be associated with a different product, person, step in the supply chain, or other feature. Furthermore, a strategy in which the majority of unique combinations are not deployed may serve as a further barrier to counterfeiting. This would disable a counterfeiter from successfully producing a valid barcode combination even if they knew the barcode sequences used.

In cases of combinatorial barcodes, with or without the use of patterned substrates, barcode combinations may be verified by a person, by a machine that checks against a list of valid barcode combinations, by a phone application that compares the combination against valid barcodes, or by an online computer system. In some embodiments, there is a further encryption of the barcode combinations, similar to strategies used to protect passwords to online services, such that the raw barcode combination information cannot be accessed. For example, barcode combinations may undergo a hash function algorithm that produces a value that can be compared against hash values of all possible valid barcodes. In some embodiments, authentication of combination barcodes is confirmed by further physical authentication measures, such as a one-time password (OTP) or the use of two specific combinations from two sources to be co-authenticated. In some embodiments, the authentication process may further be coupled with a Blockchain recording scheme.

Identification of Subjects and Entities

Compositions, methods and systems described herein are also useful for identifying subjects or entities. Identification of subjects or entities can be applied to a host of applications, including identification of personal or entity-owned items (e.g., clothing worn by a subject, an ingestible product ingested by a subject, a tool utilized by a subject or an entity, a drug utilized by a subject), including example types described elsewhere herein, or documents (e.g., a subject's Will, a check issued by a subject or entity, a document written by a subject or an entity, a sample of bodily fluid or tissue) associated with a particular individual or entity. Other types of articles or products, including those described elsewhere herein can also be associated with a particular subject or entity and can be attributed to its respective subject or entity.

In general, tags can be applied to personal or entity articles/products and authenticating identifiers contacted with the tags to effect identification of the subject or entity, as is described elsewhere herein. Articles or products can be made of materials that are amendable for mixing with a tag. In some embodiments, tags are associated with products marketed by a particular entity and authenticating identifiers are used to identify the identity of the entity that produced the products and/or one or more parties in the supply chain. Examples of subjects include living forms, including humans, animals, plants, and examples of entities include business organizations, non-profits, schools, hospitals, a manufacturer, a distributor, a particular customer, a bank, a law firm, a municipal office, a government office, a government, a corporation, an organization, a group of affiliated units, a currency producer, a passport agency, etc.

Accordingly, an aspect of the present disclosure provides a method of identifying a subject. The method includes: (a) providing an article suspected or expected to be produced by the subject, the article comprising a tag unique to the subject and having at least one nucleic acid molecule, where interaction of the tag with an authenticating identifier exhibiting binding specificity for the tag yields a detectable signal that is indicative of identity of the subject; (b) applying the authenticating identifier to the article; and identifying the subject when the detectable signal is detected.

In another aspect, the present disclosure provides a method of identifying an entity. The method comprises (a) providing an article suspected or expected to be produced by the entity, the article comprising a tag unique to the entity and optionally sharing commonality with a reference tag, the tag having at least one nucleic acid molecule, where interaction of the tag with an authenticating identifier exhibiting binding specificity for the tag yields a detectable signal that is indicative of identity of the entity; (b) applying the authenticating identifier to the article; and (c) identifying the entity when the detectable signal is detected. The reference tag can be an internal control, a positive control and may also itself convey information. For example, the reference tag may specifically interact with a reference authenticating identifier to yield an additional detectable signal indicative of an entity of higher organizational hierarchy to which the entity belongs. For example, the detectable signal may identify Nintendo of America as the manufacturer of a video game system, whereas the additional detectable signal may identify Nintendo Co., Ltd. (of Japan) as the parent company of Nintendo of America.

Authenticable Writing Media and Application Devices

Tag and authenticating identifier compositions, methods and systems described herein can also be implemented in an authenticable writing medium. Accordingly, in an aspect, the present disclosure provides an authenticable writing medium comprising a tag having at least one nucleic acid molecule, wherein application of the authenticable writing medium by a user to an article yields a marking on the article comprising the tag. The tag may be detectable upon interacting with an authenticating identifier exhibiting binding specificity for the tag. For example, the interaction can yield a detectable signal that is indicative of authenticity of the marking made by the user or a party designated by the user. In some embodiments, the tag or the authenticating identifier comprises a nucleic acid molecule having a structure such that the nucleic acid molecule cannot be identified by sequencing.

The authenticable writing medium can take any suitable physical form, including a solid (e.g., a powder), a semi-solid, a vapor or liquid. Moreover, In some embodiments, the authenticable writing medium may take the form of a solution or suspension, in which solid materials are dissolved or suspended, respectively. In some embodiments, the authenticable writing medium is formulated as an ink. Inks can include the tag and other species, including one or more of solvents, pigments, dyes, resins, lubricants, solubilizers, surfactants, particulate matter and fluorescents. The authenticable writing medium can be applied to an object or article in any suitable manner, including, for example s shown in FIG. 15A, via dropping, writing, stamping, squirting, painting, spraying or a combination thereof.

Additionally, the present disclosure also provides devices for applying an authenticable writing medium, such as an ink, to an article. In another aspect, the present disclosure provides a device for generating an authenticable writing medium (e.g., ink) on an article. The device can include a housing that itself may include a first container comprising a first solution comprising an ink, where application of the first solution to the article yields at least one ink layer comprising the ink. The housing can also include a second container comprising a second solution comprising a tag, wherein application of the second solution to the at least one ink layer yields the authenticable ink comprising the tag, wherein interaction between the tag and an authenticating identifier exhibiting binding specificity for the tag yields a detectable signal that is indicative of authenticity of (i) the ink, (ii) a user-generated pattern of the ink layer, or (iii) the article. In some embodiments, the first container may be separate from the second container.

The device may also include a first applicator in fluid communication with the first container. The first applicator may be configured to direct flow of the first solution to the article. Moreover, the device may also include a second applicator in fluid communication with the second container. The second applicator can be configured to direct flow of the second solution to the at least one ink layer. In some embodiments, the first applicator and the second applicator are the same. The first and/or second applicators may be configured with or in fluid communication with one or more pressure devices (e.g., a pump, a vacuum), valves and or fluidic channels that effect flow through the device, including through an applicator. In some embodiments, the first and/or second applicators may be configured as "ink-jet" applicators such that a mist or drops of solution are jettisoned from the applicator to its intended target. In some embodiments, the first and/or second applicator may comprise one or more of a nozzle, a pen, a stamper, an ink-jet, a brush, a sprayer, or a dropper that aids in dispensing solution. Accordingly, the ink can be applied to the article in any suitable manner, including for example as shown in FIG. 15A via dropping, writing, stamping, squirting, painting, spraying or a combination thereof.

In one example, tag-containing inks can be used to identify individuals uniquely, their affiliation with a particular group or organization and/or their particular place in an organizational hierarchy. For example, as shown in FIG. 15B, a particular ink can have tags that are unique to a particular individual. A second ink can have tags (e.g., different tags) that identify members of a particular group or organization. These two inks can be mixed together such that the inks comprise both the individual tag, but also the tag associated with the particular group or organization. Authenticating identifiers can be contacted with the mixed ink and interact with the two tags and produce detectable signals that identify the ink as associated with the individual and also a group or organization to which the individual belongs.

A similar strategy can be employed in identifying members of an organizational hierarchy and their positions in the hierarchy. For example, a third ink comprising a tag that identifies an individual as a "C-level" employee can be added to the individual and organizational inks such that the combined ink comprises identifying tags for all three items. Members of the organization at different levels can have different third tags corresponding to their particular level. Such a scheme can also be used to identify particular employees that report to other employees. Each lower-level employee can have a "manager" tag in their identity ink that identifies them, their organization, and also which manager they report to as shown schematically in FIG. 15B.

Figure 15A:
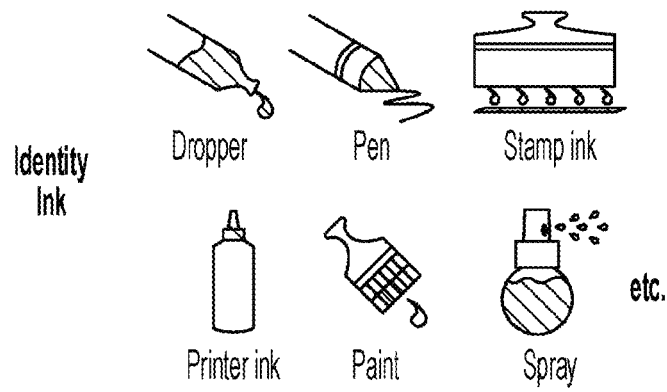
FIGS. 15A-15C illustrate the use of identity ink for authentication.
Figure 15B:
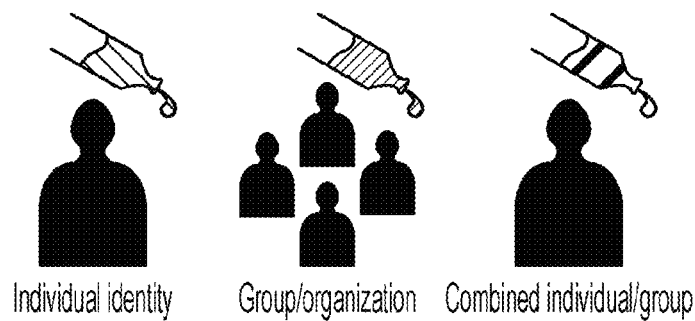
Figure 15C:
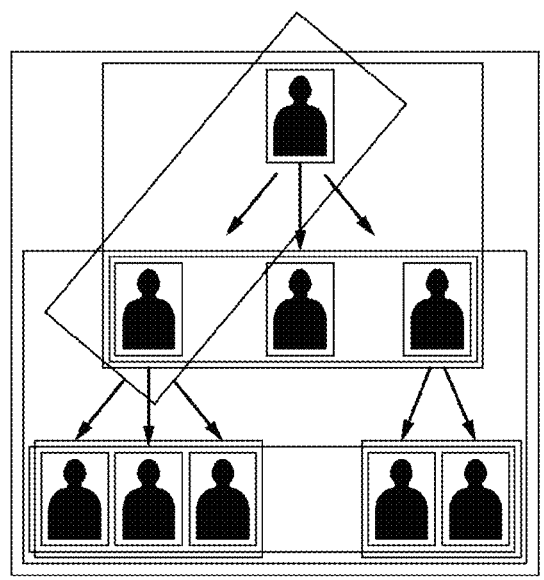

While the examples discussed with respect to FIGS. 15A and 15B are described in the context of ink formulations, such formulations are not meant to be limiting. Any formulation of multiple different tags can be employed. Moreover, methods described here can be used to identify various identifiers associated with a particular individual and hierarchy and organization/group are not meant to be limiting. For example, these methods can be applied analogously to personal identification and entity identification methods described elsewhere herein.

Simplified Customer Use of Testing Kits

The supply chain and similar scenarios enable a DNA-based verification business to supply customers with any number of tests in any scenario with minimal regard to the logistics of ordering and securely receiving and applying tests. In applications when an end customer seeks to verify the authenticity of a product, it may be a burden to separately seek out a new test kit for every tag (e.g., at every new product purchase). In these cases, it may be easier to use the same oligo sequences in the tags and authenticating identifiers to secure multiple products (e.g., on multiple companies' labels) and have a single test kit that the customer can use repeatedly (FIG. 18). This presents a new problem, where a company receives labels purportedly for their own product but instead manufactures imitations of a more lucrative product. Here, a label may contain a logo (e.g., graphic mark, or emblem) specific to a company of interest, manufactured for the company and delivered securely. The purchaser of a Company B telephone may apply the test and find the familial logo, indicating authenticity. As is typical, a negative control, such as the border around the logo, is present to ensure that the label was not copied (e.g., always shows the correct logo with any test application, regardless of DNA). Test 1, identical to Test 2, except for the DNA sequences, would be applied to the label first and if authentic, may reveal the border, for example. Test 2 would then be applied to sequence-specifically reveal the logo. Another company (e.g., Company C) would offer its products with a label that presents a different logo pattern from the same materials.

Kits

Some aspects of the present disclosure provide authentication kits. In some embodiments, a kit comprises a test substrate that comprises, in the following order, (i) a source region comprising detectably-labeled (e.g., enzyme-linked or pigment-linked) strands, (ii) a test region comprising immobilized test strands and an embedded enzyme substrate, and (iii) a control region comprising immobilized control strands that bind to the enzyme-labeled strands and the embedded enzyme substrate, and tags that bind to the enzyme-linked strands and to the immobilized test strands.

In other embodiments, a kit comprises a test substrate that comprises, in the following order, (i) a source region comprising detectably-labeled (e.g., enzyme-linked or pigment-linked) strands, immobilized source strands, and bridge strands, wherein the bridge strands bind both the enzyme-linked strands and the source strands, and (ii) a test region comprising an embedded enzyme substrate, and a barcode composition that comprises tags that bind to the bridge strands. In some embodiments, the kit further comprises a positive control substrate that comprises, in the following order, (i) a source region comprising detectably-labeled (e.g., enzyme-linked or pigment-linked) strands, and (ii) a positive control region comprising an embedded enzyme substrate. In some embodiments, the kit further comprises a negative control substrate that comprises, in the following order, (i) a source region comprising enzyme-linked strands, immobilized source strands, and negative control bridge strands, wherein the negative control bridge strands bind both the enzyme-linked strands and the source strands, and (ii) a negative control region comprising an embedded enzyme substrate, and tags that do not bind to the negative control bridge strands.

Products of Interest

An article or product, as provided herein, is not limited. An article or product may take any physical form, including a solid, a semi-sold, a vapor or a liquid. For example, the article or product may be selected from adhesives, ammunition, apparel, art (e.g., an original piece of art), beauty products, beverages, clothing, coins, consumer products, controlled substances, documents (e.g., legal documents, such as a will or property conveyance, financial documents such as a check), electronics (e.g., computers or computer parts and other electrical components, electronic devices), fibers, fabrics, fragrance/perfume, furniture, ink, jewelry, musical instruments, packaging, paints, a personal article (e.g., an article that may be attributed to a particular person), currency (e.g., paper money, coins), pharmaceuticals, plants (or plant parts or plant derivatives such as oil), plastics, synthetics, textiles, therapeutics, vehicle parts, wine and a writing medium. In some embodiments, a product or article is ingestible by a user or is wearable. Moreover, articles or products, provided herein, may include a research or diagnostic tool, such as, for example, nucleic acid research or diagnostic array.

An article or product may be a "luxury" item having a relatively high monetary value. For example, such a luxury item may have a value (or be priced at) $100 or more, $200 or more, $500 or more, $750 or more, $1000 or more, $2500 or more, $5000 or more, $10000 or more, $50000 or more, $100000 or more, or $1000000 or more.

A product or article used to generate a product may include a transmitter that can provide an indication of authenticity of the article. The indication may be provided in response to the outcome of an interaction between a tag and an authenticating identifier. The transmitter may transmit such indication. In some examples, the transmitter may be a chip, a radiofrequency identifier (RFID) tag or a chemical indicator, such as a medium (e.g., a color strip, a chemi-sensitive layer) that changes color in response to the interaction. In some embodiments, the transmitter may generate a radiative signal that is detectable via infrared, ultraviolet, or any other type of wavelength of the electromagnetic spectrum. The transmitter may utilize luminescence, such as fluorescence, chemiluminescence, bioluminescence, or any other type of optical emission or absorption. In some instances, the transmitter may be a radio transmitter. Moreover, the transmitter may be any type of wireless transmitter. The transmitter may send one or more electrical signal. In some instances, GPS or other location-related signals may be utilized with the transmitter.

In some embodiments, the product or article may include a receiver. The receiver may make use of any of the example modalities and configurations discussed above for transmitters.

FIG. 21 shows an overview of various applications for a molecular authentication system. The molecular authentication system may be provided directly to a product, to a product tag, or as an identity ink. A molecular authentication system may be added (e.g., sprayed or mixed with) a perfume, consumable product (e.g., beverage, food, etc.), or medicine. A sample may be taken from the product and authenticated. A molecular authentication may be added to a product as a label. For example, an authentication label may be added to high end, or luxury, products such as jewelry, vehicles, clothing or electronics. A molecular authentication system may be used in the form of identity ink. The identity ink may be used to verify or authenticate a person or products identity.

Computer Control Systems

Figure 23:
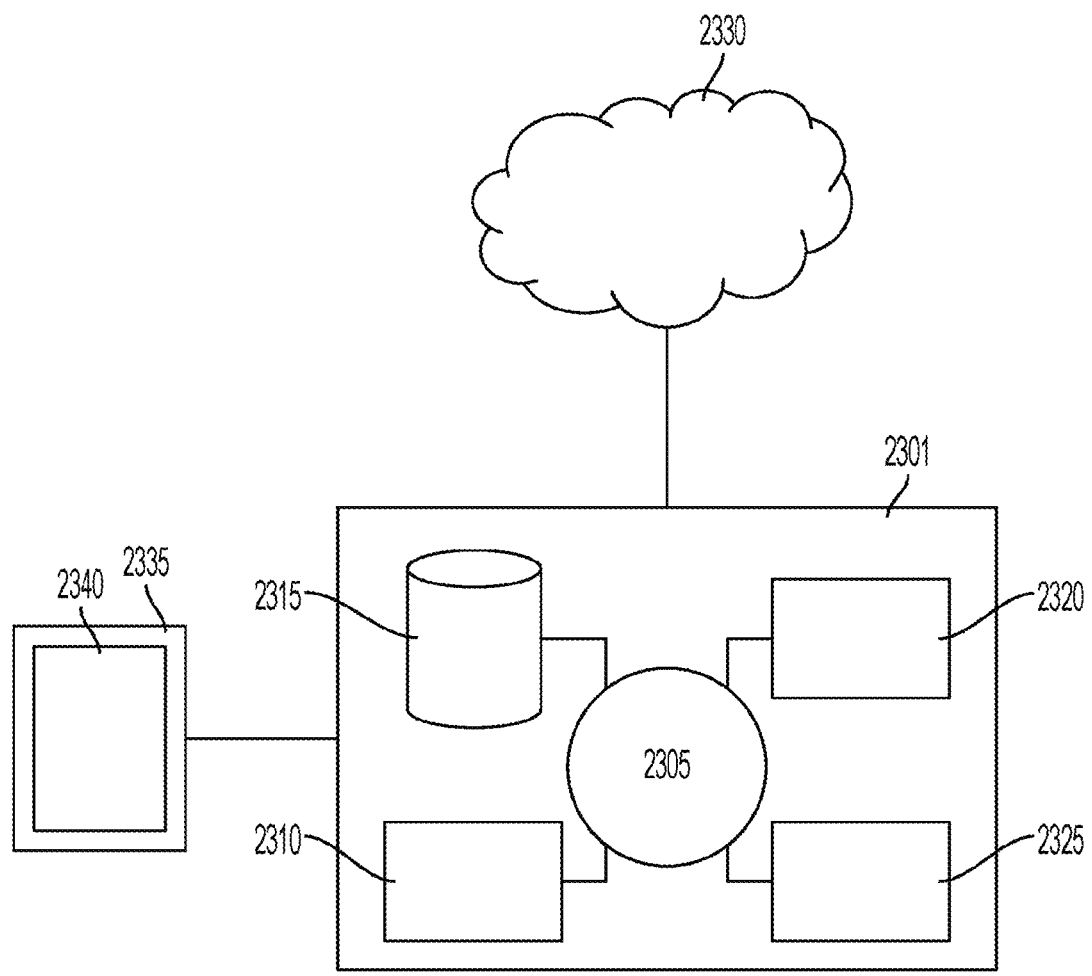
FIG. 23 shows a computer control system that is programmed or otherwise configured to implement methods provided herein.

The present disclosure provides computer control systems that are programmed to implement methods of the present disclosure. FIG. 23 shows a computer system 3301 that is programmed or otherwise configured to detect a signal or otherwise authenticate a product. The computer system 2301 can regulate various aspects of the authentication methods of the present disclosure, such as, for example, authenticating a product or testing product authenticity. The computer system 2301 can be an electronic device of a user or a computer system that is remotely located with respect to the electronic device. The electronic device can be a mobile electronic device and may be in electronic communication with one or more sensors that are operable to authenticate a product.

The computer system 2301 includes a central processing unit (CPU, also "processor" and "computer processor" herein) 2305, which can be a single core or multi core processor, or a plurality of processors for parallel processing. The computer system 2301 also includes memory or memory location 2310 (e.g., random-access memory, read-only memory, flash memory), electronic storage unit 2315 (e.g., hard disk), communication interface 2320 (e.g., network adapter) for communicating with one or more other systems, and peripheral devices 2325, such as cache, other memory, data storage and/or electronic display adapters. The memory 2310, storage unit 2315, interface 2320 and peripheral devices 2325 are in communication with the CPU 2305 through a communication bus (solid lines), such as a motherboard. The storage unit 2315 can be a data storage unit (or data repository) for storing data. The computer system 2301 can be operatively coupled to a computer network ("network") 2330 with the aid of the communication interface 2320. The network 2330 can be the Internet, an internet and/or extranet, or an intranet and/or extranet that is in communication with the Internet. The network 2330 In some embodiments is a telecommunication and/or data network. The network 2330 can include one or more computer servers, which can enable distributed computing, such as cloud computing. The network 2330, In some embodiments with the aid of the computer system 2301, can implement a peer-to-peer network, which may enable devices coupled to the computer system 2301 to behave as a client or a server.

The CPU 2305 can execute a sequence of machine-readable instructions, which can be embodied in a program or software. The instructions may be stored in a memory location, such as the memory 2310. The instructions can be directed to the CPU 2305, which can subsequently program or otherwise configure the CPU 2305 to implement methods of the present disclosure. Examples of operations performed by the CPU 2305 can include fetch, decode, execute, and writeback.

The CPU 2305 can be part of a circuit, such as an integrated circuit. One or more other components of the system 2301 can be included in the circuit. In some embodiments, the circuit is an application specific integrated circuit (ASIC).

The storage unit 2315 can store files, such as drivers, libraries and saved programs. The storage unit 2315 can store user data, e.g., user preferences and user programs. The computer system 2301 can include one or more additional data storage units that are external to the computer system 2301, such as located on a remote server that is in communication with the computer system 2301 through an intranet or the Internet.

The computer system 2301 can communicate with one or more remote computer systems through the network 2330. For instance, the computer system 2301 can communicate with a remote computer system of a user (e.g., a manufacturer, distributer, retailer, or consumer). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2301 via the network 2330.

Methods as described herein can be implemented by way of machine (e.g., computer processor) executable code stored on an electronic storage location of the computer system 2301, such as, for example, on the memory 2310 or electronic storage unit 2315. The machine executable or machine readable code can be provided in the form of software. During use, the code can be executed by the processor 2305. In some embodiments, the code can be retrieved from the storage unit 2315 and stored on the memory 2310 for ready access by the processor 2305. In some situations, the electronic storage unit 2315 can be precluded, and machine-executable instructions are stored on memory 2310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2301, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2301 can include or be in communication with an electronic display 2335 that comprises a user interface (UI) 2340 for providing, for example, a readout indicating the authentication status of a product. Examples of UI's include, without limitation, a graphical user interface (GUI) and web-based user interface. Methods and systems of the present disclosure can be implemented by way of one or more algorithms. An algorithm can be implemented by way of software upon execution by the central processing unit 2305. The algorithm can, for example, provide an authentication tag to a product or identify and/or authenticate a product.

The computer control systems described herein can be designed and used to generate products and implement methods as described herein. For example, an aspect of the present disclosure provides a computer system for generating an authenticating pair comprising a tag and an authenticating identifier usable for authenticating a product from a first party by a second party along a supply chain. The computer system can include one or more databases comprising (i) a first set of data corresponding to a plurality tags, which plurality of tags comprises at least one nucleic acid molecules, and (ii) a second set of data corresponding to a plurality of authenticating identifiers, which plurality of authenticating identifiers comprises the authenticating identifier. The authenticating identifier can exhibit binding specificity for the tag; and one or more computer processors may be operatively coupled to the one or more databases. Moreover, the computer processor may be programmed to (i) generate the authenticating pair comprising the tag and the authenticating identifier, and (ii) store the authenticating pair in memory. The authenticating pair may be usable by the second party along the supply chain to authenticate the product from the first party, such as by using a detectable signal generated upon interaction between the tag and the authenticating identifier. In some embodiments, the computer processor is also programmed to transmit the tag to the first party and/or to transmit the authenticating identifier to the second party. Transmission may be achieved via any suitable medium, including, for example, via an electronic display, over a network, or in hard copy.

In another example, the present disclosure provides a computer system for detecting authentication of a product from a first party by a second party along a supply chain. The computer system may include or more databases comprising (i) a first set of data corresponding to a plurality tags, an individual tag of the plurality is admixed with a product by the first party, which plurality of tags having at least one nucleic acid molecules, and (ii) a second set of data corresponding to a plurality of authenticating identifiers, which plurality of authenticating identifiers comprises the authenticating identifier. The authenticating identifier may exhibit binding specificity for the tag, and interaction between the authenticating identifier and the tag may yield a detectable signal that is indicative of authenticity of the product. The computer system can also include one or more computer processors operatively coupled to the one or more databases, and programmed to receive an electronic signal indicating a presence or absence of the detectable signal. The electronic signal may be transmitted from the product or the second party when the second party triggers the interaction (e.g., contact is made between the tag with the authenticating identifier) between the tag and the authenticating identifier. Such transmission may be completed via a transmission unit of the product that is configured to transmit data concerning the detectable signal.

The one or more computer processors may be programmed or configured to implement one or more additional operations. For example, the one or more computer processors may be programmed to receive the electronic signal concurrent or subsequent to interaction between the tag and the authenticating identifier. Acquisition of signal concurrent to interaction between the tag and the authenticating identifier can be used to monitor the status of authentication in real-time. In another example, the one or more computer processors may be programmed to transmit to a designated party (e.g., the producer of the product, a regulatory agency or personnel, a distributor of the supply chain, or any other authorized party) confirmation of authentication or a lack thereof to a party upon receipt of the electronic signal. In another example, the one or more processors may be configured to receive information from and transmit information to the product, first party and/or said second party. The information can include data relating to the status or the result of authentication of the product. In another example, the one or more processors may be configured to correlate data relating to status of authentication of a given product to geographic information. The geographic information can be, for example, related to one or more of the product, the manufacturer, a distributor, a retailer, a party in the supply chain, a party outside of the supply chain, or any other relevant party.

Additional aspects of the present disclosure are provided in the following numbered paragraphs:

1. A molecular authentication method, comprising:
   distributing to a first entity of a supply chain a tag comprising a first strand that uniquely identifies a product of interest, optionally wherein the first strand has a length of shorter than 50 nucleotides; and
   distributing to at least one additional entity an authenticating identifier composition comprising a second strand that binds to the first strand, wherein binding of the second strand to the first strand produces a detectable signal.
2. The method of paragraph 1, wherein the first entity is a manufacturer of the product of interest, and the second entity is a customer.
3. The method of paragraph 1, wherein the first entity of the supply chain is selected from a supplier, a producer, a distributor, and a retailer, and wherein the second entity of the supply chain is selected from a producer, a distributor, a retailer, and a customer.
4. A molecular authentication method, comprising:
   contacting a product of interest at one step of a supply chain with a tag, wherein the tag comprises a first strand that uniquely identifies the product of interest, optionally wherein the first strand has a length of shorter than 50 nucleotides; and
   combining the first strand of the tag with an authenticating identifier composition that comprises a second strand, wherein the second strand comprises a domain that binds to the first strand, and wherein binding of the second strand to the first strand produces a detectable signal.
5. The method of any one of paragraphs 1-3, wherein:
   the first strand is a component of a set of strands present on the tag, and the set of strands uniquely identifies the product of interest; and
   the second strand is a component of a set of strands present in the authenticating identifier composition, and binding of the set of strands present in the authenticating identifier composition to the set of strands present on the tag produces a detectable signal.
6. The method of paragraph 4, wherein the set of strands present on the tag for a distinct pattern, optionally wherein the distinct pattern is a company logo.
7. The method of any one of paragraphs 1-6, wherein the tag comprises that first strand, which comprises a domain x* and a domain a, and the authenticating identifier composition comprises:

(a) the second strand, which comprises domain a*, domain x, domain b*, and one molecule of a quencher-fluorophore pair, wherein domain a* binds to domain a, and domain x binds to domain x*;
(b) a third strand, which comprises the other molecule of the quencher-fluorophore pair, domain b, and domain x*, wherein domain b binds to domain b*; and
(c) a fourth strand, which comprises domain b and domain x*.
8. The method of paragraph 7, wherein domain x* and domain a of the first strand of the tag are configured in the 5' to 3' direction; domain a*, domain x, domain b*, and one molecule of a quencher-fluorophore pair of the second strand of (a) are configured in the 5' to 3' direction; the other molecule of the quencher-fluorophore pair, domain b, and domain x* of the third strand of (b) are configured in the 5' to 3' direction; and domain b and domain x* of the fourth strand are configured in the 5' to 3' direction.
9. The method of paragraph 7, wherein domain x* and domain a of the first strand of the tag are configured in the 3' to 5' direction; domain a*, domain x, domain b*, and one molecule of a quencher-fluorophore pair of the second strand of (a) are configured in the 3' to 5' direction; the other molecule of the quencher-fluorophore pair, domain b, and domain x* of the third strand of (b) are configured in the 3' to 5' direction; and domain b and domain x* of the fourth strand are configured in the 3' to 5' direction.
10. The method of any one of paragraphs 7-9, wherein the concentration of the fourth strand in the authenticating identifier composition is greater than the combined concentration of the second and third strands, optionally wherein the concentration of the fourth strand in the authenticating identifier composition is at least 2-fold, at least 5-fold, or at least 10-fold greater than the combined concentration of the second and third strands.
11. The method of any one of paragraphs 1-10, wherein the length of the first, second, third, and/or fourth strand is 10-30 nucleotides, 10-25 nucleotides, or 10-20 nucleotides.
12. The method of any one of paragraphs 1-11, wherein first strand is dried or freeze-dried onto a surface of the tag, wherein the first strand is attached to a surface of the tag through a linker, optionally a nanoparticle or biotin-streptavidin binding pair, or wherein the first strand is embedded in a gel matrix or soluble solid coating applied to a surface of the tag, optionally wherein the tag further comprises a protective coating.
13. A molecular authentication method, comprising:
(a) distributing to a first entity of a supply chain, a first catalytic hairpin strand that comprises domain b, a loop domain, domain b* and domain a*; and
(b) distributing to a second entity of the supply chain, a second catalytic hairpin strand that comprises domain c, a loop domain, domain c* and domain b*, wherein the first and second catalytic hairpin strands, in the presence of a primer, a strand displacing polymerase, and dNTPs, are capable of catalyzing the production of a tag strand comprising domain a, domain b, and domain c, wherein domain a binds to domain a*, domain b binds to domain b*, and domain c binds to domain c*; and
(c) distributing to at least one additional entity an authenticating identifier composition, wherein the authenticating identifier composition comprises an authenticating identifier strand comprising domain a*, domain b*, and domain c*, and wherein binding of the authenticating identifier strand to the tag strand produces a detectable signal.

14. A molecular authentication method, comprising:
(a) contacting a product of interest at one step of a supply chain with a first catalytic hairpin strand that comprises domain b, a loop domain, domain b* and domain a*; and
(b) contacting the product of interest at another step of the supply chain with a second catalytic hairpin strand that comprises domain c, a loop domain, domain c* and domain b*, wherein domain b binds to domain b*, and domain c binds to domain c*; and
(c) optionally removing the first and second catalytic hairpin strands from the product of interest;
(d) combining the catalytic hairpin strands of (c) with (i) a primer comprising domain a, wherein domain a binds to domain a*, (ii) a strand displacing polymerase, and (iii) dNTPs, and producing a tag strand comprising domain a, domain b, and domain c; and
(e) authenticating the tag strand using an authenticating identifier composition, wherein the authenticating identifier composition comprises an authenticating identifier strand comprising domain a*, domain b*, and domain c*, and wherein binding of the authenticating identifier strand to the tag strand produces a detectable signal.

15. The method of paragraph 13 or 14, wherein domain b, the loop domain, domain b* and domain a* of the first catalytic hairpin strand of (a) are configured in the 5' to 3' direction; and domain c, the loop domain, domain c* and domain b* of the second catalytic hairpin strand of (b) are configured in the 5' to 3' direction.

16. The method of paragraph 13 or 14, wherein domain b, the loop domain, domain b* and domain a* of the first catalytic hairpin strand of (a) are configured in the 3' to 5' direction; and domain c, the loop domain, domain c* and domain b* of the second catalytic hairpin strand of (b) are configured in the 3' to 5' direction.

17. A molecular authentication method, comprising:
(a) distributing to a first entity of a supply chain, a first tag strand that comprises domain a and domain x; and
(b) distributing to a second entity of the supply chain, a second tag strand that comprises domain b and domain y; and
(c) distributing to at least one additional entity an authenticating identifier composition, wherein the authenticating identifier composition comprises (i) a first authenticating identifier strand comprising, in the 5' to 3' direction, one molecule of a quencher-fluorophore pair, domain y*, domain b*, domain x*, and domain a*, (ii) a second authenticating identifier strand comprising, in the 5' to 3' direction, domain x and domain b, and (iii) a third authenticating identifier strand comprising, in the 5' to 3' direction, domain y and the other molecule of the quencher-fluorophore pair, wherein domain a binds to domain a*, domain x binds to domain x*, domain b binds to domain b*, and domain y binds to domain y*, wherein binding of the first and second tag strands to the first authenticating identifier strand produces a detectable signal.

18. A molecular authentication method, comprising:
(a) applying to a product of interest at one step of a supply chain, a first tag strand that comprises domain a and domain x; and
(b) applying to the product of interest at another step of a supply chain, a second tag strand that comprises domain b and domain y; and
(c) optionally removing the first and second tag strands from the product of interest;
(d) combining the tag strands of (c) with an authenticating identifier composition, wherein the authenticating identifier composition comprises (i) a first authenticating identifier strand comprising, in the 5' to 3' direction, one molecule of a quencher-fluorophore pair, domain y*, domain b*, domain x*, and domain a*, (ii) a second authenticating identifier strand comprising, in the 5' to 3' direction, domain x and domain b, and (iii) a third authenticating identifier strand comprising, in the 5' to 3' direction, domain y and the other molecule of the quencher-fluorophore pair, wherein domain a binds to domain a*, domain x binds to domain x*, domain b binds to domain b*, and domain y binds to domain y*, wherein binding of the first and second tag strands to the first authenticating identifier strand produces a detectable signal.

19. The method of paragraph 17 or 18, wherein domain a and domain x of the first tag strand of (a) are configured in the 5' to 3' direction; and domain b and domain y of the second tag strand of (b) are configured in the 5' to 3' direction.

20. The method of paragraph 17 or 18, wherein domain a and domain x of the first tag strand of (a) are configured in the 3' to 5' direction; and domain b and domain y of the second tag strand of (b) are configured in the 3' to 5' direction.

21. A molecular authentication method, comprising:
(a) distributing to a first entity of a supply chain, a first tag strand that comprises domain a; and
(b) distributing to a second entity of a supply chain, a second tag strand that comprises domain b, wherein domain a is different from domain b; and
(c) distributing to at least one additional entity an authenticating identifier composition, wherein the authenticating identifier composition comprises an authenticating identifier strand comprising a sequence that binds to one end of the first tag strand and binds to one end of the second tag strand, optionally wherein the authenticating identifier composition further comprises ligase.

22. A molecular authentication method, comprising:
(a) applying to a product of interest at a first step of a supply chain, a first tag strand that comprises domain a; and
(b) applying to the product of interest at a second step of the supply chain, a second tag strand that comprises domain b, wherein domain a is different from domain b;
(c) optionally removing the first and second tag strands from the product of interest;
(d) combining the tag strands of (c) with an authenticating identifier composition comprising a first authenticating identifier strand comprising a sequence that binds to one end of the first tag strand and binds to one end of the second tag strand, optionally wherein the authenticating identifier composition further comprises ligase, and producing a ligated tag strand comprising domain a and domain b.

23. A molecular authentication method, comprising:
(a) distributing to a first entity of a first supply chain a tag comprising a set of tag strands formed in a first pattern that uniquely identifies a first product of interest, optionally wherein the tag strands each have a length of shorter than 50 nucleotides;
(b) distributing to a second entity of a second supply chain a tag comprising the set of tag strands formed in a second pattern that uniquely identifies a second product of interest; and
(c) distributing to at least one additional entity of the first supply chain and at least one additional entity of the second supply chain an authenticating identifier composition comprising at least one authenticating identifier strand that binds to the tag strands of (a) and (b), wherein binding of the at least one authenticating identifier strand to the tag strands produces a detectable signal in the shape of the first pattern and a detectable signal in the shape of the second pattern.

24. The method of paragraph 23, wherein the first pattern is a logo of a first company, and the second pattern is a logo of a second company.

25. The method of any one of paragraphs 1-24, wherein the authenticating identifier composition is formulated as a solution.

26. The method of any one of paragraphs 1-25, wherein the product of interest is selected from: adhesives, ammunition, apparel, art, beauty products, beverages, coins, controlled substances, electronics, fibers, fabrics, ink, jewelry, musical instruments, packaging, paints, paper money, pharmaceuticals, plants, plastics, synthetics, textiles, and vehicle parts.

27. A method for producing a product that is authenticable by a user, comprising admixing an article with a tag having at least one nucleic acid molecule, wherein interaction between said tag and an authenticating identifier exhibiting binding specificity for said tag yields a detectable signal that is indicative of authenticity of said product, thereby producing said product that is authenticable by said user.

28. The method of paragraph 27, wherein interaction between said tag and said authenticating identifier aids in yielding a distinct visual pattern that is indicative of authenticity of said product.

29. The method of paragraph 28, wherein said visual pattern is a logo, an optical barcode or a geometric pattern.

30. The method of paragraph 27, wherein said tag or said authenticating identifier comprises a nucleic acid molecule having a structure such that said nucleic acid molecule cannot be identified by sequencing.

31. The method of paragraph 30, wherein said nucleic acid molecule comprises (i) a nucleic acid enantiomer; (ii) a backbone modification, (iii) a covalent modification to a base of said nucleic acid molecule, which covalent modification modulates hybridization of the base to another base; or (iv) at least one unnatural base pair.

32. The method of paragraph 27, further comprising admixing said article with a nucleic acid molecule that does not exhibit binding specificity for said authenticating identifier.

33. The method of paragraph 27, wherein said admixing attaches said tag to said article.

34. The method of paragraph 27, wherein said admixing embeds said tag into said article.

35. The method of paragraph 27, wherein said admixing embeds said tag into a layer attached to said article.

36. The method of paragraph 27, wherein said admixing yields a mixture or solution comprising said tag and said article.

37. The method of paragraph 27, wherein said tag is a hairpin molecule.

38. The method of paragraph 27, wherein said tag is a single-stranded nucleic acid molecule.

39. The method of paragraph 27, wherein said authenticating identifier comprises at least one nucleic acid molecule exhibiting sequence complementary to said tag.

40. The method of paragraph 27, wherein said interaction displaces a nucleic acid molecule hybridized to said authenticating identifier.

41. The method of paragraph 27, wherein said interaction is hybridization.

42. The method of paragraph 27, wherein said signal is an optical signal or an electronic signal.

43. The method of paragraph 27, wherein said product takes a form selected from the group consisting of solid, semi-solid, vapor, or liquid.

44. The method of paragraph 27, wherein said product is ingestible by a user.

45. The method of paragraph 27, wherein said product is wearable

46. The method of paragraph 27, wherein said product is an electronic device.

47. The method of paragraph 27, wherein said product is a consumer product.

48. The product of paragraph 47, wherein said consumer product is selected from the group consisting of perfume, wine, a therapeutic, jewelry, a handbag, an automobile, clothing, a writing medium and furniture.

49. The product of paragraph 27, wherein said product is a document, currency, or an original piece of art.

50. The method of paragraph 27, wherein said product is a luxury product priced at $500 or more.

51. The method of paragraph 27, wherein said product is not a nucleic acid research or diagnostic array.

52. The method of paragraph 27, wherein said tag comprises a plurality of nucleic acid molecules.

53. A product that is authenticable by a user, comprising an article admixed with a tag having at least one nucleic acid molecule, wherein interaction between said tag and an authenticating identifier exhibiting binding specificity for said tag yields a detectable signal that is indicative of authenticity of said product.

54. The product of paragraph 53, wherein interaction between said tag and said authenticating identifier aids in yielding a distinct visual pattern that is indicative of authenticity of said product.

55. The product of paragraph 54, wherein said visual pattern is a logo, an optical barcode or a geometric pattern.

56. The product of paragraph 53, wherein said tag or said authenticating identifier comprises a nucleic acid molecule having a structure such that said nucleic acid molecule cannot be identified by sequencing.

57. The product of paragraph 56, wherein said nucleic acid molecule comprises (i) a nucleic acid enantiomer; (ii) a backbone modification, (iii) a covalent modification to a base of said nucleic acid molecule, which covalent modification modulates hybridization of the base to another base; or (iv) at least one unnatural base pair.

58. The product of paragraph 53, wherein said tag is a single-stranded nucleic acid molecule.

59. The product of paragraph 53, wherein said tag is attached to said article.

60. The product of paragraph 53, wherein said tag is embedded into said article.
61. The product of paragraph 53, wherein said tag is embedded in a layer attached to said article.
62. The product of paragraph 53, wherein said product comprises a mixture or solution of said tag and said article.
63. The product of paragraph 53, wherein said tag is a hairpin molecule.
64. The product of paragraph 53, wherein said authenticating identifier comprises a nucleic acid molecule exhibiting sequence complementarity to said tag.
65. The product of paragraph 53, wherein said interaction displaces a nucleic acid molecule hybridized to said authenticating identifier.
66. The product of paragraph 53, wherein said interaction is hybridization.
67. The product of paragraph 53, wherein said product is ingestible by a user.
68. The product of paragraph 53, wherein said product is wearable.
69. The product of paragraph 53, wherein said product is an electronic device.
70. The product of paragraph 53, wherein said product is a consumer product.
71. The product of paragraph 70, wherein said consumer product is selected from the group consisting of perfume, wine, a therapeutic, jewelry, a handbag, an automobile, clothing, a writing medium and furniture.
72. The product of paragraph 53, wherein said product is a document, currency, or an original piece of art.
73. The product of paragraph 53, wherein said product is not a nucleic acid research or diagnostic array.
74. The product of paragraph 53, wherein said tag comprises a plurality of nucleic acid molecules.
75. The product of paragraph 53, wherein said product further comprises one or more additional tags admixed with said article and said tag, wherein said authenticating identifier does not exhibiting binding specificity for said one or more additional tags.
76. The product of paragraph 75, wherein said product further comprises a transmission unit configured to transmit an electronic signal indicative of the presence or absence of the detectable signal to a designated party.
77. The product of paragraph 76, wherein said designated party is (i) the producer of said product, (ii) a regulatory agency or personnel, (iii) a distributor in a supply chain, (iv) a party authorized to receive confirmation of authenticity or a lack thereof.
78. A method for testing authenticity of a product by a user, comprising: (i) applying a solution comprising an authenticating identifier to said product containing or suspected of containing a tag, wherein said authenticating identifier exhibits binding specificity for said tag such that interaction between said authenticating identifier and said tag yields a detectable signal that is indicative of authenticity of said product, and (ii) identifying a presence or absence of said detectable signal, thereby testing said authenticity of said product.
79. The method of paragraph 78, wherein interaction between said tag and said authenticating identifier aids in yielding a distinct visual pattern that is indicative of authenticity of said product.
80. The method of paragraph 79, wherein said visual pattern is a logo, an optical barcode or a geometric pattern.
81. The method of paragraph 78, wherein said tag or said authenticating identifier comprises a nucleic acid molecule having a structure such that said nucleic acid molecule cannot be identified by sequencing.
82. The method of paragraph 81, wherein said nucleic acid molecule comprises (i) a nucleic acid enantiomer; (ii) a backbone modification, (iii) a covalent modification to a base of said nucleic acid molecule, which covalent modification modulates hybridization of the base to another base; or (iv) at least one unnatural base pair.
83. The method of paragraph 78, further comprising alerting or notifying a party in a supply chain of said product as to said authenticity of said product.
84. The method of paragraph 78, further comprising requesting a remedial measure from a party in a supply chain of said article.
85. The method of paragraph 84, wherein said remedial measure is a refund or a replacement.
86. The method of paragraph 78, wherein said detectable signal is part of a pattern of optical signals.
87. The method of paragraph 78, wherein said presence of said detectable signal indicates that said product is authentic.
88. The method of paragraph 78, wherein said product is ingestible by a user.
89. The method of paragraph 78, wherein said product is wearable.
90. The method of paragraph 78, wherein said product is an electronic device.
91. The method of paragraph 78, wherein said product is a consumer product.
92. The method of paragraph 91, wherein said consumer product is selected from the group consisting of perfume, wine, a therapeutic, jewelry, a handbag, an automobile, clothing, a writing medium and furniture.
93. The method of paragraph 78, wherein said product is a document, currency, or an original piece of art.
94. The method of paragraph 78, wherein said product is not a nucleic acid research or diagnostic array.
95. The method of paragraph 78, wherein said tag comprises a plurality of nucleic acid molecules.
96. The method of paragraph 78, wherein said product comprises one or more additional tags, wherein said authenticating identifier does not exhibit binding specificity for said one or more additional tags.
97. A method for product authentication, comprising:
   (a) generating an authenticating pair comprising a tag and an authenticating identifier usable for authenticating a product from a first party by a second party, wherein said tag comprises at least one nucleic acid molecule and said authenticating identifier exhibits binding specificity for said tag, and wherein said product comprises said tag;
   (b) providing said tag or information concerning said tag to said first party to effect said first party to produce said product comprising said tag; and
   (c) providing said authenticating identifier or information concerning said authenticating identifier to a second party, wherein interaction between said tag and said authenticating identifier exhibiting binding specificity for said tag yields a detectable signal that is indicative of authenticity of said product.
98. The method of paragraph 97, wherein interaction between said tag and said authenticating identifier aids in yielding a distinct visual pattern that is indicative of authenticity of said product.

99. The method of paragraph 98, wherein said visual pattern is a logo, an optical barcode or a geometric pattern.
100. The method of paragraph 98, wherein said tag or said authenticating identifier comprises a nucleic acid molecule having a structure such that said nucleic acid molecule cannot be identified by sequencing.
101. The method of paragraph 100, wherein said nucleic acid molecule comprises (i) a nucleic acid enantiomer; (ii) a backbone modification, (iii) a covalent modification to a base of said nucleic acid molecule, which covalent modification modulates hybridization of the base to another base; or (iv) at least one unnatural base pair.
102. The method of paragraph 97, said product comprises one or more additional tags that do not exhibit binding specificity for said authenticating identifier.
103. The method of paragraph 97, wherein said first party and said second party are members of a supply chain.
104. The method of paragraph 97, wherein said generating an authenticating pair comprises selecting a tag from a plurality of tags and selecting an authenticating identifier from a plurality of authenticating identifiers, wherein said authenticating identifier exhibits binding specificity for said tag.
105. The method of paragraph 104, wherein said authenticating identifier does not exhibit binding specificity for other tags from said plurality of tags.
106. The method of paragraph 97, wherein said tag is provided to said first party in solution form.
107. The method of paragraph 97, wherein information of said tag and/or information of said authenticating identifier is provided to said first party in electronic format.
108. The method of paragraph 97, wherein said authenticating identifier is provided to said second party in solution form.
109. A computer system for generating an authenticating pair comprising a tag and an authenticating identifier usable for authenticating a product from a first party by a second party along a supply chain, comprising:
  one or more databases comprising (i) a first set of data corresponding to a plurality tags, which plurality of tags comprises at least one nucleic acid molecules, and (ii) a second set of data corresponding to a plurality of authenticating identifiers, which plurality of authenticating identifiers comprises said authenticating identifier, wherein said authenticating identifier exhibits binding specificity for said tag; and
  one or more computer processors operatively coupled to said one or more databases, wherein said computer processor is programmed to (i) generate said authenticating pair comprising said tag and said authenticating identifier, and (ii) store said authenticating pair in memory, wherein said authenticating pair is usable by said second party along said supply chain to authenticate said product from said first party, using a detectable signal generated upon interaction between said tag and said authenticating identifier.
110. The computer system of paragraph 109, wherein said computer processor is programmed to transmit said tag to said first party.
111. The computer system of paragraph 109, wherein said computer processor is programmed to transmit said authenticating identifier to said second party.
112. A computer system for detecting authentication of a product from a first party by a second party along a supply chain, comprising:
  one or more databases comprising (i) a first set of data corresponding to a plurality tags, an individual tag of said plurality is admixed with a product by said first party, which plurality of tags having at least one nucleic acid molecules, and (ii) a second set of data corresponding to a plurality of authenticating identifiers, which plurality of authenticating identifiers comprises said authenticating identifier, wherein said authenticating identifier exhibits binding specificity for said tag, and wherein interaction between said authenticating identifier and said tag yields a detectable signal that is indicative of authenticity of said product; and
  one or more computer processors operatively coupled to said one or more databases, and programmed to receive an electronic signal indicating a presence or absence of said detectable signal.
113. The computer system of paragraph 112, wherein said one or more computer processors are programmed to receive said electronic signal concurrent or subsequent to said interaction between said tag and said authenticating identifier.
114. The computer system of paragraph 112, wherein said electronic signal is transmitted from said product or said second party when said second party triggers said interaction between said tag and said authenticating identifier.
115. The computer system of paragraph 112, wherein said one or more computer processors are programmed to transmit to a designated party a confirmation of authentication or a lack thereof to a party upon receipt of said electronic signal.
116. The computer system of paragraph 112, wherein said designated party is (i) the producer of the product; (ii) a regulatory agency or personnel; (iii) a distributor of said supply chain; or (iv) a party authorized to receive such confirmation or said lack thereof.
117. The computer system of paragraph 112, wherein said computer system is configured to monitor status of authentication in real-time.
118. The computer system of paragraph 112, wherein said product comprises a transmission unit configured to transmit data concerning said detectable signal.
119. The computer system of paragraph 112, wherein said one or more processors are configured to receive information from and transmit information to said product, first party, and/or said second party, wherein said information comprises data relating to status of authentication of said product.
120. The computer system of paragraph 112, wherein said one or more processors are configured to correlate data relating to status of authentication of a given product to geographic information of: (i) said product, and/or (ii) a party in or outside of said supply chain possessing said product.
121. A molecular complex comprising a first nucleic acid molecule coupled to a second nucleic acid molecule through a third nucleic acid molecule having sequence complementarity with said first nucleic acid molecule and said second nucleic acid molecule, which second nucleic acid molecule is conjugated to an enzyme.
122. The molecular complex of paragraph 121, wherein said enzyme catalyzes a reaction yielding a detectable signal.

123. The molecular complex of paragraph 121, wherein said enzyme catalyzes a reaction yielding a signal that is detectable by a naked eye without aid of a detector.

124. The molecular complex of paragraph 121, wherein said first nucleic acid molecule is coupled to an article.

125. The molecular complex of paragraph 124, wherein said first nucleic acid molecule is coupled to said article at a first region, and wherein said article comprises a second region comprising said third nucleic acid molecule having sequencing complementarity with said second nucleic acid molecule, wherein interaction between said second nucleic acid molecule and said third nucleic acid molecule yields a detectable signal.

126. A product comprising an article admixed with a molecular complex, which molecule complex comprises a first nucleic acid molecule coupled to a second nucleic acid molecule through a third nucleic acid molecule having sequence complementarity with said first nucleic acid molecule and said second nucleic acid molecule, wherein said second nucleic acid molecule is conjugated to an enzyme.

127. The product of paragraph 126, wherein said first nucleic acid molecule is coupled to said article.

128. The product of paragraph 125, wherein said first nucleic acid molecule is coupled to said article at a first region, and wherein said article comprises a second region comprising said third nucleic acid molecule having sequencing complementarity with said second nucleic acid molecule, wherein interaction between said second nucleic acid molecule and said third nucleic acid molecule yields a detectable signal.

129. The product of paragraph 126, wherein said product is wearable.

130. The product of paragraph 126, wherein said product is an electronic device.

131. The product of paragraph 126, wherein said product is a consumer product.

132. The product of paragraph 131, wherein said consumer product is selected from the group consisting of perfume, wine, a therapeutic, jewelry, a handbag, an automobile, clothing, a writing medium and furniture.

133. The product of paragraph 126, wherein said product is a document, currency or an original piece of art.

134. The product of paragraph 126, wherein said product is not a nucleic acid research or diagnostic array.

135. An authenticable writing medium, comprising a tag having at least one nucleic acid molecule, wherein application of said authenticable writing medium by a user to an article yields a marking on said article comprising said tag, wherein said tag is detectable upon interacting with an authenticating identifier exhibiting binding specificity for said tag, wherein said interaction yields a detectable signal that is indicative of authenticity of said marking made by said user or a party designated by said user, and wherein said tag or said authenticating identifier comprises a nucleic acid molecule having a structure such that said nucleic acid molecule cannot be identified by sequencing.

136. The authenticable writing medium of paragraph 135, wherein said authenticable writing medium takes a form selected from the group consisting of a solid, a semi-solid, a vapor, or a liquid.

137. The authenticable writing medium of paragraph 135, wherein said authenticable writing medium is formulated as an ink.

138. The authenticable writing medium of paragraph 135, wherein said writing medium is formulated in the form of a powder.

139. A method of identifying a subject comprising:
(a) providing an article suspected or expected to be produced by said subject, said article comprising a tag unique to said subject and having at least one nucleic acid molecule, wherein interaction of said tag with an authenticating identifier exhibiting binding specificity for said tag yields a detectable signal that is indicative of identity of said subject;
(b) applying said authenticating identifier to said article; and
(c) identifying said subject when said detectable signal is detected.

140. The method of paragraph 139, wherein said article is made of a material amenable for admixing said tag.

141. The method of paragraph 139, wherein said article is a personal article selected from the group consisting of a document written by said subject, clothing worn by said subject, an ingestible product ingested by said subject, a tool utilized by said subject and a drug utilized by said subject.

142. The method of paragraph 139, wherein said article is said subject's Will.

143. The method of paragraph 139, wherein said article is a check issued by said subject.

144. The method of paragraph 139, wherein said subject is an animal.

145. The method of paragraph 139, wherein said subject is human.

146. A method of identifying an entity, comprising:
(a) providing an article suspected or expected to be produced by said entity, said article comprising a tag unique to said entity and optionally sharing commonality with a reference tag, said tag having at least one nucleic acid molecule, wherein interaction of said tag with an authenticating identifier exhibiting binding specificity for said tag yields a detectable signal that is indicative of identity of said entity;
(b) applying said authenticating identifier to said article; and
(c) identifying said entity when said detectable signal is detected.

147. The method of paragraph 146, wherein said entity is a corporation, organization, or a group of affiliated units.

148. The method of paragraph 146, wherein said article is made of a material amendable for admixing said tag.

149. The method of paragraph 146, wherein said article is a product marketed by said entity.

150. The method of paragraph 146, wherein said reference tag interacts specifically with a reference authenticating identifier to yield an additional detectable signal indicative of an entity of higher organizational hierarchy to which said entity belongs.

151. A device for generating an authenticable ink on an article, comprising:
a housing comprising:
a first container comprising a first solution comprising an ink, wherein application of said first solution to said article yields at least one ink layer comprising said ink; and
a second container comprising a second solution comprising a tag, wherein application of said second solution to said at least one layer yields said authenticable ink comprising said tag, wherein interaction between said tag and an authenticating identifier exhibiting binding specificity for said tag yields a detectable signal that is indicative of authenticity of (i) said ink, (ii) a user-generated pattern of said ink layer, or (iii) said article.

152. The device of paragraph 151, wherein said first container is separate from said second container.

153. The device of paragraph 151, further comprising a first applicator in fluid communication with said first container, wherein said first applicator is configured to direct flow of said first solution to said article.

154. The device of paragraph 153, further comprising a second applicator in fluid communication with said second container, wherein said second applicator is configured to direct flow of said second solution to said at least one ink layer.

155. The device of paragraph 154, wherein said first applicator and said second applicator are the same.

156. A molecular authentication method, comprising:
(a) distributing to a first entity of a supply chain a tag comprising a nucleic acid nanostructure that uniquely identifies a product of interest, wherein the nanostructure is linked to a docking strand; and
(b) distributing to an additional entity an authenticating identifier composition comprising a signal generating imager strand that binds to the docking strand, wherein binding of the imager strand to the docking strand produces a detectable signal.

157. A molecular authentication method, comprising:
(a) providing a product of interest at one step of a supply chain, wherein the product of interest comprises a tag that comprises a nucleic acid nanostructure that uniquely identifies the product of interest, wherein the nucleic acid nanostructure is linked to a docking strand; and
(b) combining the tag with an authenticating identifier composition that comprises a signal generating imager strand that binds to the docking strand, wherein binding of the imager strand to the docking strand produces a detectable signal.

158. A method of identifying a subject, comprising:
(a) providing a product suspected or expected to be produced by a subject, wherein the article comprises a tag comprising a nucleic acid nanostructure unique to said subject, wherein the nucleic acid nanostructure comprises a docking strand, and wherein interaction of the tag with an authenticating identifier composition comprising a signal generating imager strand exhibiting binding specificity for the docking strand yields a detectable signal that is indicative of identity of the subject;
(b) applying the authenticating identifier composition to the article; and
(c) identifying the subject when the detectable signal is detected.

159. A molecular authentication method, comprising:
(a) distributing to a first entity of a supply chain a tag comprising a scaffold strand or a plurality of single-stranded tiles (SSTs) that uniquely identifies a product of interest and requires a plurality of additional strands or SSTs to assemble into a nanostructure; and
(b) distributing to an additional entity an authenticating identifier composition comprising a plurality of staple strands or a plurality of additional SSTs that bind to the scaffold strand or the plurality of SSTs to assemble the nanostructure, optionally wherein the additional staple strands or SSTs comprise a detectable moiety.

160. A molecular authentication method, comprising:
(a) providing a product of interest at one step of a supply chain, wherein the product of interest comprises a tag that comprises a scaffold strand or a plurality of single-stranded tiles (SSTs) that uniquely identifies a product of interest and requires a plurality of additional strands or SSTs to assemble into a nanostructure; and
(b) combining the tag with an authenticating identifier composition comprising a plurality of staple strands or a plurality of additional SSTs that bind to the scaffold strand or the plurality of SSTs to assemble the nanostructure, optionally wherein the additional staple strands or SSTs comprise a detectable moiety.

161. A method of identifying a subject, comprising:
(a) providing a product suspected or expected to be produced by a subject, wherein the article comprises a tag comprising a scaffold strand or a plurality of single-stranded tiles (SSTs) that uniquely identifies a product of interest and requires a plurality of additional strands or SSTs to assemble into a nanostructure, and wherein interaction of the tag with an authenticating identifier composition comprising a plurality of staple strands or a plurality of additional SSTs that bind to the scaffold strand or the plurality of SSTs to assemble the nanostructure yields a nucleic acid nanostructure that is indicative of identity of the subject;
(b) applying the authenticating identifier composition to the article; and
(c) identifying the subject when the nucleic acid nanostructure is assembled.

162. A molecular authentication method, comprising:
(a) distributing to a first entity of a supply chain a tag comprising a nucleic acid array that uniquely identifies a product of interest, wherein the array comprises a plurality of docking strands positioned into a first pattern or shape; and
(b) distributing to an additional entity an authenticating identifier composition comprising imager strands that bind to the docking strands, optionally wherein the imager strands comprise a detectable moiety, wherein binding of the imager strands to the docking strands generates a second pattern or shape.

163. A molecular authentication method, comprising:
(a) providing a product of interest at one step of a supply chain, wherein the product of interest comprises a tag that comprises a nucleic acid array that uniquely identifies a product of interest, wherein the array comprises a plurality of docking strands positioned into a first pattern or shape; and
(b) combining the tag with an authenticating identifier composition comprising imager strands that bind to the docking strands, optionally wherein the imager strands comprise a detectable moiety, wherein binding of the imager strands to the docking strands generates a second pattern or shape.

164. A method of identifying a subject, comprising:
(a) providing a product suspected or expected to be produced by a subject, wherein the article comprises a tag comprising a nucleic acid array that uniquely identifies a product of interest, wherein the array comprises a plurality of docking strands positioned into a first pattern or shape, and wherein interaction of the tag with an authenticating identifier composition comprising imager strands that bind to the docking strands, optionally wherein the imager strands comprise a detectable moiety, wherein binding of the imager strands to the docking strands yields a second pattern or shape that is indicative of identity of the subject;
(b) applying the authenticating identifier composition to the article; and
(c) identifying the subject when the nucleic acid nanostructure is assembled.

165. The method of any one of paragraphs 156-164, wherein the nucleic acid nanostructure is a DNA origami structure or a DNA brick structure.

166. The method of any one of paragraphs 156-165, wherein the imager strand binds to the docking strand through direct hybridization, toehold exchange reaction, primer exchange reaction, ligation reaction, or hybridization chain reaction.

167. The method of any one of paragraphs 156-166, wherein the imager strand is linked to a fluorophore.

168. The method of any one of paragraphs 156-167, wherein the detectable signal is detected using optical detectors, electronic detectors, atomic force microscopy, transmission electron microscopy, or super-resolution imaging techniques (e.g. DNA-PAINT).

169. The method of any one of paragraphs 162-168, wherein the array comprises $2^n$ strands, wherein n is the number of uniquely addressable locations within a pattern or shape.

170. The method of any one of paragraphs 162-169, wherein the array comprises $m^n$ strands, wherein m is the number of possible configurations of the at least one array and n is the number of uniquely addressable locations within a pattern or shape.

171. The method of any one of paragraphs 162-170, the pattern or shape can be detected with the naked eye.

172. The method of any one of paragraphs 162-171, wherein the array comprises a plurality of strands that have been ink jet or contact printed onto a surface.

173. The method of any one of paragraphs 162-172, wherein the array comprises a plurality of strands that are positioned apart from one another at a distance of 20 nanometers up to 5 microns.

174. The method of paragraph 1 or 4, wherein a tag or signal may be may be amplified prior to, during, or after binding of the second strand with the first strand.

175. The method of any one of paragraphs 13, 14, 17, 18, 21, 22, 27, 53, 78, 97, 139, 146, or 155 to 164, wherein a tag or signal is amplified prior to, during, or after binding or interaction of the authenticating identifier strand with the tag strand(s).

176. The method of paragraph 172 or 173, wherein the tag or signal is amplified using at least one enzymatic method.

177. The method of paragraph 176, wherein the at least one enzymatic method is a Polymerase Chain Reaction (PCR), Loop-Mediated Isothermal Amplification (LAMP), Rolling Circle Amplification (RCA), Recombinase Polymerase Amplification (RPA), nick and extend-type scheme, and/or signal amplification by exchange reaction (SABER).

178. The method of paragraph 172 or 173, wherein the tag or signal is amplified using at least one non-enzymatic method.

179. The method of paragraph 178, wherein the at least one non-enzymatic method involves the use of dynamic nucleic acid circuits that can rapidly change state in the presence of a nucleic acid trigger.

180. The method of paragraph 178, wherein the non-enzymatic method comprises a step of direct conversion of a non-nucleic acid signal in the presence of nanoparticle or enzyme.

181. The method of paragraph 180, wherein the nanoparticle is a gold nanoparticle.

182. The method of paragraph 174 or 175, wherein the tag or signal is amplified at a constant temperature.

183. A molecular authentication method, comprising:
(a) providing a test substrate that comprises, in the following order, (i) a source region comprising enzyme-linked strands, (ii) a test region comprising immobilized test strands and an embedded enzyme substrate, and (iii) a control region comprising immobilized control strands that bind to the enzyme-linked strands and an embedded enzyme substrate;
(b) applying to the test substrate a sample that optionally comprises tags that bind to the enzyme-linked strands and to the immobilized test strands; and
(c) detecting a colorimetric signal in the test region and/or detecting a colorimetric signal in the control region.

184. The method of paragraph 183, wherein the colorimetric signal in the test region is produced by binding of the tags to the immobilized test strands.

185. The method of paragraph 183 or 184, wherein the colorimetric signal in the control region is produced by binding of the enzyme-linked strands to the immobilized control stands.

186. The method of paragraph 183, wherein the sample comprises the tags.

187. The method of any one of paragraphs 183-186, wherein the enzyme-linked strands, immobilized test strands, and immobilized control strands comprise single-stranded DNA.

188. The method of any one of paragraphs 183-186, wherein the enzyme-linked strands, immobilized test strands, and immobilized control strands comprise single-stranded RNA.

189. The method of any one of paragraphs 183-188, wherein the tags are 10-30 nucleotides in length.

190. A method molecular authentication method, comprising:
(a) providing a test substrate that comprises, in the following order, (i) a source region comprising enzyme-linked strands, immobilized source strands, and bridge strands, wherein the bridge strands bind both the enzyme-linked strands and the source strands, and (ii) a test region comprising an embedded enzyme substrate;
(b) applying to the test substrate a sample that optionally comprises tags that bind to the bridge strands; and
(c) detecting a colorimetric signal in the test region or detecting a colorimetric signal in the source region.

191. The method of paragraph 190, further comprising:
(a) providing a positive control substrate that comprises, in the following order, (i) a source region comprising enzyme-linked strands, and (ii) a positive control region comprising an embedded enzyme substrate;
(b) applying the sample to the positive control substrate; and
(c) detecting a colorimetric signal in the positive control region.

192. The method of paragraph 190 or 191, further comprising:
(a) providing a negative control substrate that comprises, in the following order, (i) a source region comprising enzyme-linked strands, immobilized source strands, and negative control bridge strands, wherein the negative control bridge strands bind both the enzyme-linked strands and the immobilized source strands but do not bind the tags, and (ii) a negative control region comprising an embedded enzyme substrate;
(b) applying the sample to the negative control substrate; and
(c) detecting a colorimetric signal in the source region.

193. A method molecular authentication method, comprising:
(a) providing a test substrate that comprises, in the following order, (i) a source region comprising pigment-linked strands, immobilized source strands, and bridge strands, wherein the bridge strands bind both the pigment-linked strands and the source strands, and (ii) a test region;
(b) applying to the test substrate a sample that optionally comprises tags that bind to the bridge strands; and
(c) detecting pigment in the source region or the test region.

194. The method of paragraph 190, further comprising:
(a) providing a positive control substrate that comprises, in the following order, (i) a source region comprising pigment-linked strands, and (ii) a positive control region;
(b) applying the sample to the positive control substrate; and
(c) detecting a colorimetric signal in the positive control region.

195. The method of paragraph 190 or 191, further comprising:
(a) providing a negative control substrate that comprises, in the following order, (i) a source region comprising pigment-linked strands, immobilized source strands, and negative control bridge strands, wherein the negative control bridge strands bind both the pigment-linked strands and the immobilized source strands but do not bind the tags, and (ii) a negative control region;
(b) applying the sample to the negative control substrate; and
(c) detecting a colorimetric signal in the source region.

196. A test substrate comprising, in the following order, (i) a source region comprising enzyme-linked strands, (ii) a test region comprising immobilized test strands and an embedded enzyme substrate, and (iii) a control region comprising immobilized control strands that bind to the enzyme-linked strands and an embedded enzyme substrate.

197. A test substrate comprising, in the following order, (i) a source region comprising enzyme-linked strands, immobilized source strands, and bridge strands, wherein the bridge strands bind both the enzyme-linked strands and the source strands, and (ii) a test region comprising an embedded enzyme substrate.

198. A test substrate comprising, in the following order, (i) a source region comprising pigment-linked strands, immobilized source strands, and bridge strands, wherein the bridge strands bind both the pigment-linked strands and the immobilized source strands, and (ii) a test region.

199. A kit comprising:
a test substrate that comprises, in the following order, (i) a source region comprising enzyme-linked strands, (ii) a test region comprising immobilized test strands and an embedded enzyme substrate, and (iii) a control region comprising immobilized control strands that bind to the enzyme-labeled strands and the embedded enzyme substrate; and
tags that bind to the enzyme-linked strands and to the immobilized test strands.

200. A kit comprising:
a test substrate that comprises, in the following order, (i) a source region comprising enzyme-linked strands, immobilized source strands, and bridge strands, wherein the bridge strands bind both the enzyme-linked strands and the source strands, and (ii) a test region comprising an embedded enzyme substrate; and
a barcode composition that comprises tags that bind to the bridge strands.

201. The kit of paragraph 200, further comprising:
a positive control substrate that comprises, in the following order, (i) a source region comprising enzyme-linked strands, and (ii) a positive control region comprising an embedded enzyme substrate.

202. The kit of paragraph 200 or 201, further comprising:
a negative control substrate that comprises, in the following order, (i) a source region comprising enzyme-linked strands, immobilized source strands, and negative control bridge strands, wherein the negative control bridge strands bind both the enzyme-linked strands and the source strands, and (ii) a negative control region comprising an embedded enzyme substrate; and
tags that do not bind to the negative control bridge strands.

203. A kit comprising:
a test substrate that comprises, in the following order, (i) a source region comprising pigment-linked strands, immobilized source strands, and bridge strands, wherein the bride strands bind both the pigment-linked strands and the source strands, and (ii) a test region; and
tags that bind to the bridge strands.

204. The kit of paragraph 203, further comprising:
a positive control substrate that comprises, in the following order, (i) a source region comprising unbound pigment-linked strands, and (ii) a positive control region.

205. The kit of paragraph 203 or 204, further comprising:
a negative control substrate that comprises, in the following order, (i) a source region comprising pigment-linked strands, immobilized source strands, and negative control bridge strands, wherein the negative control bridge strands bind both the pigment-linked strands and the source strands, and (ii) a negative control region; and
tags that do not bind to the negative control bridge strands.

206. The method, test substrate, or kit of any one of the preceding paragraphs, wherein the tag has a length of shorter than 50 nucleotides.

207. The method, test substrate, or kit of any one of the preceding paragraphs, wherein the enzyme is horseradish peroxidase (HRP).
208. The method, test substrate, or kit of any one of the preceding paragraphs, wherein the embedded substrate is 3,3',5,5'-tetramethylbenzidine (TMB), 2,2'-azino-bis (3-ethylbenzothiazoline-6-sulphonic acid) (ABTS), or 3,3'-diaminobenzidine (DAB).
209. The method, test substrate, or kit of any one of the preceding paragraphs, wherein the test substrate is a test strip of paper.
210. The method of any one of the preceding paragraphs, wherein the tags are obtained from a product of interest.
211. The method of any one of the preceding paragraphs, wherein the substrate of (a) is provided to an entity of a supply chain.
212. The method of paragraph 211, wherein the entity is selected from a manufacturer, a supplier, a producer, a distributor, and a retailer, and wherein the second entity of the supply chain is selected from a producer, a distributor, a retailer, and a customer.
213. A nanoparticle-based authentication method, comprising:
distributing to a first entity of a supply chain a tag; and
distributing to a second entity of the supply chain an authenticating identifier that comprises a first nanoparticle linked to a first authentication strand, a second nanoparticle linked to a second authentication strand, and optionally a third authentication strand,
wherein in solution the tag binds to the first authentication strand, the second authentication strand, and/or the third authentication strand and triggers aggregation or disaggregation of the first nanoparticle and the second nanoparticle to produce a color change in the solution.
214. A nanoparticle-based authentication method, comprising:
contacting a product of interest with a tag at a first stage of a supply chain;
optionally removing the tag from the product of interest at a second stage of the supply chain; and
combining the tag with a solution comprising a first nanoparticle linked to a first authentication strand, a second nanoparticle linked to a second authentication strand, and optionally a third authentication strand,
wherein in solution the tag binds to the first authentication strand, the second authentication strand, and/or the third authentication strand and triggers aggregation or disaggregation of the first nanoparticle and the second nanoparticle to produce a color change in the solution.
215. A nanoparticle-based authentication method, comprising:
combining, in a solution, a first nanoparticle linked to a first authentication strand, a second nanoparticle linked to a second authentication strand, optionally a third authentication strand, and a tag that binds to the first authentication strand, the second authentication strand, and/or the third authentication strand; and
triggering aggregation or disaggregation of the first nanoparticle and the second nanoparticle to produce a color change in the solution.
216. The method of any one of paragraphs 213-215, wherein
the tag comprises domain b* and domain a*,
the first authentication strand comprises domain a, and
the second authentication strand comprises domain b,
wherein domain a* binds to domain a, and domain b* binds to domain b, and wherein binding of the tag to the first authentication strand and to the second authentication strand triggers aggregation of the first nanoparticle and the second nanoparticle to produce the color change in the solution.
217. The method of paragraph 216, wherein domain b* and domain a* are configured in the 5' to 3' direction, optionally wherein the first nanoparticle is linked to the 5' end of the first authentication strand, and optionally wherein the second nanoparticle is linked to the 3' and of the second nanoparticle.
218. The method of any one of paragraphs 213-215, wherein
the tag comprises domain X* and domain a,
the first authentication strand comprises domain a*, domain X, and domain b*,
the second authentication strand comprises domain b and domain X*,
wherein the solution further comprises a third authentication strand that comprises domain b and domain X*, and wherein domain a* binds to domain a, domain b* binds to domain b, and domain X* binds to domain X.
219. The method of paragraph 218, wherein the second authentication strand is present in the solution at a concentration that is at least 2-fold greater than the concentration of both the first authentication strand and the third authentication strand, and wherein binding of the tag to the first authentication strand triggers aggregation of the first nanoparticle and the second nanoparticle to produce the color change in the solution.
220. The method of paragraph 218, wherein the third authentication strand is present in the solution at a concentration that is at least 2-fold greater than the concentration of both the first authentication strand and the second authentication strand, and wherein binding of the tag to the first authentication strand triggers disaggregation of the first nanoparticle and the second nanoparticle to produce the color change in the solution.
221. The method of any one of paragraphs 217-220, wherein domain X* and domain a of the tag are configured in the 5' to 3' direction; domain a*, domain X, domain b* of the first authentication strand are configured in the 5' to 3' direction; domain b and domain X* of the second authentication strand are configured in the 5' to 3' direction, and domain b and domain X* of the third authentication strand are configured in the 5' to 3' direction, optionally wherein the first nanoparticle is linked to the 5' end of the first authentication strand, and optionally wherein the second nanoparticle is linked to the 5' end of the second authentication strand.
222. The method of any one of paragraphs 213-215, wherein
the tag comprises domain a and domain b,
the first authentication strand comprises domain b* and domain a*,
the second authentication strand comprises domain b,
wherein domain a* binds to domain a, and domain b* binds to domain b, and wherein binding of the tag to the first authentication strand triggers disaggregation of the first nanoparticle and the second nanoparticle to produce the color change in the solution.

223. The method of paragraph 222, wherein domain a and domain b of the tag are configured in the 5' to 3' direction; and domain b* and domain a* of the first authentication strand are configured in the 5' to 3' direction, optionally wherein the first nanoparticle is linked to the 3' end of the first authentication strand, and optionally wherein the second nanoparticle is linked to the 3' end of the second authentication strand.

224. The method of any one of paragraphs 213-215, wherein
the tag comprises (a) domain X, (b) domain a and domain X, or (c) domain a, domain X, and domain b,
the first authentication strand comprises domain a,
the second authentication strand comprises domain b,
wherein the solution further comprises a third authentication strand that comprises domain b*, domain X*, and domain a*, wherein domain a* binds to domain a, domain b* binds to domain b, and domain X* binds to domain X, and wherein binding of the tag to the third authentication strand triggers disaggregation of the first nanoparticle and the second nanoparticle to produce the color change in the solution.

225. The method of paragraph 224, wherein
domain a and domain X of the tag are configured in the 5' to 3' direction, optionally wherein the first nanoparticle is linked to the 5' end of the first authentication strand, and optionally wherein the second nanoparticle is linked to the 3' end of the second authentication strand, or
domain a and domain X, and domain b of the tag are configured in the 5' to 3' direction, optionally wherein the first nanoparticle is linked to the 5' end of the first authentication strand, and optionally wherein the second nanoparticle is linked to the 3' end of the second authentication strand.

226. A nanoparticle-based authentication method, comprising:
distributing to a first entity of a supply chain a tag; and
distributing to a second entity of the supply chain a primer that binds to the tag, strand displacing polymerase, dNTPs, and a plurality of nanoparticles, wherein each nanoparticle of the plurality is linked to a authentication strand,
wherein in solution the primer, strand displacing polymerase, dNTPs, and the tag react to form a concatemer that binds to authentication strands of the nanoparticles and forms a nanoparticle aggregate to produce a color change in the solution.

227. A nanoparticle-based authentication method, comprising:
contacting a product of interest with a tag at a first stage of a supply chain;
optionally removing the tag from the product of interest at a second stage of the supply chain; and
combining the tag with a primer that binds to the tag, strand displacing polymerase, dNTPs, and a plurality of nanoparticles, wherein each nanoparticle of the plurality is linked to a authentication strand,
wherein in solution the primer, strand displacing polymerase, dNTPs, and the tag react to form a concatemer that binds to authentication strands of the nanoparticles and forms a nanoparticle aggregate to produce a color change in the solution.

228. A nanoparticle-based authentication method, comprising:
combining, in a solution, a tag, a primer that binds to the tag, strand displacing polymerase, dNTPs, and a plurality of nanoparticles, wherein each nanoparticle of the plurality is linked to a authentication strand;
producing a concatemer that binds to authentication strands of the nanoparticles; and
forming a nanoparticle aggregate to produce a color change in the solution.

229. The method of any one of paragraphs 226-228, wherein the tag is a catalytic hairpin comprising domain a, a loop domain, a first domain a*, and a second domain a*, wherein domain a binds to the first domain a*, wherein the primer comprises domain a, and wherein the authentication strand comprises domain a*.

230. The method of paragraph 229, wherein domain a, a loop domain, a first domain a*, and a second domain a* of the catalytic hairpin are configured in the 5' to 3' direction.

231. A nanoparticle-based authentication method, comprising:
distributing to a first entity of a supply chain a tag; and
distributing to a second entity of the supply chain a strand displacing polymerase, dNTPs, a first nanoparticle linked to a first authentication strand, and a second nanoparticle linked to a second authentication strand, wherein the tag binds to the first authentication strand,
wherein in solution the tag, strand displacing polymerase, dNTPs, first authentication strand, and second authentication strand react to form a double stranded molecule comprising the first and second nanoparticle to produce a color change in the solution.

232. A nanoparticle-based authentication method, comprising:
contacting a product of interest with a tag at a first stage of a supply chain;
optionally removing the tag from the product of interest at a second stage of the supply chain; and
combining the tag with a solution comprising a strand displacing polymerase, dNTPs, a first nanoparticle linked to a first authentication strand, and a second nanoparticle linked to a second authentication strand, wherein the tag binds to the first authentication strand, and
wherein in solution the tag, strand displacing polymerase, dNTPs, first authentication strand, and second authentication strand react to form a double stranded molecule comprising the first and second nanoparticle to produce a color change in the solution.

233. A nanoparticle-based authentication method, comprising:
combining, in a solution, a tag, a strand displacing polymerase, dNTPs, a first nanoparticle linked to a first authentication strand, and a second nanoparticle linked to a second authentication strand; and
producing form a double stranded molecule comprising the first and second nanoparticle to produce a color change in the solution.

234. The method of any one of paragraphs 231-233, wherein the tag comprises domain a and domain X, the first authentication strand is a catalytic hairpin comprising domain X, loop domain b, domain X*, and domain a*, and the second authentication strand is a catalytic hairpin comprising domain b*, loop domain a, domain X*, and domain b*.
235. The method of paragraph 229, wherein domain a, a loop domain, a first domain a*, and a second domain a* of the catalytic hairpin are configured in the 5' to 3' direction, and optionally wherein the first nanoparticle is linked to the 3' end of the first authentication strand, and optionally wherein the second nanoparticle is linked to the 5' end of the second authentication strand.
236. The method of any one of the preceding paragraphs, wherein domain a* comprises a nucleotide sequence complementary to domain a, domain b* comprises a nucleotide sequence complementary to domain b, and domain X* comprises a nucleotide sequence complementary to domain X.
237. The method of any one of the preceding paragraphs, wherein the length of the tag is shorter than 50 nucleotides.
238. The method of any one of the preceding paragraphs, wherein the nanoparticles are gold nanoparticles.
239. The method of any one of the preceding paragraphs, wherein the first entity is a manufacturer of the product of interest, and the second entity is a customer.
240. The method of any one of the preceding paragraphs, wherein the first entity of the supply chain is selected from a supplier, a producer, a distributor, and a retailer, and wherein the second entity of the supply chain is selected from a producer, a distributor, a retailer, and a customer.
241. A composition, comprising: a solution comprising a tag, a first nanoparticle linked to a first authentication strand, a second nanoparticle linked to a second authentication strand, and a third authentication strand, wherein the tag binds to the first authentication strand, the second authentication strand, and/or the third authentication strand and triggers aggregation or disaggregation of the first nanoparticle and the second nanoparticle to produce a color change in the solution.
242. The composition of paragraph 241, wherein the tag comprises domain b* and domain a*, the first authentication strand comprises domain a, and the second authentication strand comprises domain b, wherein domain a* binds to domain a, and domain b* binds to domain b, and wherein binding of the tag to the first authentication strand and to the second authentication strand triggers aggregation of the first nanoparticle and the second nanoparticle to produce the color change in the solution.
243. The composition of paragraph 242, wherein domain b* and domain a* are configured in the 5' to 3' direction, optionally wherein the first nanoparticle is linked to the 5' end of the first authentication strand, and optionally wherein the second nanoparticle is linked to the 3' and of the second nanoparticle.
244. The composition of paragraph 241, wherein the tag comprises domain X* and domain a, the first authentication strand comprises domain a*, domain X, and domain b*, the second authentication strand comprises domain b and domain X*, wherein the solution further comprises a third authentication strand that comprises domain b and domain X*, and wherein domain a* binds to domain a, domain b* binds to domain b, and domain X* binds to domain X.
245. The composition of paragraph 244, wherein the second authentication strand is present in the solution at a concentration that is at least 2-fold greater than the concentration of both the first authentication strand and the third authentication strand, and wherein binding of the tag to the first authentication strand triggers aggregation of the first nanoparticle and the second nanoparticle to produce the color change in the solution.
246. The composition of paragraph 244, wherein the third authentication strand is present in the solution at a concentration that is at least 2-fold greater than the concentration of both the first authentication strand and the second authentication strand, and wherein binding of the tag to the first authentication strand triggers disaggregation of the first nanoparticle and the second nanoparticle to produce the color change in the solution.
247. The composition of any one of paragraphs 244-246, wherein domain X* and domain a of the tag are configured in the 5' to 3' direction; domain a*, domain X, domain b* of the first authentication strand are configured in the 5' to 3' direction; domain b and domain X* of the second authentication strand are configured in the 5' to 3' direction, and domain b and domain X* of the third authentication strand are configured in the 5' to 3' direction, optionally wherein the first nanoparticle is linked to the 5' end of the first authentication strand, and optionally wherein the second nanoparticle is linked to the 5' end of the second authentication strand.
248. The composition of paragraph 241, wherein the tag comprises domain a and domain b, the first authentication strand comprises domain b* and domain a*, the second authentication strand comprises domain b, wherein domain a* binds to domain a, and domain b* binds to domain b, and wherein binding of the tag to the first authentication strand triggers disaggregation of the first nanoparticle and the second nanoparticle to produce the color change in the solution.
249. The composition of paragraph 248, wherein domain a and domain b of the tag are configured in the 5' to 3' direction; and domain b* and domain a* of the first authentication strand are configured in the 5' to 3' direction, optionally wherein the first nanoparticle is linked to the 3' end of the first authentication strand, and optionally wherein the second nanoparticle is linked to the 3' end of the second authentication strand.
250. The composition paragraph 241, wherein the tag comprises (a) domain X, (b) domain a and domain X, or (c) domain a, domain X, and domain b, the first authentication strand comprises domain a, the second authentication strand comprises domain b, wherein the solution further comprises a third authentication strand that comprises domain b*, domain X*, and domain a*, wherein domain a* binds to domain a, domain b* binds to domain b, and domain X* binds to domain X, and wherein binding of the tag to the third authentication strand triggers disaggregation of the first nanoparticle and the second nanoparticle to produce the color change in the solution.
251. The composition of paragraph 250, wherein domain a and domain X of the tag are configured in the 5' to 3' direction, optionally wherein the first nanoparticle is linked to the 5' end of the first authentication strand, and optionally wherein the second nanoparticle is linked to the 3' end of the second authentication strand, or domain a and domain X, and domain b of the tag are configured in the 5' to 3' direction, optionally wherein the first nanoparticle is linked to the 5' end of the first authentication strand, and optionally wherein the second nanoparticle is linked to the 3' end of the second authentication strand.

252. A composition, comprising: a solution comprising a tag, a primer that binds to the tag, strand displacing polymerase, dNTPs, and a plurality of nanoparticles, wherein each nanoparticle of the plurality is linked to a authentication strand, and wherein in solution the primer, strand displacing polymerase, dNTPs, and the tag react to form a concatemer that binds to authentication strands of the nanoparticles and forms a nanoparticle aggregate to produce a color change in the solution.

253. The composition of paragraph 252, wherein the tag is a catalytic hairpin comprising domain a, a loop domain, a first domain a*, and a second domain a*, wherein domain a binds to the first domain a*, wherein the primer comprises domain a, and wherein the authentication strand comprises domain a*.

254. The composition of paragraph 253, wherein domain a, a loop domain, a first domain a*, and a second domain a* of the catalytic hairpin are configured in the 5' to 3' direction.

255. A composition, comprising: a tag, a strand displacing polymerase, dNTPs, a first nanoparticle linked to a first authentication strand, and a second nanoparticle linked to a second authentication strand, wherein the tag binds to the first authentication strand, and wherein in solution the tag, strand displacing polymerase, dNTPs, first authentication strand, and second authentication strand react to form a double stranded molecule comprising the first and second nanoparticle to produce a color change in the solution.

256. The composition of paragraph 255, wherein the tag comprises domain a and domain X, the first authentication strand is a catalytic hairpin comprising domain X, loop domain b, domain X*, and domain a*, and the second authentication strand is a catalytic hairpin comprising domain b*, loop domain a, domain X*, and domain b*.

257. The composition of paragraph 256, wherein domain a, a loop domain, a first domain a*, and a second domain a* of the catalytic hairpin are configured in the 5' to 3' direction, and optionally wherein the first nanoparticle is linked to the 3' end of the first authentication strand, and optionally wherein the second nanoparticle is linked to the 5' end of the second authentication strand.

258. The composition of any one of the preceding paragraphs, wherein domain a* comprises a nucleotide sequence complementary to domain a, domain b* comprises a nucleotide sequence complementary to domain b, and domain X* comprises a nucleotide sequence complementary to domain X.

259. The composition of any one of the preceding paragraphs, wherein the length of the tag is shorter than 50 nucleotides.

260. The composition of any one of the preceding paragraphs, wherein the nanoparticles are gold nanoparticles.

EXAMPLES

Example 1

Experimental validation of nanoparticle-based colorimetric authentication is depicted in FIGS. 29A-29B. Fifteen (15) nm gold nanoparticles conjugated to two separate sequences (a and b) are first aggregated together using a splint strand b*-t*-a* (FIG. 29A). After aggregation, a tag a-t-b is used to displace the splint strand from the nanoparticles, thus de-stabilizing the aggregation and allowing the nanoparticles to separate and change the solution color. This process is recorded, and several successive screenshots showing the color changing only in the tube with the correct barcode are depicted in FIG. 29B (top). Further images at later time points show that the tubes with no tag added or the wrong tag added remain light purple in color, and the solution with the correct tag added turns red (FIG. 29B (bottom)).

All references, patents and patent applications disclosed herein are incorporated by reference with respect to the subject matter for which each is cited, which In some embodiments may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

This application is related to U.S. Provisional Patent Application No. 62/646,728, U.S. Provisional Patent Application No. 62/649,431, U.S. Provisional Patent Application No. 62/650,119, U.S. Provisional Patent Application No. 62/650,096, and U.S. Provisional Patent Application No. 62/739,756; each of which are incorporated herein by reference in their entirety.

What is claimed is:

1. A method of detecting a target nucleic acid, comprising contacting the target nucleic acid with an authenticating identifier composition, wherein the target nucleic acid comprises a first strand comprising domain x* and domain a, and the authenticating identifier composition comprises:
   (a) a second strand comprising domain a*, domain x, domain b*, and a first molecule of a quencher-fluorophore pair, wherein domain a* binds to domain a, and domain x binds to domain x*;
   (b) a third strand comprising a second molecule of the quencher-fluorophore pair, domain b, and domain x*, wherein domain b binds to domain b*; and
   (c) a fourth strand comprising domain b and domain x*; wherein binding of the second strand to the first strand produces a detectable signal, wherein the detectable signal is an optical signal.

2. The method of claim 1, wherein the first strand of the target nucleic acid comprises domain x* and domain a in a 5' to 3' direction; the second strand comprises domain a*, domain x, domain b*, and the first molecule of a quencher-fluorophore pair in a 5' to 3' direction; the third strand comprises the second molecule of the quencher-fluorophore pair, domain b, and domain x* in a 5' to 3' direction; and the fourth strand comprises domain b and domain x* in a 5' to 3' direction.

3. The method of claim 1, wherein the first strand of the target nucleic acid comprises domain x* and domain a in a 3' to 5' direction; the second strand comprises domain a*, domain x, domain b*, and the first molecule of a quencher-fluorophore pair in a 3' to 5' direction; the third strand comprises the second molecule of the quencher-fluorophore pair, domain b, and domain x* in a 3' to 5' direction; and the fourth strand comprises domain b and domain x* in a 3' to 5' direction.

4. The method of claim 1, wherein a concentration of the fourth strand in the authenticating identifier composition is greater than a combined concentration of the second and third strands.

5. The method of claim 4, wherein the concentration of the fourth strand in the authenticating identifier composition is at least 2-fold greater than the combined concentration of the second and third strands.

6. The method of claim 1, wherein the first, second, third, and/or fourth strand is 10-30 nucleotides in length.

7. The method of claim 1, wherein at least one of the strands of the authenticating identifier composition is immobilized to a surface.

8. The method of claim 7, wherein the surface is a capillary strip or paper-based material.

9. The method of claim 8, wherein the nanoparticle is a gold nanoparticle.

10. The method of claim 7, wherein the surface is a surface of a nanoparticle.

11. The method of claim 10, wherein the first catalytic hairpin strand comprises domain b, the loop domain, domain b* and domain a* in a 5' to 3' direction; and the second catalytic hairpin strand comprises domain c, the loop domain, domain c* and domain b* in a 5' to 3' direction.

12. The method of claim 10, wherein the first catalytic hairpin strand comprises domain b, the loop domain, domain b* and domain a* in a 3' to 5' direction; and the second catalytic hairpin strand comprises domain c, the loop domain, domain c* and domain b* in a 3' to 5' direction.

13. The method of claim 1, wherein at least one of the strands of the authenticating identifier composition is immobilized to a test substrate comprising (i) a source region, (ii) a test region comprising the immobilized strand(s), and (iii) a control region.

14. The method of claim 1, wherein at least one of the strands of the authenticating identifier composition is immobilized to a test substrate comprising (i) a source region comprising enzyme-linked strands, (ii) a test region comprising the immobilized strand(s) and an embedded enzyme substrate, and (iii) a control region comprising an embedded enzyme substrate and immobilized control strands that bind to the enzyme-linked strands.

15. The method of claim 1, wherein contacting of the target nucleic acid with the authenticating identifier composition is performed at a temperature of about 20 to 25° C.

16. A method of detecting a target nucleic acid, comprising
   (a) contacting the target nucleic acid with a first catalytic hairpin strand that comprises domain b, a loop domain, domain b* and domain a* and a second catalytic hairpin strand that comprises domain c, a loop domain, domain c* and domain b*, wherein domain b binds to domain b*, and domain c binds to domain c*; and
   (b) removing the first and second catalytic hairpin strands from the target nucleic acid;
   (c) combining the removed catalytic hairpin strands with (i) a primer comprising domain a, wherein domain a binds to domain a*, (ii) a strand displacing polymerase, and (iii) dNTPs, and producing a key strand comprising domain a, domain b, and domain c; and
   (d) authenticating the key strand using a molecular lock composition, wherein the molecular lock composition comprises a lock strand comprising domain a*, domain b*, and domain c*, and wherein binding of the lock strand to the key strand produces a detectable signal, wherein the detectable signal is an optical signal.

17. The method of claim 16, wherein the first key strand of comprises domain a and domain x in a 5' to 3' direction; and the second key strand comprises domain b and domain y in a 5' to 3' direction.

18. The method of claim 16, wherein the first key strand comprises domain a and domain x in a 3' to 5' direction; and the second key strand comprises domain b and domain y in a 3' to 5' direction.

19. A method of detecting a target nucleic acid, comprising
   (a) contacting the target nucleic acid with a first key strand that comprises domain a and domain x and a second key strand that comprises domain b and domain y; and
   (b) removing the first and second key strands from the target nucleic acid;
   (c) combining the removed key strands with a molecular lock composition, wherein the molecular lock composition comprises (i) a first lock strand comprising, in a 5' to 3' direction, a first molecule of a quencher-fluorophore pair, domain y*, domain b*, domain x*, and domain a*, (ii) a second lock strand comprising, in a 5' to 3' direction, domain x and domain b, and (iii) a third lock strand comprising, in a 5' to 3' direction, domain y and a second molecule of the quencher-fluorophore pair, wherein domain a binds to domain a*, domain x binds to domain x*, domain b binds to domain b*, and domain y binds to domain y*, wherein binding of the first and second key strands to the first lock strand produces a detectable signal, wherein the detectable signal is an optical signal.

* * * * *